(12) United States Patent
Ruxer et al.

(10) Patent No.: US 7,582,640 B2
(45) Date of Patent: Sep. 1, 2009

(54) VITRONECTIN RECEPTOR ANTAGONIST DERIVATIVES, METHOD FOR PREPARING SAME, USE THEREOF AS MEDICINES AND PHARMACEUTICAL COMPOSITIONS CONTAINING SAME

(75) Inventors: Jean-Marie Ruxer, Issy les Moulineaux (FR); Jean-Michel Lefrancois, Livry Gargan (FR); Bertrand Heckmann, Bures sur Yvette (FR)

(73) Assignee: Galapagos SAS, Romainville (FR)

( * ) Notice: Subject to any disclaimer, the term of this patent is extended or adjusted under 35 U.S.C. 154(b) by 522 days.

(21) Appl. No.: 10/536,028

(22) PCT Filed: Nov. 12, 2003

(86) PCT No.: PCT/FR03/03349

§ 371 (c)(1),
(2), (4) Date: May 18, 2005

(87) PCT Pub. No.: WO2004/048375

PCT Pub. Date: Jun. 10, 2004

(65) Prior Publication Data

US 2006/0052398 A1    Mar. 9, 2006

(30) Foreign Application Priority Data

Nov. 19, 2002 (FR) .................................. 02 14429

(51) Int. Cl.
C07D 471/04 (2006.01)
C07D 401/14 (2006.01)
A61K 31/506 (2006.01)

(52) U.S. Cl. ........................ 514/256; 544/326
(58) Field of Classification Search ................ 544/326; 514/256
See application file for complete search history.

(56) References Cited

U.S. PATENT DOCUMENTS

2008/0058348 A1* 3/2008 Lefrancois et al. .......... 514/256

OTHER PUBLICATIONS

Agrez et al., The alpha-v-beta-6 Integrin induces gelatinase B secretion in colon cancer cells, Int. J. Cancer, 81, pp. 90-97, 1999.*

Brooks et al., Integrin alpha-v-beta-3: A therapeutic target, DN&P, 10(8), pp. 456-461, Oct. 1997.*

Gladson et al., Vitronectin Expression in Differentiating Neuroblastic Tumors, American Journal of Pathology, vol. 150, No. 5, pp. 1631-1646, May 1997.*

Kim et al., Vitronectin-driven Human Keratinocyte Locomotion Is Mediated by the alpha-v-beta-5 Integrin Receptor, The Journal of Biological Chemistry, vol. 269, No. 43, pp. 26928-26932, Oct. 1994.*

Nip et al., The role of the Integrin vitronectin receptor, alpha-v-beta-3 in melanoma metastasis, Cancer and Metastasis Reviews, 14, pp. 241-252, 1995.*

Raynal et al., Bone Sialoprotein Stimulates in vitro Bone Resorption, Endocrinology, vol. 137, No. 6, pp. 2347-2354, 1996.*

Schvertz et al., Vitronectin, The International Journal of Biochemistry & Cell Biology, 31, pp. 539-544, 1999.*

Simone, Oncology: Introduction, Cecil Textbook of Medicine, 20th Edition, vol. 1, pp. 1004-1010, 1996.*

Antonov et al., Medline Abstract (American Journal of Pathology, vol. 165, Issue 1, pp. 247-258) Jul. 2004.*

* cited by examiner

*Primary Examiner*—Deepak Rao
(74) *Attorney, Agent, or Firm*—Foley & Lardner LLP; Stephen E. Reiter

(57) ABSTRACT

A subject of the invention is the compounds of formula (I):

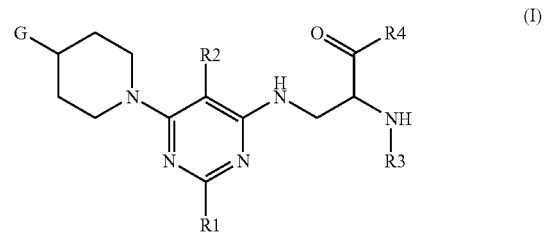

in which $R_1$, $R_2$, $R_3$, $R_4$ and G have the meanings indicated in the description, their preparation process, their use as medicaments having an antagonist activity on the vitronectin receptor and the pharmaceutical compositions containing them.

15 Claims, No Drawings

VITRONECTIN RECEPTOR ANTAGONIST DERIVATIVES, METHOD FOR PREPARING SAME, USE THEREOF AS MEDICINES AND PHARMACEUTICAL COMPOSITIONS CONTAINING SAME

This application is a 371 of PCT/FR03/03349 filed Nov. 12, 2003.

A subject of the present invention is new antagonist derivatives of the vitronectin receptor, their preparation process, their use as medicaments and the pharmaceutical compositions containing them.

A subject of the invention is the compounds of formula (I):

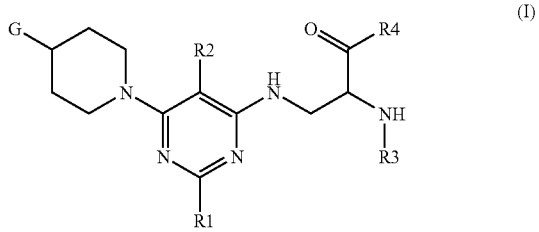

in which $R_1$, $R_2$, $R_3$, $R_4$ and G have the meanings indicated below as well as their physiologically acceptable salts and their prodrugs. The compounds of formula (I) are compounds having a pharmacological activity and can therefore be used as medicaments. They are antagonists of the vitronectin receptor and cell adhesion inhibitors and they inhibit bone resorption mediated by the osteoclasts. They are therefore useful for the therapeutic or prophylactic treatment of diseases which are caused at least in part by an undesirable increase in bone resorption, for example osteoporosis. A subject of the invention is also the processes for preparing the compounds of formula (I), their use, in particular as a medicament, and the pharmaceutical compositions containing them.

Bone is constantly subjected to a dynamic process which includes bone resorption and bone formation. These processes are mediated via specialized cells. Bone formation is the result of the deposit of a mineral matrix by the osteoblasts and bone resorption is the result of the dissolution of this bone matrix by the osteoclasts. The majority of bone disorders are caused by a disturbed equilibrium between bone formation and bone resorption. Osteoporosis is characterized by a dry loss of this bone matrix. An activated mature osteoclast resorbs the bone after adhesion to the bone matrix via the secretion of proteolytic enzyme, and protons inside the adhesion zone, resulting in depressions or hollows in the bone surface which appear when the osteoclast detaches itself from the bone.

Studies have shown that the fixation of the osteoclast on the bone is mediated by receptors: the integrins. Integrins are a superfamily of receptors mediating the cell/cell and more particularly cell/matrix adhesion process, including in particular $\alpha_{IIb}\beta_3$ as a blood platelet receptor (fibrinogen) and $\alpha_v\beta_3$ as a vitronectin receptor. The peptides containing the RGD unit as well as the anti $\alpha_v\beta_3$ antibodies are known for their ability to inhibit resorption of dentin and prevention of osteoclast adhesion on the mineralized matrices (Horton et al. Exp. Cell. Res. (1991), 195, 368). The peptide Echistatine, isolated from snake venom also contains an RGD unit and is described as an inhibitor of the adhesion of osteoclasts to the bone and is a powerful inhibitor of bone resorption in tissues cultured in vitro (Sato et al. J. Cell. Biol. (1990), 111, 1713) and in vivo in the rat (Fisher et al. Endocrinology (1993), 132, 1411).

The $\alpha_v\beta_3$ receptor is a transmembrane glycoprotein which is expressed in a large number of cells including endothelial cells, smooth muscle cells, osteoclast and cancerous cells which thus leads to a pluripotentiality of the compounds of formula (I) according to the invention.

In fact, the $\alpha_v\beta_3$ receptors expressed in the membrane of the osteoclasts are the basis of the adhesion/resorption process, contribute to the organization of the cell cytoskeleton, and are involved in osteoporosis. The $\alpha_v\beta_3$ receptors expressed in the smooth muscle cells of the aorta, stimulate their migration towards the neointima, which leads to the formation of arteriosclerosis and the occurrence of post-angioplastic recurrence of stenosis (Brown et al., cardiovascular Res. (1994), 28, 1815). The endothelial cells secrete growth factors which are mitogens for the endothelium and can contribute to the formation of new blood vessels (Angiogenesis). The antagonists of $\alpha_v\beta_3$ integrin can therefore lead to a regression of cancerous tumors by inducing apoptosis of the angiogenic blood vessels. (Brook et al. Cell (1994) 79, 1157).

Cheresh et al (Science 1995, 270, 1500) have described anti-$\alpha_v\beta_3$ antibodies or antagonists of the $\alpha_v\beta_3$ receptor which inhibit the process of angiogenesis induced by bFGF in the rat eye, a property which can be used for the treatment of retinopathies, in particular in diabetics.

The Patent Application WO-A-94/12181 describes aromatic or non-aromatic substituted systems and WO-A-94/08577 describes substituted heterocycles as antagonists of the fibrinogen receptor and inhibitors of platelet aggregation. EP-A-528586 and EP-A-528587 describe phenylalanine derivatives substituted by an aminoalkyl or a heterocycle and WO-A-95/32710 describes aryl derivatives as inhibitors of bone resorption by the osteoclasts. WO-A-96/00574 describes benzodiazepines and WO-A-96/00730 describes compounds which inhibit the fibrinogen receptor, in particular benzodiazepines which are linked to a ring with 5 nitrogenous members as antagonists of the vitronectin receptor. WO9800395, WO99/32457 and WO99/37621 describe tyrosine derivative antagonists of the vitronectin receptor. EP0820991 claims cycloalkyl derivatives as antagonists of the vitronectin receptor.

Other investigations have made it possible to show that the derivatives of formula (I) show marked activity as antagonists of the vitronectin receptor and of bone resorption mediated via the osteoclasts.

A subject of the invention is the compounds of formula (I):

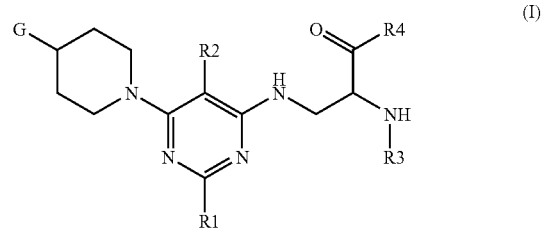

in all their isomeric forms, alone or in a mixture, as well as their physiologically acceptable addition salts, in which G represents $R^7R^8N$—$C(=NR^6)$—$NH$—$CO$—

Het-NH—CO—;

Het-NH—CH$_2$—,

Het-,

Het representing a monocyclic or polycyclic system, each ring being constituted by 4 to 10 aromatic or non aromatic members, the ring or at least one of the rings containing 1 to 4 nitrogen atoms, substituted or non substituted by one or more R$_9$ groups R$^1$ represents a hydrogen atom; a (C$_5$-C$_{14}$)-aryl ; (C$_5$-C$_{14}$)-aryl-(C$_1$-C$_4$)-alkyl -group; an amino radical non substituted or monosubstituted or disubstituted by an alkyl radical and/or an acyl radical containing 1 to 4 carbon atoms;

R$^2$ represents a hydrogen atom; a halogen atom; a nitro group; an alkyl radical containing 1 to 4 carbon atoms; an amino radical non substituted or monosubstituted or disubstituted by an alkyl and/or an acyl containing 1 to 4 carbon atoms; a-(CH$_2$)$_{0-2}$—CO$_2$R$^5$ group; or a-(CH$_2$)$_{0-2}$—OR$^5$ group;

R$^3$ represents
  a hydrogen atom
  a —CO$_2$R$^5$ radical,
  an —SO$_2$R$^5$ radical or
  a monocyclic or polycyclic system, each ring being constituted by 4 to 10 aromatic or non aromatic members, the ring or at least one of the rings containing 1 to 4 heteroatoms chosen from N, O or S, substituted or non substituted by one or more R$_9$ radicals, R$^4$ represents OH; (C$_1$-C$_8$)-alkoxy-; (C$_5$-C$_{14}$)-aryl-(C$_1$-C$_4$)-alkyloxy-; (C$_5$-C$_{14}$)-aryloxy-; (C$_3$-C$_{12}$)-cycloalkyloxy; (C$_3$-C$_{12}$)-cycloalkyl-(C$_1$-C$_4$)-alkyloxy-; (C$_1$-C$_8$)-alkylcarbonyloxy-(C$_1$-C$_4$)-alkyloxy-; (C$_5$-C$_{14}$)-aryl-(C$_1$-C$_4$)-alkylcarbonyloxy-(C$_1$-C$_4$) alkyloxy-; (C$_1$-C$_8$) dialkylaminocarbonylmethyloxy-; (C$_5$-C$_{14}$)-aryl-(C$_1$-C$_4$)-dialkylaminocarbonylmethyloxy-; an amino radical non substituted or monosubstituted or disubstituted by a (C$_1$-C$_4$)-alkyl and/or (C$_5$-C$_{14}$)-aryl and/or (C$_5$-C$_{14}$)-aryl-(C$_1$-C$_4$)-alkyl- radical and/or a (C$_1$-C$_5$)-acyl radical ; or the remainder of an amino acid D or L;

R$^5$ represents (C$_1$-C$_8$)-alkyl ; (C$_5$-C$_{14}$)-aryl ; (C$_5$-C$_{14}$)-aryl-(C$_1$-C$_4$)-alkyl-; (C$_3$-C$_{12}$)-cycloalkyl or (C$_3$-C$_{12}$)-cycloalkyl-(C$_1$-C$_4$)-alkyl-, bicycloalkyl-(C$_1$-C$_4$)-alkyl-, tricycloalkyl-(C$_1$-C$_4$)-alkyl-, said aryl, alkyl, cycloalkyl, bicycloalkyl and tricycloalkyl radicals being non substituted or substituted by one or more chosen R$^9$ groups;

R$^6$ represents a hydrogen atom; a hydroxyl; nitro, (C$_1$-C$_6$)-alkyl-O—CO—; or (C$_1$-C$_6$)-alkyl-O—CO—O— group;

R$^7$ and R$^8$, independently of one another represent a hydrogen atom or a (C$_1$-C$_6$)-alkyl radical non substituted or substituted by R$_9$;

R$^9$ represents halogen ; amino ; nitro ; hydroxyl, (C$_1$-C$_4$)-alkyloxy-; (C$_1$-C$_4$)-alkylthio-; carboxy; (C$_1$-C$_4$)-alkyloxycarbonyl-; (C$_1$-C$_8$)-alkyl non substituted or substituted by one or more halogen atoms, (C$_5$-C$_{14}$)-aryl, (C$_5$-C$_{14}$)-aryl-(C$_1$-C$_4$)-alkyl- All the radicals which can be found several times in the compounds of formula (I), for example the R$_3$ radical, are independent of one another and can be identical or different.

The alkyl radicals can be linear or branched, saturated or mono- or polyunsaturated. This also applies when they carry a substituent or when they are included in groups such as for example alkoxy, alkoxycarbonyl, aralkyl or heteroarylalkyl.

By (C$_1$-C$_8$)-alkyl is meant the methyl, ethyl, propyl, butyl, pentyl, hexyl, heptyl, octyl, nonyl radicals, the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Among the preferred radicals the (C$_1$-C$_4$)-alkyl groups can be mentioned such as methyl, ethyl, n-propyl, isopropyl, n-butyl, isobutyl, and tert-butyl. Preferably alkyl represents methyl or ethyl.

The cycloalkyl radicals can be monocyclic, bicyclic or tricyclic. They are for example cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl radicals which if appropriate can be substituted for example by an alkyl containing 1 to 4 carbon atoms. As substituted cycloalkyl radicals, there can be mentioned 4-methylcyclohexyl and 2,3-dimethylcyclohexyl.

The bicycloalkyl and tricycloalkyl radicals can be non-substituted or substituted in any position, for example by one or more oxo groups and/or 1 or more identical or different alkyl groups such as methyl or isopropyl and preferably methyl. The junction bond of the bi or tricyclic radical can be situated in all positions of the molecule. The bond can be situated at the bridged carbon atom or one of the other carbon atoms. This bond can also take any position from the point of view of the stereochemistry, for example exo or endo. As examples of bicycloalkyl or tricycloalkyl radicals, there can be mentioned camphanyl, bornyl, adamantyl such as 1-adamantyl or 2-adamantyl, caranyl, epii-sobornyl, epibornyl, norbornyl or norpinanyl.

By halogen is meant fluorine, chlorine, bromine or iodine.

By the term (C$_5$-C$_{14}$)-aryl is meant
  either the heterocyclic (C$_5$-C$_{14}$)-aryl radicals (=(C$_5$-C$_{14}$)-heteroaryl), in which one or more carbon atoms of the ring are replaced with a heteroatom such as nitrogen, oxygen or sulphur,
  or the carbocyclic (C$_6$-C$_{14}$)-aryl radicals.

Among the carbocyclic (C$_6$-C$_{14}$)-aryl radicals, phenyl, naphthyl, biphenylyl, anthryl or fluorenyl and quite particularly 1-naphthyl, 2-naphthyl and phenyl can be mentioned.

Unless indicated otherwise, the aryl radicals, in particular phenyl, can be non-substituted or substituted by one or more identical or different radicals chosen from (C$_1$-C$_8$)-alkyl, in particular (C$_1$-C$_4$)alkyl, hydroxyl, (C$_1$-C$_8$)-alkoxy, C$_1$-C$_8$)-alkoxylthio, halogen such as fluorine, chlorine and bromine, nitro, amino, (C$_1$-C$_4$)alkylamino, di-(C$_1$-C$_4$)alkylamino, trifluoromethyl, hydroxyl, methylenedioxy, cyano, aminocarbonyl, (C$_1$-C$_4$)alkylaminocarbonyl, di-(C$_1$-C$_4$)alkylaminocarbonyl, carboxy, (C$_1$-C$_4$)-alkoxycarbonyl, phenyl, phenoxy, benzyl and benzyloxy.

In the case of monosubstituted phenyl, the substituent can be situated in position 2, 3 or 4, and preferably in position 3 or 4. In the case where the phenyl is disubstituted, the substituents can be in position 2, 3 or 2, 4 or 2, 5 or 2, 6 or 3, 4 or 3, 5. Preferably, in the disubstituted phenyls, the two substituents are in position 3,4. When this phenyl is trisubstituted, the positions are as follows: 2, 3, 4 or 2, 3, 5 or 2, 3, 6 or 2, 4, 5 or 2, 4, 6 or 3, 4, 5. In the same way, the naphthyl radicals or other aryl radicals can be substituted in any position, for example the 1-naphthyl radical in position 2-, 3-, 4-, 5-, 6-, 7-, and 8 and the 2-naphthyl radical in position 1-, 3-, 4-, 5-, 6-, and 7.

The (C$_5$-C$_{14}$)-aryl group can also represent a monocyclic or polycyclic aromatic system in which 1, 2, 3, 4 or 5 carbon atoms of the ring are replaced with heteroatoms, in particular identical or different from the group constituted by nitrogen, oxygen and sulphur. Among the heterocyclic (C$_5$-C$_{14}$)-aryl (=(C$_5$-C$_{14}$)-heteroaryl) groups there can be mentioned the 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups or also benzocondensed, cyclopenta- cyclohexa- or cyclohepta-condensed derivatives of these radicals. The heterocyclic system can be substituted by the same substituents mentioned above for the carbocyclic system.

The optically active carbon atoms contained in the compounds of formula (I) can independently from one another show the R configuration or the S configuration.

The compounds of formula (I) can be in the form of pure enantiomers or pure diastereoisomers or in the form of a mixture of enantiomers, for example in the form of racemates or mixtures of diastereoisomers.

A subject of the present invention is therefore pure enantiomers, mixtures of these enantiomers, pure diastereoisomers and mixtures of these diastereoisomers.

The invention relates to mixtures of two or more than two stereoisomers of formula (I) and all the ratios of these stereoisomers in said mixtures.

The compounds of formula (I) can, if appropriate, be present in the form of E isomers or Z isomers. A subject of the invention is therefore the pure E isomers, the pure Z isomers and the E/Z mixtures in any ratio.

The invention also relates to all the tautomer forms of the compounds of formula (I), relating for example to the form represented by formula (I), with $G=R_7R_8N-C(=NR_6)-NH-CO-$ the form in which acylguanidine is present in the form of a $-CO-N=C(NHR_1)-NR_2R_7$ group, and all the other forms which differ by the different position of the hydrogen atom are considered.

The diastereoisomers, including the E/Z isomers, can be separated into individual isomers, for example by chromatography. The racemates can be separated into two enantiomers by standard methods such as chiral phase chromatography or by resolution methods.

The physiologically acceptable salts of the compounds of formula (I) are in particular salts which can be used pharmaceutically or non-toxic salts or salts which can be used physiologically.

When the compounds of formula (I) contain an acid group such as carboxylic acid, they are for example salts of alkali or alkaline earth metals such as sodium, potassium, magnesium, calcium salts, and also the salts formed with physiologically acceptable quaternary ammonium ions and the addition salts with acids such as ammonia and physiologically acceptable organic amines such as for example triethylamine, ethanolamine or tris-(2-hydroxyethyl)amine.

When the compounds of formula (I) contain a basic group, they can form an addition salt with acids, for example with inorganic acids such as hydrochloric, sulphuric, phosphoric acid or with organic carboxylic acids such as acetic, trifluoroacetic, citric, benzoic, maleic, fumaric, tartaric, methanesulphonic or para toluene sulphonic acid.

The compounds of formula (I) which comprise a basic group and an acid group, such as for example guanidino and carboxylic, can be present in the form of Zwitterions (betaines), which are also included in the present invention.

When appropriate a physiologically acceptable $Q^-$ anion can be contained in the compounds of formula (I) containing a charged ammonium group. It is preferably a monovalent anion or an equivalent of a polyvalent anion of an organic or inorganic non-toxic, physiologically acceptable and in particular pharmaceutically acceptable acid, for example the anion or an anion equivalent of one of the acids mentioned above, useful for the formation of the addition salts.

$Q^-$ can be for example one of the anions (or anion equivalent) of a group chosen from chlorine, sulphate, phosphate, acetate, trifluoroacetate, citrate, benzoate, maleate, fumarate, tartrate, methanesulphonate and paratoluenesulphonate.

The salts of the compounds of formula (I) can be obtained by standard methods known to a person skilled in the art, for example by combining a compound of formula (I) with an organic or inorganic acid or a base in a solvent or a dispersant or from another salt by cation or anion exchange.

The invention also includes all the salts of the compounds of formula (I) which, because of their low physiological acceptability, cannot be used directly as medicaments, but can be used as intermediate products to implement subsequent chemical modifications in the compounds of formula (I) or as starting products for the preparation of physiologically acceptable salts.

The present invention also includes all the solvates of the compounds of formula (I) for example the hydrates, the solvates formed with alcohols, and all the derivatives of the compounds of formula (I), for example the esters, prodrugs and other physiologically acceptable derivatives, as well as the metabolites of the compounds of formula (I).

A more particular subject of the invention is the compounds of formula (I) in which G represents a Het, Het-NHCO—, or Het-NH—CH$_2$— group in which Het represents

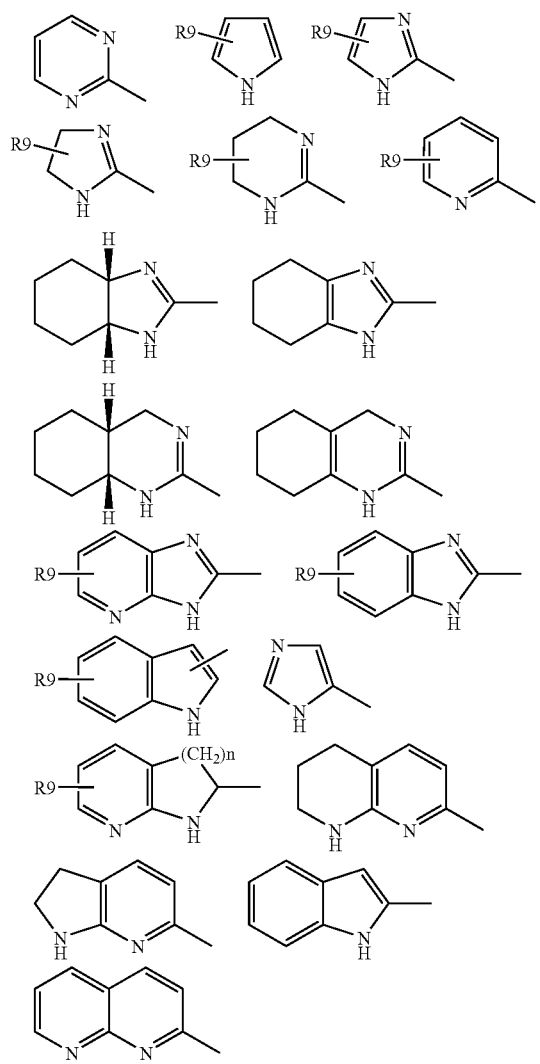

A more particular subject of the invention is the compounds of formula (I) as defined above in which $R_3$ is
a heterocycle chosen from

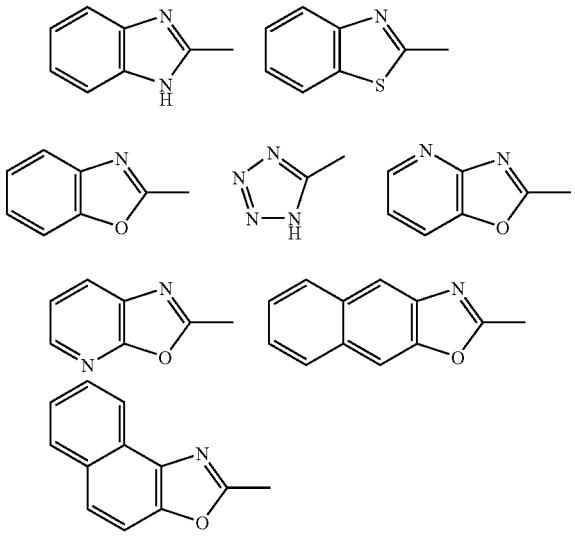

as well as their pharmaceutically acceptable addition salts.

A more particular subject of the invention is the compounds of formula (I) as defined above in which $R_3$ is a benzyloxycarbonyl group, as well as their pharmaceutically acceptable addition salts.

A more particular subject of the invention is the compounds of formula (I) as defined above in which $R_2$ is a hydrogen, an alkyl radical containing 1 to 4 carbon atoms, and quite particularly methyl and ethyl, or a fluorine atom as well as their pharmaceutically acceptable addition salts.

A more particular subject of the invention is the compounds of formula (I) as defined above in which:
G represents

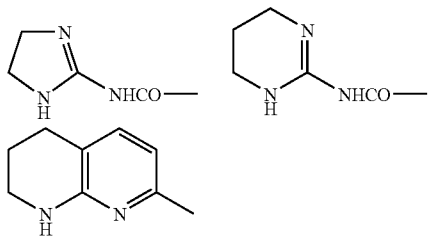

as well as their pharmaceutically acceptable addition salts.

A more particular subject of the invention is the compounds of formula (I) as defined above in which
G represents

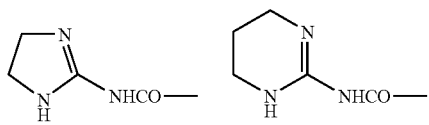

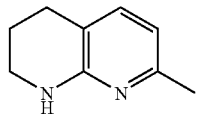

$R_1$ represents a hydrogen atom
$R_2$ represents a hydrogen atom, a fluorine atom, a methyl radical or an ethyl radical,
$R_3$ represents a benzyloxycarbonyl group
$R_4$ represents a hydroxy or $(C_1-C_4)$-alkyloxy group,
As well as the pharmaceutically acceptable addition salts A particular subject of the invention is the compounds of formula (I) the names of which follow:

3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine 3-[[5-ethyl-6-[4-[(1,2,3,4,5,6-hexahydro-2-pyrimidinyl)iminocarbonyl]-1-piperidinyl]-4-pyrimidinyl]amino]-N-[(phenylmethoxy)carbonyl]alanine 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alanine 3-[[6-[4-[(1,2,3,4,5,6-hexahydro-2-pyrimidinyl)iminocarbonyl]-1-piperidinyl]-5-methyl-4-pyrimidinyl]amino]-N-[(phenylmethoxy)carbonyl]alanine ethyl 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate isopropyl 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alaninate (1,1-dimethylethyl)3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate (1,1-dimethylethyl)3-[[5-methyl-6-[4-(1,2,3,4-tetrahydro-1,8-naphthyridin-7-yl)-1-piperidinyl]-4-pyrimidinyl]amino]-N-[(phenylmethoxy)carbonyl]alaninate (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-(1-naphthalenesulphonyl)alaninate (R) configuration or (S) configuration or their mixtures, as well as their addition salts.

A subject of the present invention is also a process for the preparation of the compounds of formula (I). The compounds can generally be prepared, for example during convergent synthesis by coupling two or more fragments which can be derived by retrosynthesis of the compounds of formula (I). In order to avoid the functional groups leading to undesirable or secondary reactions during each stage of synthesis, it can be advantageous or necessary during the synthesis of the compounds of formula (I), to introduce the functional groups in the form of precursors which are then converted into the desired functional groups or to temporarily block these functional groups by implementing a protective group strategy appropriate for the synthesis which is known to a person skilled in the art (Greene, Wuts Protective Group in Organic Synthesis, Wiley 1991).

Thus the compounds of formula (I) can be prepared, according to the following diagram:

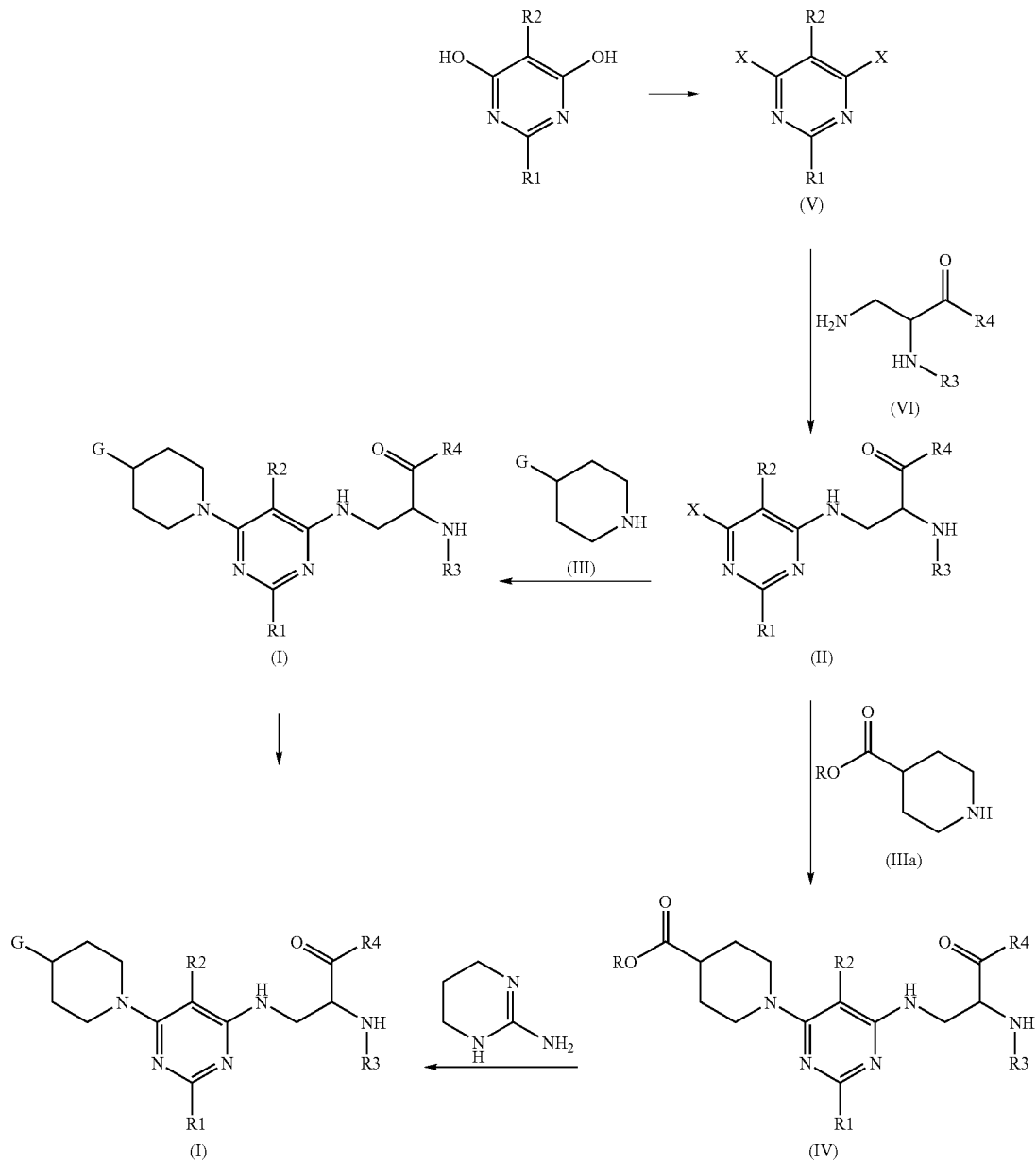

A subject of the invention is therefore a process for the preparation of the compounds of formula (I) in which a compound of formula (II)

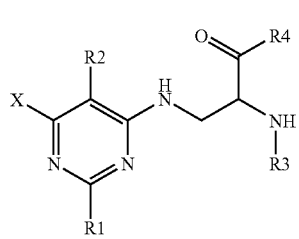

(II)

in which $R^1$, $R^2$, $R^3$ and $R^4$ are as defined previously is reacted, a) with a compound of formula (III)

(III)

in which G is as defined previously in the presence of a base or a transition metal coupling reagent b) then the compound of formula (I) is subjected, optionally with cleavage of the $R^3$—NH— function in order to regenerate the free amine, followed by condensation of the $R^3$ radicals of —CO$_2$—R$^5$ or —SO$_2$—R$^5$ structure, and/or if appropriate to the hydrolysis and optionally to esterification or to amidification and/or to salification.

By way of a variant, a subject of the invention is also a process for the preparation of the compounds of formula (I) in which a) a compound of formula (II) as defined previously is reacted with a compound of formula (IIIa):

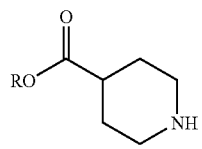

(IIIa)

in order to obtain the intermediate compound of formula (IV):

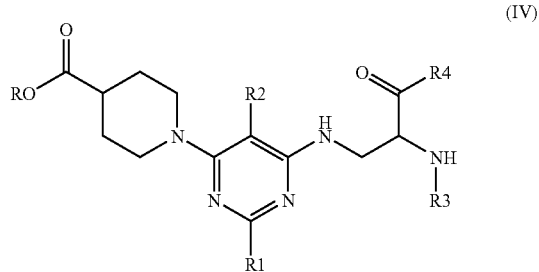

(IV)

b) then a compound of formula Het-NH$_2$ is reacted, in order to obtain the compounds of formula (I) with G representing a Het-NHCO— group, c) then the compound of formula (I) obtained is subjected, optionally with cleavage of the R$^3$—NH— function in order to regenerate the free amine, followed by condensation of radicals R$^3$ of —CO$_2$—R$^5$ or —SO$_2$—R$^5$ structure, and/or if appropriate, to esterification or to amidification and/or to salification.

Coupling of a compound of formula (II) with a piperidine derivative of formula (III) or (IIIa) can be carried out in the presence of a hindered strong base under reflux. In particular diisopropylethylamine is used. The reaction can vary from 4 to 12 hours under reflux.

At the level of the compound of formula (IV), when OR is a hydroxyl, therefore if a guanidine of formula (Het-NH$_2$) is reacted with a carboxylic acid of formula (IV), then the carboxylic acid is firstly activated.

Activation can be carried out for example with dicyclohexylcarbodiimide (DCCI) or with the O-((cyano(ethoxycarbonyl)-methylene)amino)-1,1,3,3-tetramethyluronium tetrafluoroborate (TOTU; König et al, Proc. 21st Europ. Peptide Symp. 1990 (Eds Giralt, Andreu), Escom, Leiden 1991, p. 243) or another activation agent currently used in peptide synthesis.

Apart from the free guanidines of formula (Het-NH$_2$), the guanidine salts can also be used in the reaction with the compounds of formula (IV), the free guanidines being formed in situ or by a separate stage by means of a base.

The reaction of an activated carboxylic acid derivative of formula (IV) with the guanidine (or derivative) of formula (Het-NH$_2$) is preferably carried out in a manner known per se in an organic protic or aprotic but inert solvent. In this case, solvents are used such as methanol, isopropanol, tert-butanol, dimethylformamide, dichloromethane or tetrahydrofuran at temperatures ranging from 0° C. to the reflux temperature of these solvents, in particular during the reaction of the methyl or ethyl esters (OR is a methoxy or an ethoxy) with guanidines.

The reactions of the compounds of formula (IV) with the free guanidines are advantageously carried out in an inert aprotic solvent such as dimethylformamide, tetrahydrofuran, dimethoxyethane or dioxane, if appropriate by adding a base such as for example potassium tert-butoxide, sodium methoxide or an inorganic base such as N-methylmorpholine. However, water can also be used as a solvent in the reactions of the compounds of formula (IV) with the guanidines of formula (Het-NH$_2$), for example by using a base such as sodium hydroxide.

The reaction mixture is then treated and if desired the reaction product is purified according to the methods known to a person skilled in the art.

The protective groups optionally present in the compounds of formula (I) obtained from the compounds of formulae (IV) with the amines or guanidines of formula Het-NH$_2$ or from the compounds of formula (II) with the compounds of formula (III) are then eliminated by standard processes; for example the tert-butyl ester groups are converted to carboxylic acid by treatment with trifluoroacetic acid, the benzyl groups are eliminated by hydrogenation or also the fluorenylmethoxycarbonyl groups are eliminated in the presence of secondary amine and other reactions are carried out using standard processes, for example by acylation reactions.

The hydrolysis reactions in order to obtain a derivative of acid (COR$^4$=CO$_2$H), the esterification reactions in order to obtain an ester or a prodrug (particularly COR$^4$=alkyloxycarbonyl or aryloxycarbonyl starting from the corresponding acid) or the amidification reactions (COR$^4$=mono or disubstituted aminocarbonyl starting from the corresponding acid) are carried out according to the usual methods known to a person skilled in the art.

In particular the hydrolysis is carried out in an acid medium, in the presence of trifluoracetic acid for example, in a halogenated organic solvent such as dichloromethane for example.

If necessary, the conversion to physiologically acceptable salts is carried out by processes known to a person skilled in the art.

The starting compounds of formula (II) can be prepared according to the processes described in the literature or also are accessible by analogy. The preparation of the compounds of formula (II) is illustrated in the diagram described above, it being understood that the present invention is not restricted to these syntheses or these starting products. It is not a major difficulty for a person skilled in the art to envisage modifications to the syntheses described in our Application for the preparation of other compounds of formula (II) according to the invention.

Therefore a subject of the invention is the process for the preparation of the compounds of formula (II) characterized in that a compound of formula (V):

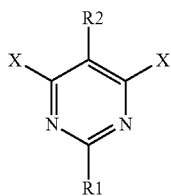

in which $R^1$ and $R^2$ are as defined previously, and X represents a halogen, preferably chlorine
is reacted with a compound of formula (VI):

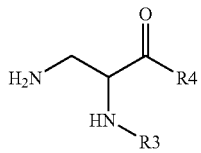

in which $R^3$ and $R^4$ are as defined previously, in the presence of a strong base.

In general, a hindered strong base is used such as diisopropylethylamine under reaction conditions known to a person skilled in the art for the implementation of nucleophilic substitution. Preferably the operation takes place in the presence of dimethylformamide and at reflux temperature. Moreover the COR4 group will preferably represent a hindered ester group such as the tertbutyloxycarbonyl group.

According to another variant of the invention, the products of formula (I) can also be prepared according to the following diagram:

According to the invention, the process for the preparation of the products of formula (I) consists of a) the reaction of a product of formula (IIa)

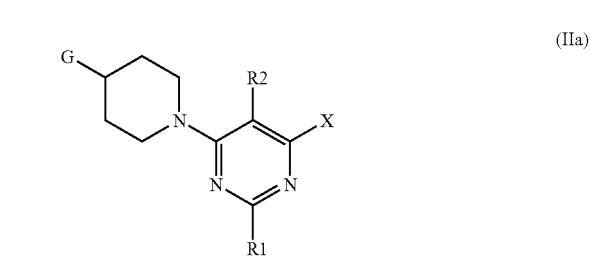

in which $R^1$, $R^2$, G and X are as defined previously, with a product of formula (VI)

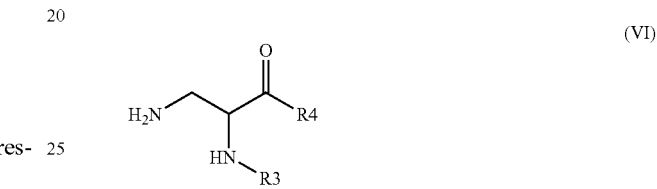

in which $R^3$ and $R^4$ are as defined previously, either in the presence of a strong base, or by catalysis with palladium, b) then the product of formula (I) is subjected, optionally to cleavage of the $R^3$—NH— function in order to regenerate the free amine, followed by condensation of the $R^3$ radicals of —$CO_2$—$R^5$ or —$SO_2$—$R^5$ structure, and/or if appropriate to hydrolysis and optionally to esterification or to amidification and/or to salification.

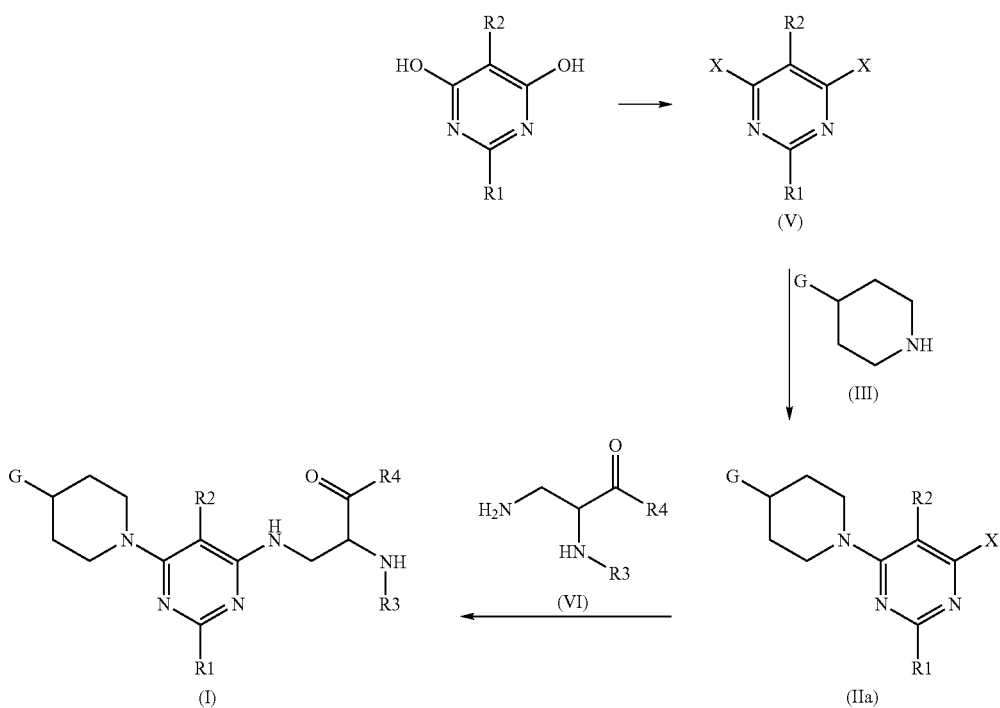

The reaction of the pyrimidine of formula (IIa) with the amine of general formula (VI) is carried out under conditions similar to the conditions described previously for the reaction of a pyrimidine of formula (V) with the amine of general formula (VI). In particular, it is possible to operate in diisopropylethylamine in an organic solvent such as an amide (dimethylacetamide, dimethylformamide for example), at a temperature comprised between 90° C. and the reflux temperature of the reaction mixture. It is also possible to operate by catalysis with palladium (for example tris(dibenzylideneacetone) dipalladium) in the presence of cesium fluoride, at the reflux temperature of the reaction mixture. It is understood that the functions which could interfere with the reaction are protected. The protection and release of these functions is carried out according to the usual methods which do not alter the remainder of the molecule.

The condensation of the $R^3$ radicals of $-CO_2-R^5$ or $-SO_2-R^5$ structure on the free amine, and the hydrolysis are carried out as described previously.

The pyrimidine derivatives of formula (IIa) can be prepared by the action of a product of formula (III)

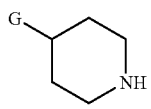

(III)

in which G is defined as previuosly, on a dihalogenated derivative of the pyrimidine of formula (V)

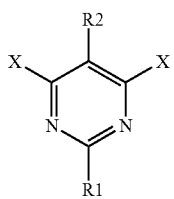

(V)

in which $R^1$, $R^2$ and X are defined as previously.

The reaction is advantageously carried out in the presence of a hindered strong base, at the reflux temperature of the reaction mixture. The operation is carried out under the conditions described hereafter in the examples and in particular in the presence of a hindered amine such as diisopropylethylamine, in an amide such as dimethylacetamide for example. It is understood that the functions which could interfere with the reaction are protected. The protection and release of these functions is carried out according to the usual methods which do not alter the remainder of the molecule.

The compounds of formula (I) are compounds having a pharmacological activity and can thus be used as medicaments in particular in the treatment or prevention of diseases of the bone, tumorous diseases as well as cardiovascular disorders.

Therefore a subject of the present invention is the compounds of formula (I) and/or their physiologically acceptable salts as a medicament.

The compounds of formula (I) as well as their physiologically acceptable salts and their prodrugs can be administered to animals, preferably mammals and in particular human beings as therapeutic or prophylactic medicaments.

They can be administered as they are or in a mixture with one or more other compounds of formula (I) or also in the form of a pharmaceutical preparation (pharmaceutical composition) which allows enteral or parenteral administration and which contains an effective dose of at least one compound of formula (I) and/or its physiologically acceptable salts as active ingredient as well as current and pharmaceutically inert supports and/or additives.

The pharmaceutical compositions according to the invention allow enteral or parenteral administration, containing an effective dose of at least one compound of formula (I) and/or its physiologically acceptable salts as active ingredient as well as one or more pharmaceutically inert supports and/or one or more usual additives.

Therefore a subject of the invention is the pharmaceutical compositions containing a compound of formula (I) as defined previously as well as one or more excipients.

The medicaments can be administered orally, for example in the form of pills, tablets, coated tablets, film-encased tablets, granules, gelatin capsules and soft capsules, solutions, syrups, emulsions, suspensions or aerosol mixtures.

The administration can however be carried out by rectal route, for example in the form of suppositories, by parenteral route, for example in the form of injectable solutions, infusions, microcapsules or implants, by percutaneous route, for example in the form of an ointment, solutions, pigments or colorants, by transdermal route in the form of patches, or by other routes such as in the form of an aerosol or nasal spray.

The pharmaceutical preparations according to the invention are prepared according to methods known per se, pharmaceutically inert organic or inorganic supports, being added to the compounds of formula (I) and/or their physiologically acceptable salts.

For the production of pills, tablets, coated tablets and hard gelatin capsules, it is possible to use for example lactose, corn starch or its derivatives, talc, stearic acid or its salts, etc. Suitable supports for soft gelatin capsules or for suppositories are for example fats, waxes, semi-solid or liquid polyols, natural or modified oils, etc. Appropriate vehicles for the preparation of solutions, for example injectable solutions, emulsions or syrups are for example water, alcohols, glycerol, polyols, sucrose, inverted sugars, glucose, vegetable oils, etc. Suitable supports for microcapsules or implants are for example glyoxilic acid and lactic acid copolymers. The pharmaceutical preparations normally contain from 0.5% to 90% by weight of the compounds of formula (I) and/or their physiologically acceptable salts.

In addition to the active ingredients and supports, the pharmaceutical preparations can contain additives such as, for example, diluting agents, disintegration agents, binding agents, lubricants, wetting agents, stabilizers, emulsifiers, preservatives, sweetening agents, colouring agents, flavouring or aromatizing agents, thickeners, buffering agents, and also solvents or solubilizing agents or agents to obtain a delayed release effect and also salts for modifying the osmotic pressure, coating agents or antioxidants.

They can also contain two or more compounds of formula (I) and/or their physiologically acceptable salts. Moreover, in addition to at least one or more compounds of formula (I) and/or their physiologically acceptable salts, they can contain at least one or more active ingredients which can be used for therapeutic or prophylactic uses.

The pharmaceutical preparations (pharmaceutical compositions) normally contain 0.2 to 500 mg, and preferably 1 to 200 mg of the compound of formula (I) and/or their physiologically acceptable salts and/or their prodrugs.

The compounds of formula (I) are quite particularly antagonists of the vitronectin receptors and are therefore capable for example of inhibiting the adhesion of osteoclasts on the surface of the bone and thus bone resorption by the osteoclasts.

The action of the compounds of formula (I) can be demonstrated for example in a test in which the inhibition of the binding of vitronectin to the cells which contain the vitronectin receptor is determined. Further information about this test is given below. As antagonists of the vitronectin receptor, the compounds of formula (I) and their physiologically acceptable salts are in general suitable for the treatment or prevention of diseases linked to the interactions between the vitronectin receptors and their ligands, in the process of cell-cell or cell-matrix interaction or which can be influenced by the inhibition of interactions of this type, to relieve or cure when inhibition of interactions of this type is desired. As explained at the beginning, such an interaction plays an important role in bone resorption, in angiogenesis or in cell proliferation of the vascular smooth muscle cells.

Bone diseases the treatment or prevention of which require the use of the compounds of formula (I) are in particular osteoporosis, hypercalcemia, osteopenia, for example caused by bony metastases, dental disorders for example parodontitis, hyperparathyroidism, periarticular erosions in rheumatoid arthritis, and Paget's disease. Moreover the compounds of formula (I) can be used to relieve, prevent or treat bone disorders which are caused by treatments with glucocorticoids, therapies linked to taking steroids or corticosteroids or male or female sex hormone deficiencies. All these disorders are characterized by bone loss, which is caused by a lack of equilibrium between bone formation and bone destruction and which can be favourably influenced by the inhibition of bone resorption by the osteoclasts. Besides this use as an inhibitor of bone resorption mediated via the osteoclasts, the compounds of formula (I) and their physiologically acceptable salts are used as inhibitors of tumorous growth or of cancerous metastases, in the treatment of inflammatory disorders, for the treatment or prevention of cardiovascular disorders, such as arteriosclerosis or restenosis, or the treatment or prevention of nephropathy or retinopathy such as for example diabetic retinopathy.

The compounds according to the invention can also have an activity with respect to other integrins which interact with their ligands via the tripeptide sequence RGD ($\alpha_v\beta_1$, $\alpha_v\beta_5$, $\alpha_{IIb}\beta_3$), giving them pharmacological properties which can be used to treat pathologies associated with these receptors.

This activity vis-à-vis the integrins therefore makes the compounds of formula (I) of use in the prevention or treatment of numerous diseases such as those mentioned above or in the publication by Dermot Cox DN§P 8(4) May 1995, 197-205 the content of which is incorporated in the present Application.

Therefore a more particular subject of the present invention is a compound of formula (I) and/or its physiologically acceptable salts as defined above as a medicament having an antagonist activity on the vitronectin receptor.

Therefore a more particular subject of the present invention is a compound of formula (I) and/or its physiologically acceptable salts and/or its prodrugs as defined above as a medicament having an inhibitory activity on bone resorption or for the treatment or prevention of osteoporosis.

Therefore a more particular subject of the present invention is a compound of formula (I) and/or its physiologically acceptable salts as defined above as a medicament having an inhibitory activity on tumorous growth or cancerous metastases.

Therefore a more particular subject of the present invention is a compound of formula (I) and/or its physiologically acceptable salts as defined above as a medicament having an anti-inflammatory activity or for the treatment or prevention of cardiovascular disorders, restenosis, arteriosclerosis, nephropathies or retinopathies.

A subject of the present invention is also the use of the compounds of formula (I) and/or their physiologically acceptable salts as defined above for the preparation of medicaments intended for the prevention or treatment of osteoporosis.

A subject of the present invention is also the use of the compounds of formula (I) and/or their physiologically acceptable salts as defined above for the preparation of medicaments intended to inhibit tumorous growth or cancerous metastases.

A subject of the present invention is also the use of the compounds of formula (I) and/or their physiologically acceptable salts as defined above for the preparation of medicaments intended for the prevention or the treatment of cardiovascular disorders, restenosis, arteriosclerosis, nephropathies or retinopathies.

When the compounds of formula (I) are used, the doses can vary within broad limits and must be set according to the person treated. This depends for example on the compound used and the nature and severity of the disease to be treated, whether the conditions are serious or acute and if a prophylactic treatment is used.

In the case of administration by oral route, the daily dose in general varies from 0.01 to 100 mg/kg and preferably from 0.1 to 50 mg/kg, in particular from 0.1 to 5 mg/kg. For example, for an adult weighing 75 kg, a daily dose can be envisaged varying from 0.3 to 0.5 mg/kg.

In the case of administration by intravenous route, the daily dose varies approximately from 0.01 to 100 mg/kg and preferably from 0.05 to 10 mg/kg.

The daily dose can be divided, in particular in the case of the administration of a large quantity of active ingredient, into several, for example 2, 3 or 4 parts. If appropriate, depending on individual behaviour, it may be necessary to administer different increasing or decreasing doses.

Apart from the use of the compounds of formula (I) as medicaments, it is also possible to envisage their use as a vehicle or support for active ingredients in order to deliver these active compounds specifically towards the target (Drug targeting, see Targeted Drug Delivery, R. C. Juliano, Handbook of Experimental Pharmacology, Vol 100, Ed. Born, G. V. R. et al, Springer Verlag). The active ingredients which can be delivered are in particular those used for the treatment or prevention of the diseases mentioned above.

The compounds of formula (I) and their salts can also be used as a diagnostic agent, for example for in vitro methods or as auxiliaries in biochemical studies in which blocking the vitronectin receptor or influencing cell-cell or cell-matrix interactions are desired. They can moreover be used as an intermediate for the preparation of other compounds, in particular other active ingredients, which are accessible from the compounds of formula (I), for example by modification or introduction of radicals or functional groups.

EXAMPLES

The products were identified by mass spectrum (MS), infrared (IR) and/or NMR spectrum. The compounds which were purified by chromatography using an eluent which contains for example acetic or trifluoroacetic acid, and which are then dried or in which, during the last synthesis stage, for example trifluoroacetic acid was used in order to eliminate a tert-butyl protective group, sometimes contain, depending on the manner in which the product was dried, the acid originating from the eluent or the last synthesis stage and are therefore found partially or completely in the form of the salt of the acid used, for example in the form of an acetic or trifluoroacetic acid salt. They can also be more or less hydrated.

Abbreviations/Chemical Names Optionally Used:

AcOEt: ethyl acetate; EDCI: 1-(3-dimethylaminopropyl)-3-ethyl-carbodiimide hydrichloride; DMF: dimethylformamide; DIPEA: Diisopropylethylamine; MeOH: methanol; TEA: triethylamine; TFA: trifluoroacetic acid; THF: tetrahydrofuran; MCPBA: meta-chloroperoxybenzoic acid; DBU: 1,8-diazabicyclo[5.4.0]undec-7-ene; PTSA: paratoluenesulphonic acid; DPPA: diphenylphosphorylazide; DMSO: dimethylsulphoxide; Pd/C Palladium on carbon; Boc: terbutoxycarbonyl; CBz: benzyloxycarbonyl; DCC 1,3-dicyclohexylcarbodiimide; BrTMS: bromotrimethylsi-lane; TMSI: trimethylsilane iodide.

IR: Infrared; NMR: Nuclear Magnetic Resonance; MS: Mass Spectrum; PES: Positive mode electrospray; sh.: shoulder; S: strong; s: singlet; d: doublet; t: triplet; quad: quadruplet; quint: quintuplet; b: broad; m: multiplet; J: coupling constant; Rf: retention factor (chromatography).

It is understood that in the examples which follow the products of Examples 1 to 5 are in racemic form, the products of Examples 6 to 9, 11, and 13 to 41 as well as their ester precursors are in (S) form on the asymmetrical centre of the 3-amino alanine and Examples 10 and 12 and if appropriate their ester precursors are in (R) form on the asymmetrical centre of the 3-amino alanine.

Preparation 1

Synthesis of 4,6-dichloro-5-ethyl-pyrimidine (Compound of formula (V)

A mixture of 5 g (35.7 mmoles) of 5-ethyl-4,6-dihydroxy-pyrimidine (marketed by Aldrich) in 30 ml of phosphorus oxychloride is taken to reflux for 1 hour. After returning to ambient temperature, a mixture of 4 ml of N,N-diethylaniline in 10 ml of phosphorus oxychloride is added dropwise and the reaction medium is taken to reflux for 4 hours. After returning to ambient temperature, the reaction medium is poured into a mixture of ice and water, followed by extracting with ethyl acetate, washing the organic phases with 2N hydrochloric acid, drying over magnesium sulphate and evaporating to dryness under vacuum. 6 g (Yield=95%) of a brown oil of expected product is obtained used as it is for the following.

TLC: Rf=0.5 (silicagel, eluent: dichloromethane-methanol 90-10)

Example 1

3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis(trifluoroacetate)

Stage a

Synthesis of (1,1-dimethylethyl)3-[(6-chloro-5-ethyl-4-pyrimidinyl)amino]-N-[(phenylmethoxy)carbonyl]alaninate

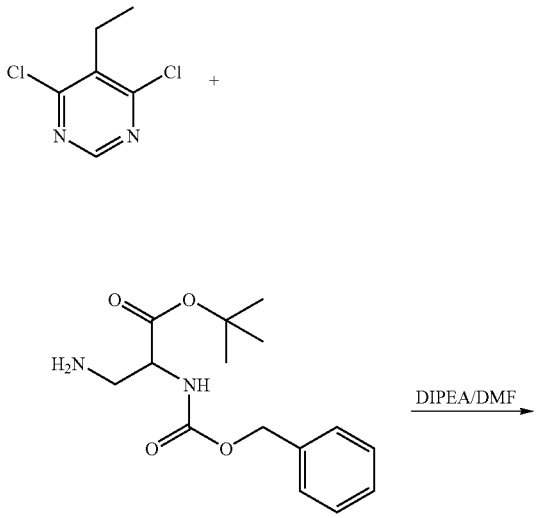

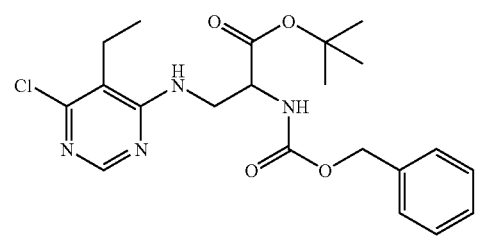

10 ml of diisopropylethylamine is added to a mixture of 3.8 g (21 mmoles) of 4,6-dichloro-5-ethyl-pyrimidine and 4.4 g (15 mmoles) of (1,1-dimethylethyl)3-amino-N-[(phenylmethoxy)carbonyl]alaninate (prepared according to J. Med. Chem. (2001), 44(8), 1158-1176) in 50 ml of dimethylformamide, then this mixture is heated at 120° C. for 6 hours. Then the dimethylformamide is eliminated under vacuum and the residue is taken up in a mixture of ethyl acetate, water and a saturated solution of sodium bicarbonate. The organic phase is decanted then dried over magnesium sulphate and the solvent is eliminated by evaporation under vacuum. The residue is chromatographed on silicagel eluting with a gradient of 100% heptane to heptane-ethyl acetate 50-50. 4.7 g (Yield=70%) of expected product is obtained in the form of an oil.

TLC: Rf=0.2 (silicagel, eluent: heptane-ethyl acetate 70-30)

IR (CHCl3): 3411 (NH); 1718 (C=O); 1571; 1498 cm-1 (Heterocycle+Aromatic+Amide)

1H-NMR (DMSO-d6): δ 1.02 (t, 3H, CH$_2$—CH$_3$); 1.30 (s, 9H, tBu); 2.57 (q, 2H, CH$_2$—CH$_3$); 3.74 (m, 2H, NH—CH$_2$—CH—NH); 4.29 (bq, 1H, NH—CH$_2$—CH—NH); 5.00 and 5.06 (syst. AB, 2H, O—CH$_2$-Ph); 7.22 (bt, 1H, NH—CH$_2$—CH—NH); 7.34 (m, 5H, Ph); 7.64 (bd, 1H, NH—CH$_2$—CH—NH); 8.16 ppm (s, 1H, N=CH—N)

HPLC/MS: (tr=26 min): 435 (MH+); 379 (MH-tBu+).

Stage b)

Synthesis of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate

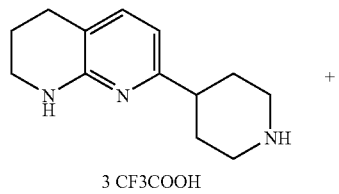

3 CF3COOH

+

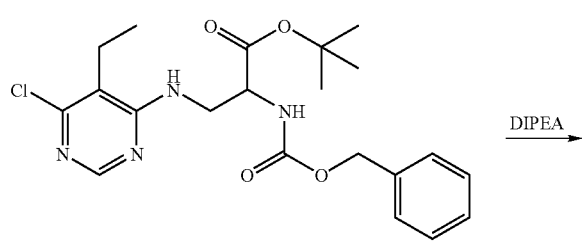

DIPEA →

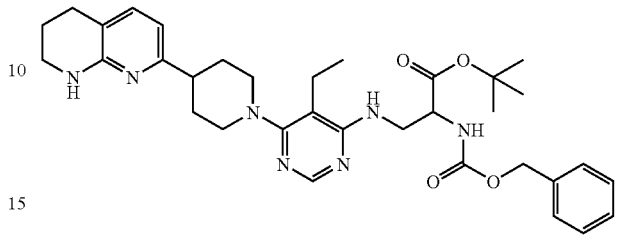

A mixture of 1.68 g (3 mmoles) of 1,2,3,4-tetrahydro-7-(4-piperidinyl)-1,8-naphthyridine, tris(trifluoroacetate) (prepared according to Patents EP1065207 or WO 0078317) and 7.5 g (14.1 mmoles base equivalents) of aminomethyl polystyrene (Polymer Labs 1.88 mmoles/g) in 200 ml of a solution of dichloromethane-methanol 50-50 is stirred at ambient temperature for 1 hour. The mixture is filtered, the resin is washed with methanol and dichloromethane and the filtrate is concentrated to dryness under vacuum producing 630 mg of free amine. 651 mg (1.5 mmoles) of (1,1-dimethylethyl) 3-[(6-chloro-5-ethyl-4-pyrimidinyl)amino]-N-[(phenylmethoxy)carbonyl]alaninate and 2 ml of diisopropylethylamine are added to this residue and the reaction medium taken to reflux for 8 hours, followed by evaporating to dryness under vacuum and the residue is taken up in ethyl acetate, water and a saturated solution of sodium bicarbonate. The organic phase is separated, dried over magnesium sulphate and the solvent evaporated off under vacuum. The residue is chromatographed on silicagel eluting successively with pure dichloromethane, a mixture of dichloromethane-methanol 90-10 then a mixture of dichloromethane-methanol-water-acetic acid 90-10-1-1. 115 mg (Yield=12%) of expected product is obtained in the form of oil. Another 280 mg (43%) of chlorinated starting compound is also recovered.

TLC: Rf=0.55 (alumina, eluent: heptane-ethyl acetate 50-50).

IR (CHCl3): 3438 (NH 1717 (C=O); 1583; 1500 cm-1 (Heterocycle+Aromatic+Amide).

1H-NMR (DMSO-d6): δ 1.06 (t, 3H, CH$_2$—CH$_3$); 1.31 (s, 9H, tBu); 1.77 (m, 2H, CH$_2$—CH$_2$—CH$_2$—NH); 1.78 (m, 4H, CH$_2$—CH—CH$_2$); 2.43 (q, 2H, CH$_2$—CH$_3$); 2.51 (m, 1H, CH$_2$—CH—CH$_2$); 2.61 (m, 2H, CH$_2$—CH$_2$—CH$_2$—NH); 2.82 and 3.44 (2m, 4H, CH$_2$—CH$_2$—N—CH$_2$—CH$_2$); 3.23 (m, 2H, CH$_2$—CH$_2$—C$_2$—NH); 3.72 (m, 2H, NH—CH$_2$—CH—NH); 4.23 (m, 1H, NH—CH$_2$—CH—NH); 5.03 (bd, 2H, CH$_2$-Ph); 6.22 (m, 1H, CH$_2$—CH$_2$—CH$_2$—NH); 6.30 and 7.05 (2m, 2H, H naphthyridine); 6.35 (m, 1H, NH—CH$_2$—CH—NH); 7.34 (m, 5H, Ph); 7.60 (m, 1H, NH—CH$_2$—CH—NH); 8.11 ppm (N=CH—N).

HPLC/MS: (rt=14 min): 616 (MH+).

Stage c

Synthesis of 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis (trifluoroacetate)

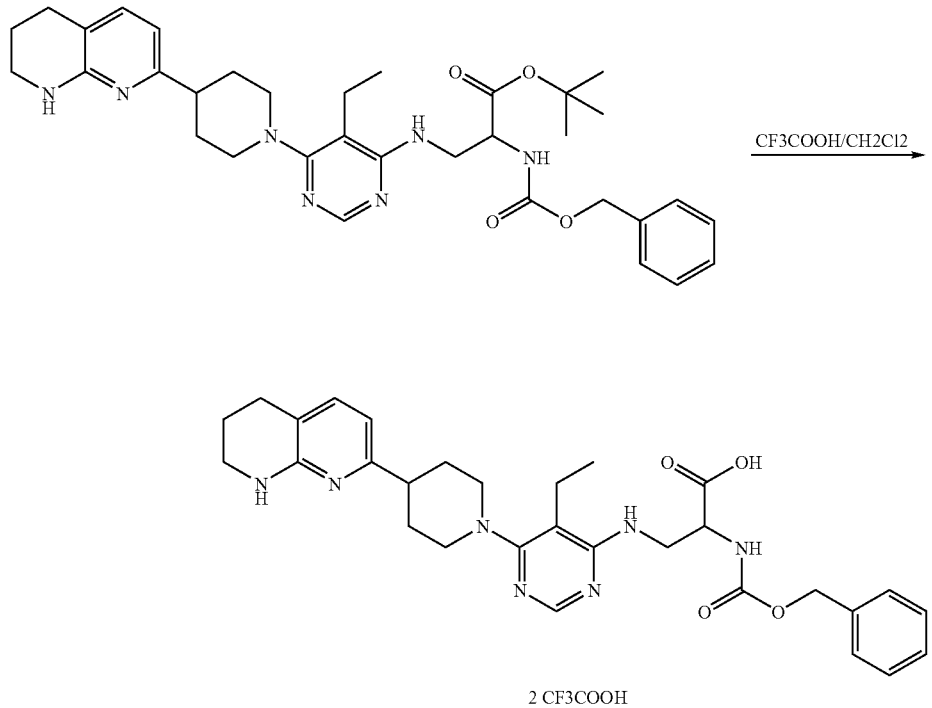

110 mg (0.18 mmoles) of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate in 5 ml of dichloromethane is stirred with 1 ml of trifluoroacetic acid at ambient temperature until the starting product disappears according to TLC (silicagel, eluent: CH2Cl2-MeOH—H2O—AcOH 90-10-1-1). Toluene is added and the reaction medium is evaporated to dryness under vacuum. The residue is solubilized in the minimum amount of dichloromethane with a little methanol then poured into diisopropyl ether. The precipitate is filtered. 108 mg (Yield=76%) of expected product is obtained in the form of an amorphous solid.

TLC: Rf=0.33 (silicagel, eluent: dichloromethane-methanol-water-acetic acid 90-10-1-1)

IR (CHCl$_3$): 1677 (C=O); 1626; 1586; 1500 cm-1 (Heterocycle+Aromatic+Amide).

1H-NMR (DMSO-d6): δ 1.07 (t, 3H, CH2-CH3); 1.77 and 1.94 (2m, 4H, N—CH2-CH2-CH—); 1.84 (m, 2H, NH—CH2-CH2-CH2-); 2.45 (q, 2H, CH2-CH3); 2.75 (t, 2H, NH—CH2-CH2-CH2-); 2.85 (t, 1H, N—CH2-CH2-CH—); 2.98 and 3.53 (2m, 4H, N—CH2-CH2-CH—); 3.43 (m, 2H, N—CH2-CH2-CH2-); 3.61 and 3.85 (2m, 2H, NH—CH2-CH—NH); 4.32 (q, 1H, NH—CH—NH); 4.99 and 5.04 (syst AB, 2H, O—CH2-Ph); 6.67 (d, 1H, H naphthyridine); 7.22 (bs, 1H, NH—CH2-CH—NH); 7.35 (m, 5H, Ph); 7.60 (d, 1H, NH—CH2-CH—NH); 7.64 (d, 1H, H naphthyridine), 8.26 (s, 1H, N=CH—N); 8.29 ppm (bs, 1H, NH—CH2-CH2-CH2-).

HPLC/MS : (rt=8.0 min): 560 (MH+); 427 (MH-Naphthyridine+); 280 (M+2H++)

Microanalysis:
theoretical C=51.84% ; H=4.99% ; N=12.45%;
Found C=52.0%; H=5.2%; N=12.4%;

Example 2

3-[[5-ethyl-6-[4-[(1,2,3,4,5,6-hexahydro-2-pyrimidinyl)iminocarbonyl]-1-piperidinyl]-4-pyrimidinyl]amino]-N-[(phenylmethoxy)carbonyl]alanine

Stage a

Synthesis of (1,1-dimethylethyl)3-[[5-ethyl-6-[4-(methoxycarbonyl)-1-piperidinyl]-4-pyrimidinyl]amino]-N-[(phenylmethoxy)carbonyl]alaninate

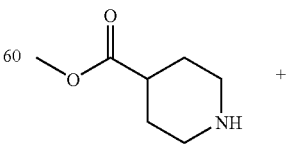
+

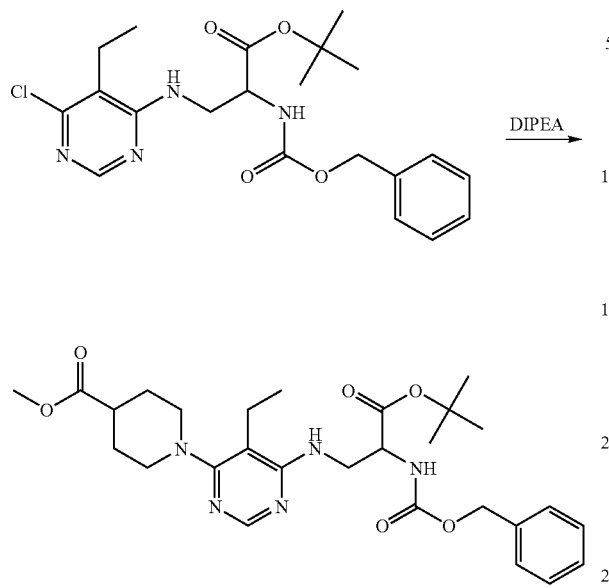

A mixture of 1.2 g (2.8 mmoles) of (1,1-dimethylethyl) 3-[(6-chloro-5-ethyl-4-pyrimidinyl)amino]-N-[(phenylmethoxy)carbonyl]alaninate, 5 ml of methyl 4-piperidinyl-carboxylate and 1 ml of isopropylethylamine is heated between 110 and 120° C. for 4 hours. After cooling down to ambient temperature, the reaction medium is taken up in ethyl acetate, water and a saturated solution of sodium bicarbonate. The organic phase is separated, dried over magnesium sulphate then concentrated to dryness under vacuum. The residue is chromatographed on silicagel with a gradient of pure heptane to pure ethyl acetate. 260 mg (Yield=17%) of expected product is obtained in the form of an oil.

TLC: Rf=0.36 (silicagel, eluent: heptane-ethyl acetate 50-50).

IR (CHCl$_3$): 3422 (NH); 1725 (C=O); 1582; 1499 cm-1 (Heterocycle+Aromatic+Amide)

1H-NMR (DMSO-d6): δ 1.05 (t, 3H, CH2-CH3); 1.30 (s, 9H, tBu); 1.67 and 1.88 (2m, 4H, N—CH2-CH2-CH); 2.40 (q, 2H, CH2-CH3); 2.50 (m, 1H, N—CH2-CH2-CH); 2.81 and 3.33 (2m, 4H, N—CH2-CH2-CH); 3.62 (s, 3H, O—CH3); 3.71 (m, 2H, NH—CH2-CH—NH); 4.22 (q, 1H, NH—CH2-CH—NH); 5.02 (s, 2H, O—CH2-Ph); 6.36 (t, 1H, NH—CH2-CH—NH); 7.34 (m, 5H, Ph); 7.64 (d, 1H, NH—CH2-CH—NH); 8.10 ppm (s, 1H, N=CH—N).

HPLC/MS : (rt=12 min): 564 (MNa+); 542 (MH+); 486 (MH-tBu+).

Stage b

Synthesis of 3-[[5-ethyl-6-[4-[(1,2,3,4,5,6-hexahydro-2-pyrimidinyl)iminocarbonyl]-1-piperidinyl]-4-pyrimidinyl]amino]-N-[(phenylmethoxy)carbonyl] alanine

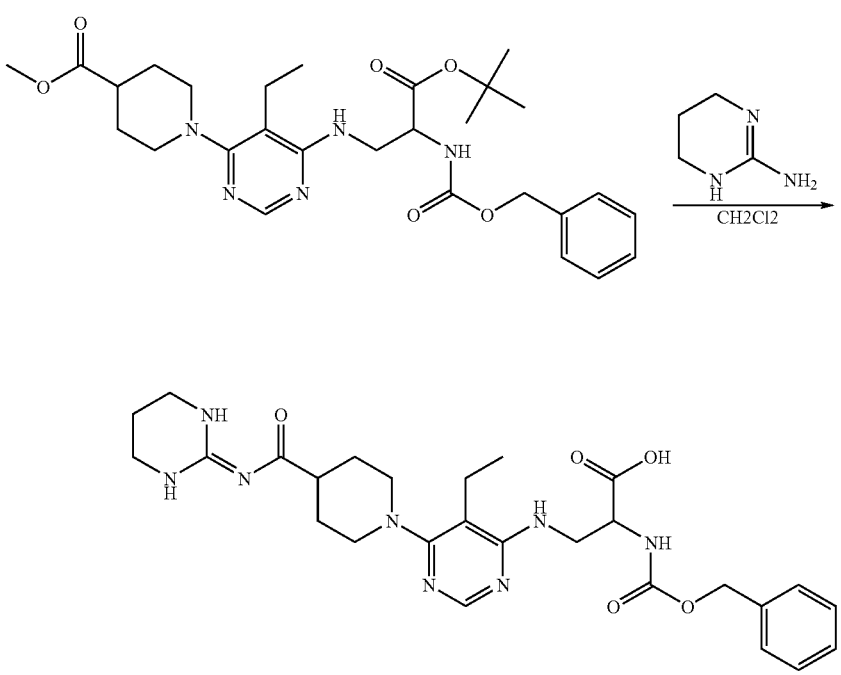

A mixture of 250 mg (0.46 mmoles) of 1,1-dimethylethyl) 3-[[5-ethyl-6-[4-(methoxycarbonyl)-1-piperidinyl]-4-pyrimidinyl]amino]-N-[(phenylmethoxy)carbonyl]alaninate and 200 mg (2.0 mmoles) of 2-amino-1,4,5,6-tetrahydropyrimidine (prepared according to R. F. Evans J. Chem. Soc. 1964, 2450-2455) in 15 ml of dichloromethane is stirred for 24 hours at ambient temperature. After evaporation to dryness under vacuum, the residue is chromatographed on silicagel eluting with a gradient of pure dichloromethane to a dichloromethane-methanol-water-acetic acid mixture 85-15-2-2. After evaporation of the solvent of useful fractions, the residue is taken up in the minimum amount of a mixture of methanol-dichloromethane 50-50 and the acid precipitates by the addition of ethyl ether. After filtration and drying under vacuum 18 mg (Yield=7%) of expected product is obtained in the form of an amorphous solid.

TLC: Rf=0.5 (silicagel, eluent: dichloromethane-methanol-acetic acid 70-20-10)

IR (CHCl$_3$): 3287 (OH/NH); 1700; 1600 (C=O); 1582; 1499 cm-1 (Heterocycle+Aromatic+Amide).

1H-NMR (DMSO-d6): δ 1.05 (t, 3H, CH2-CH3); 1.67 and 1.86 (2m, 4H, N—CH2-CH2-CH—); 1.80 (m, 2H, NH—CH2-CH2-CH2-NH); 2.26 (m, 1H, N—CH2-CH2-CH—); 2.38 (m, 2H, CH2-CH3); 2.78 and 3.33 (2m, 4H, N—CH2-CH2-CH—); 3.24 (m, 4H, NH—CH2-CH2-CH2-NH); 3.42 and 3.75 (2m, 2H, NH—CH2-CH—NH); 4.08 (m, 1H, NH—CH2-CH—NH); 4.95 and 5.00 (syst AB, 2H, O—CH2-Ph); 6.10 (bt, 1H, NH—CH2-CH—NH); 6.74 (bs, 1H, NH—CH2-CH—NH); 7.30 (m, 5H, Ph); 8.05 (s, 1H, N═CH—N); 8.55 ppm (bs, 2H, NH—CH2-CH2-CH2-NH).

HPLC/MS: (rt=6min): 553 (MH+); 364 (MH-tBu-PhCH2+); 320 (MH-tBu-Z+).

Example 3

3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alanine Stage a Synthesis of (1,1-dimethylethyl)3-[(6-chloro-5-methyl-4-pyrimidinyl)amino]-N-[(phenylmethoxy)carbonyl]alaninate

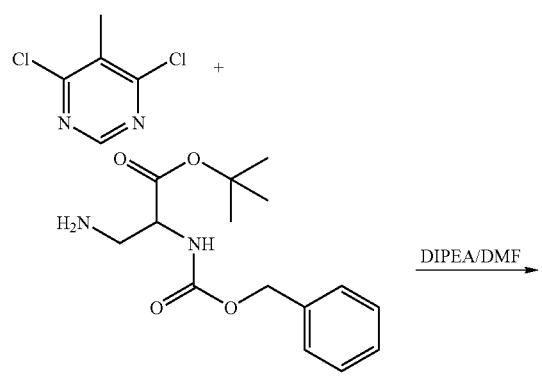

DIPEA/DMF

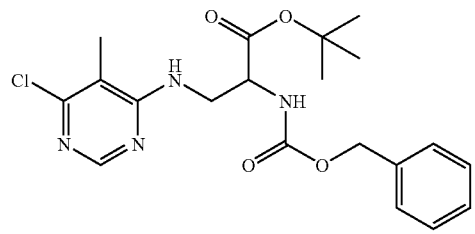

A mixture of 325 mg (2 mmoles) of 4,6-dichloro-5-methylpyrimidine (marketed by SPECS), 600 mg (2 mmoles) of (1,1-dimethylethyl) 3-amino-N-[(phenylmethoxy)carbonyl]alaninate (prepared according to J. Med. Chem. (2001), 44(8), 1158-1176) in 3 ml of dimethylformamide and 3 ml of diisopropylethylamine is heated at 120° C. overnight. The reaction medium is concentrated to dryness under vacuum and the residue is taken up in a mixture of water, ethyl acetate and a saturated solution of sodium bicarbonate. The organic phase is separated and the aqueous phase reextracted with ethyl acetate. The combined organic phases are dried over magnesium sulphate then the solvent is evaporated off under vacuum. The residue is chromatographed on silicagel eluting with a gradient of heptane (100%) to a mixture of heptane-ethyl acetate (50-50). 450 mg (Yield=53%) of expected product is obtained in the form of an oil.

TLC: Rf=0.5 (silicagel, eluent: ethyl acetate-heptane (25-75)

1H-NMR (CDCl3): δ 1.48 (s, 9H, tBu); 2.08 (s, 3H, CH3); 3.80 and 3.97 (2m, 2H, NH—CH2-CH—NH); 4.50 (m, 1H, NH—CH2-CH—NH); 5.08 and 5.15 (syst AB, 2H, O—CH2-Ph); 5.86 (bd, 1H, NH—CH2-CH—NH); 6.12 (bs, 1H, NH—CH2-CH—NH); 7.35 (m, 5H, Ph); 8.30 ppm (s, 1H, N═CH—N).

MS (FAB): 421 (MH+); 365 (MH-tBu).

Stage b

Synthesis of (1,1-dimethylethyl) 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alaninate

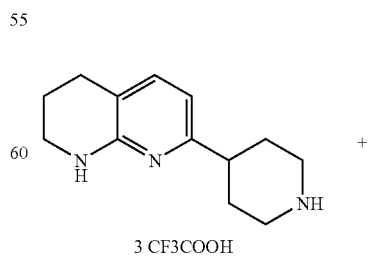

3 CF3COOH

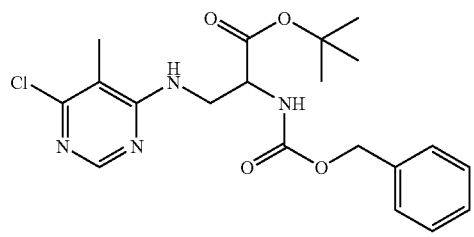

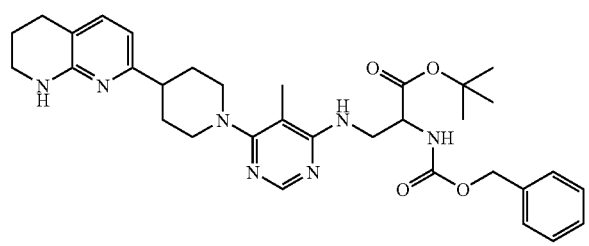

A mixture of 370 mg (0.88 mmoles) of (1,1-dimethylethyl) 3-[(6-chloro-5-methyl-4-pyrimidinyl)amino]-N-[(phenylmethoxy)carbonyl] alaninate and 1.0 g (1.79 mmoles) of 1,2,3,4-tetrahydro-7-(4-piperidinyl)-1,8-naphthyridine, tris(trifluoroacetate) (prepared according to Patents EP1065207 or WO 0078317) in 1 ml of diisopropylethylamine is heated at 120° C. for 2 hours. Then 10 ml of xylene is added and the medium is taken to reflux for 4 hours. The reaction medium is taken up in a mixture of water, ethyl acetate and a saturated solution of sodium bicarbonate. The organic phase is decanted and the aqueous phase is reextracted with ethyl acetate. The combined organic phases are dried over magnesium sulphate and evaporated to dryness under vacuum and the residue is chromatographed on silicagel with a gradient of 100% ethyl acetate to a mixture of ethyl acetate-methanol-triethylamine-dichloromethane 50-10-10-50. 32 mg (Yield=6%) of expected product is obtained and 200 mg (54%) of chlorinated starting product is recovered.

TLC: Rf=0.6 (silicagel, eluent: ethyl acetate-dichloromethane-methanol 50-40-10)

1H-NMR (CDCl$_3$): δ 1.49 (s, 9H, tBu); 1.97 (m, 2H, NH—CH2-CH2-CH2); 2.01 (s, 3H, CH3); 2.18 (m, 4H, N—CH2-CH2-CH); 2.79 (m, 2H, NH—CH2-CH2-CH2); 2.98 (m, 1H, N—CH2-CH2-CH); 3.39 and 3.89 (2m, 4H, N—CH2-CH2-CH); 3.52 (m, 2H, NH—CH2-CH2-CH2); 3.77 and 4.09 (2m, 2H, NH—CH2-CH—NH); 4.47 (m, 1H, NH—CH2-CH13 NH); 5.13 (bs, 2H, O—CH2-Ph); 5.92 (bs, 1H, NH—CH2-CH—NH); 6.47 (bd, 1H, H naphthyridine); 7.37 (m, 5H, Ph); 7.38 (m, 1H, H naphthyridine); 8.41; 8.68 and 14.80 ppm (3bs, 3H, N=CH—N and mobiles).

MS: 602 (MH+); 546 (MH-tBu+).

Stage c

Synthesis of 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alanine

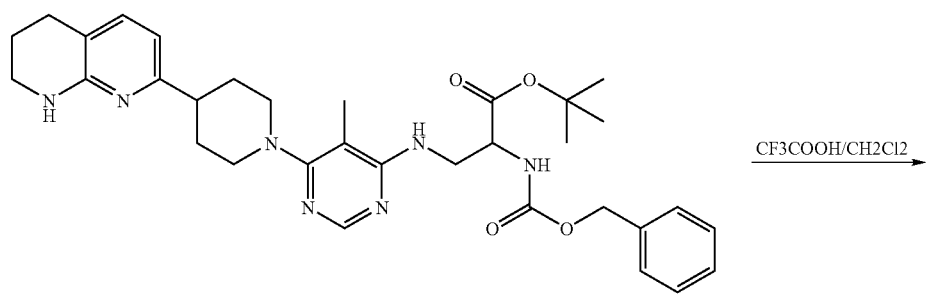

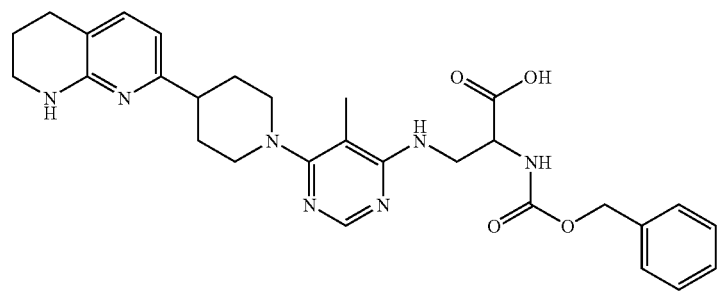

A mixture of 38 mg (0.06 mmoles) of (1,1-dimethylethyl) 3-[[6-[4-(1,2,3,4-tetrahydro-1,8-naphthyridin-7-yl)-1-piperidinyl]-5-methyl-4-pyrimidinyl]amino]-N-[(phenyl methoxy)carbonyl]alaninate and 2 ml of trifluoroacetic acid in 10 ml of dichloromethane is stirred at ambient temperature for 3 hours. Then 5 ml of toluene is added followed by evaporating the mixture to dryness. 26 mg (Yield=76%) of expected product is obtained in the form of an amorphous solid.

TLC: Rf=0.8 (silicagel, eluent: dichloromethane-methanol-water-acetic acid 90-10-1-1).

1H-NMR (DMSO-d6): δ 1.84 (m, 2H, NH—CH2-CH2-CH2); 1.92 (s, 3H, CH3); 1.75 and 1.91 (2m, 4H, N—CH2-CH2-CH); 2.74 (m, 2H, NH—CH2-CH2-CH2); 2.84 (m, 1H, N—CH2-CH2-CH); 2.92 and 3.67 (2m, 4H, N—CH2-CH2-CH); 3.44 (m, 2H, NH—CH2-CH2-CH2); 3.63 and 3.82 (2m, 2H, NH—CH2-CH—NH); 4.29 (m, 1H, NH—CH2-CH—NH); 5.02 (bs, 2H, O—CH2-Ph); 6.68 (d, 1H, H naphthyridine); 7.20 to 7.40 (m, 5H, Ph); 7.64 (bd, 1H, NH—CH2-CH—NH); 7.65 (d, 1H, H naphthyridine); 7.82 and 8.21 ppm (2bs, 3H, N═CH—N and mobiles).

HPLC/MS: (rt=7 min) 546 (MH+); 273 (M+2H++).

Example 4

3-[[6-[4-[(1,2,3,4,5,6-hexahydro-2-pyrimidinyl)iminocarbonyl]-1-piperidinyl]-5-methyl-4-pyrimidinyl]amino]-N-[(phenylmethoxy)carbonyl]alanine Stage a Synthesis of (1,1-dimethylethyl) 3-[[6-[4-(methoxycarbonyl)-1-piperidinyl]-5-methyl-4-pyrimidinyl]amino]-N-[(phenylmethoxy)carbonyl]alaninate

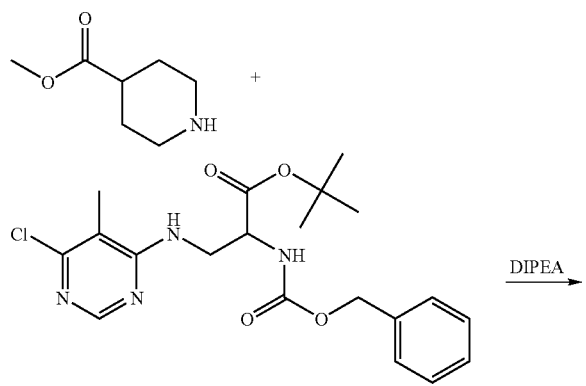

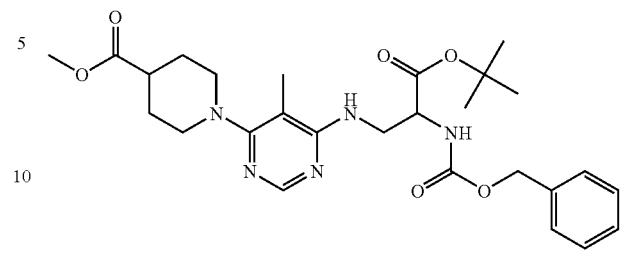

A mixture of 80 mg (0.19 mmoles) of (1,1-dimethylethyl) 3-[(6-chloro-5-methyl-4-pyrimidinyl)amino]-N-[(phenylmethoxy) carbonyl]alaninate and 3 ml of methyl 4-piperidinylcarboxylate is heated under reflux for 3 hours. After cooling down the reaction medium is taken up in water, ethyl acetate and a saturated solution of sodium bicarbonate. The organic phase is separated and the aqueous phase reextracted with ethyl acetate. The combined organic phases are dried over magnesium sulphate then the solvent eliminated under vacuum. The residue is chromatographed on silicagel eluting with a gradient of heptane (100%) to heptane-ethyl acetate (50-50). 25 mg (Yield=25%) of the expected product is obtained in the form of oil.

TLC: Rf=0.3 (silicagel, eluent: ethyl acetate-heptane 50-50)

IR (CHCl3): 3421(NH); 1724(C═O); 1585; 1501 cm-1 (C═C, C═N)

1H-NMR (DMSO-d6): δ 1.31 (s, 9H, tBu); 1.68 (bq, 2H, CH2-CH(C═O)); 1.87 (m, 2H, CH2-CH(C═O)); 1.87 (s, 3H, CH3-C═); 2.51 (masked, 1H, —CH2-CH—CH2-); 2.80 (bt, 2H, —N—(CH2)2-(CH2)2-); 3.44 (bd, 2H, —N—(CH2)2-(CH2)2-); 3.62 (s, 3H, CH3-O); 3.71 (m, 2H, NH—CH2-CH—NH—); 4.22 (m, 1H, NH—CH2-CH—NH—); 5.03 (bs, 2H, O—CH2-Ph); 6.35 bs, 1H, NH—CH2-CH—NH—); 7.34 (m, 5H, Ph); 7.63 (bd, 1H, NH—CH2-CH—NH—); 8.08 ppm (s, 1H, N═CH—N).

HPLC/MS: (rt=17min) 528 (MH+); 472 (MH-tBu+)

Stage b

Synthesis of 3-[[6-[4-[(1,2,3,4,5,6-hexahydro-2-pyrimidinyl)iminocarbonyl]-1-piperidinyl]-5-methyl-4-pyrimidinyl]amino]-N-[(phenylmethoxy)carbonyl]alanine

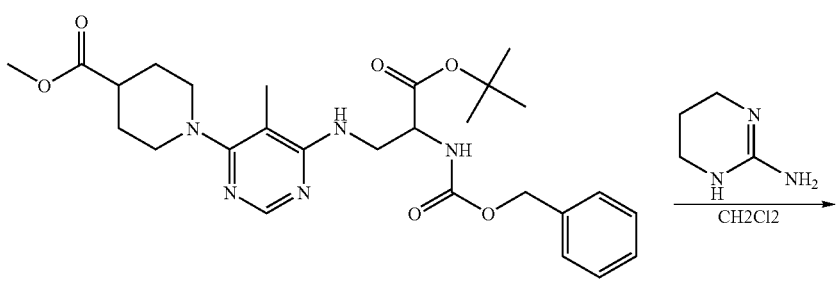

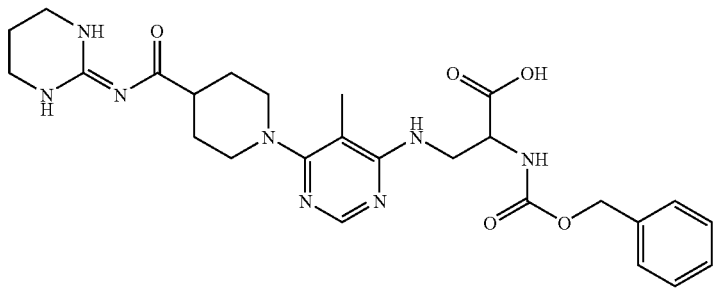

A mixture of 100 mg (0.19 mmoles) of (1,1-dimethylethyl) 3-[[6-[4-(methoxycarbonyl)-1-piperidinyl]-5-methyl-4-pyrimidinyl]amino]-N-[(phenylmethoxy) carbonyl]alaninate and 150 mg (1.5 mmoles) of 2-amino-1,4,5,6-tetrahydropyrimidine (prepared according to R. F. Evans J. Chem. Soc. 1964, 2450-2455) in 10 ml of dichloromethane is stirred at ambient temperature for 5 hours. The reaction medium is evaporated to dryness under vacuum and the residue is chromatographed on silicagel eluting with a dichloromethane-methanol-water-acetic acid mixture 85-15-2-2.

10 mg (Yield=10%) of expected product is obtained in the form of an amorphous solid.

TLC: Rf=0.4 (silicagel, eluent: dichloromethane-methanol-water-acetic acid 85-15-2-2)

1H-NMR (DMSO-d6): δ 1.64 and 1.74 (2m, 4H, N—CH2-CH2-CH); 1.77 (m, 2H, NH—CH2-CH2-CH2-NH); 1.85 (s, 3H, CH3); 2.11 (m, 1H, N—CH2-CH2-CH); 3.17 (m, 4H, NH—CH2-CH2-CH2-NH); 2.68 and 3.42 (2m, 4H, N—CH2-CH2-CH); 3.30 and 3.62 (2m, 2H, HN—CH2-CH—NH); 3.73 (m, 1H, N—CH2-CH—NH); 5.00 (m, 2H, O—CH2-Ph); 6.54 (bd, 1H, NH—CH2-CH—NH); 6.77 (bs, 1H, NH—CH2-CH—NH); 7.33 (m, 5H, Ph); 8.04 ppm (s, 1H, N=CH—N).

HPLC/MS: (rt=1.9 min) 1077 (2MH+); 539 (MH+); 440 (MH-aminotetrahydro pyrimidine+)

Example 5 ethyl 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate, dihydrochloride

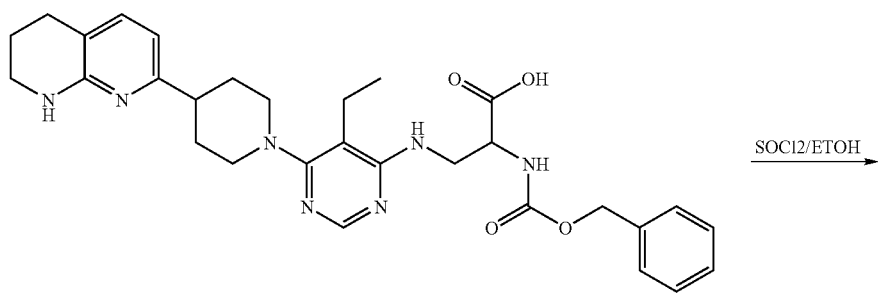

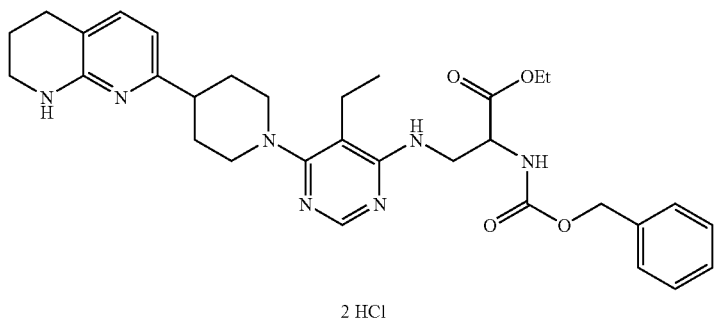

160 μl (2.19 mmoles) of thionyl chloride is added to 4 ml of ethanol cooled down to −12° C. under a nitrogen atmosphere and the mixture is stirred for 30 minutes. Then a solution of 354 mg (0.45 mmoles) of 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis(trifluoroacetate) in 13 ml of ethanol is added. The mixture is stirred for 30 minutes at −12° C. then left to return to ambient temperature and finally heated at 40° C. for 4 hours under nitrogen. The reaction medium is evaporated to dryness under vacuum and the residue crystallizes from a mixture of diisopropyl ether and of pentane and the solid is filtered. 284 mg (Yield=95%) of expected product is obtained in the form of an amorphous beige solid.

TLC: Rf=0.4 (silicagel, eluent: dichloromethane-methanol-water-acetic acid 90-10-1-1)

IR (CHCl$_3$): 3400-3000(OH, NH); 1719(C=O); 1654; 1623; 1580; 1504 cm-1 (C=C, C=N, aromatic)

1H-NMR (DMSO-d6): δ 1.09 (t, 3H, CH2-CH3); 1.14 (t, 3H, O—CH2-CH3); 1.85 (m, 2H, NH—CH2-CH2-CH2); 1.85 and 2.00 (2m, 4H, N—CH2-CH2-CH); 2.48 (m, 2H, CH2-CH3); 2.75 (t, 2H, NH—CH2-CH2-CH2); 2.92 (m, 1H, N—CH2-CH2-CH); 3.03 and 3.57 (2m, 4H, N—CH2-CH2-CH); 3.44 (t, 2H, N—CH2-CH2-CH2); 3.76 and 3.87 (2m, 2H, NH—CH2-CH—NH); 4.07 (q, 2H, O—CH2-CH3); 4.39 (q, 1H, NH—CH2-CH—NH); 5.03 (s, 2H, O—CH2-Ph); 6.62 (d, 1H, H naphthyridine); 6.86 (bs, 1H, NH—CH2-CH—NH); 7.30 (m, 5H, Ph); 7.33 (bs, 1H, NH—CH2-CH—NH); 7.58 (d, 1H, H naphthyridine); 8.20 ppm (s, 1H, N=CH—N).

HPLC/MS: (rt=6.2 min) 588 (MH+); 454 (MH-COOCH2Ph+); 437 (MH-NHCOOCH2Ph+).

Example 6

Synthesis of 4,6-dihydroxy-5-methyl-pyrimidine

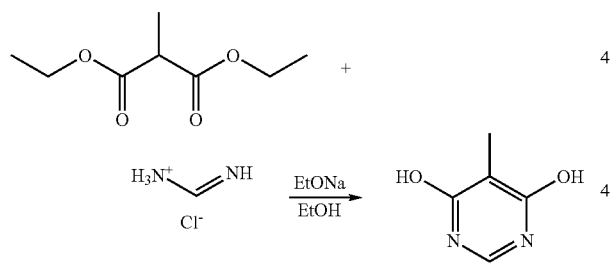

102 ml (282 mmoles) of a solution of sodium ethylate at 21% in ethanol is added to a solution of 7.5 g (94 mmoles) of formamidine hydrochloride in 250 ml of ethanol cooled down to 0° C. and the mixture is stirred for 30 minutes; then a solution of 13 ml (94 mmoles) of diethyl methyl malonate in 50 ml of ethanol is added followed by stirring overnight at ambient temperature. The reaction mixture is evaporated to dryness under reduced pressure (2 kPa) and the residue is taken up in ethyl acetate, water and acetic acid in order to adjust the pH to 6. The precipitate is filtered then washed successively with water, isopropanol, diethyl ether and finally with pentane. 7 g (Yield=60%) of expected product is obtained in the form of a beige solid.

TLC: Rf=0.20 (silicagel, eluent: ethyl acetate-dichloromethane-methanol 50-40-10)

1H-NMR (DMSO d6): ppm 1.73 (s, 3H, C—CH$_3$); 7.88 (s, N=CH—N).

MS: 127 (MH+); 125 (M-H-).

Synthesis of 4,6-dibromo-5-methyl-pyrimidine

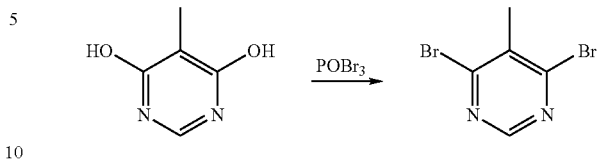

A mixture of 6 g (47.6 mmoles) of 5-methyl-4,6-dihydroxy-pyrimidine in 18 g of phosphorus oxybromide is taken to 200° C. for 3 hours. After returning to ambient temperature, the reaction mixture is taken up in a mixture of iced water and sodium bicarbonate and extraction is carried out with ethyl acetate, followed by washing the organic phases with water, drying over magnesium sulphate and evaporating to dryness under reduced pressure (2 kPa). 9 g (Yield=75%) of a beige solid is obtained.

TLC: Rf=0.27 (silicagel, eluent: dichloromethane-pentane 50-50)

1H-NMR (CDCl3): ppm 2.58 (s, 3H, C—CH$_3$); 8.51 (s, N=CH—N).

MS: 253-255 (MH+).

Synthesis of 6-[4-(1,2,3,4-tetrahydro-1,8-naphthyridin-7-yl)-1-piperidinyl]-5-methyl-4-bromo-pyrimidine:

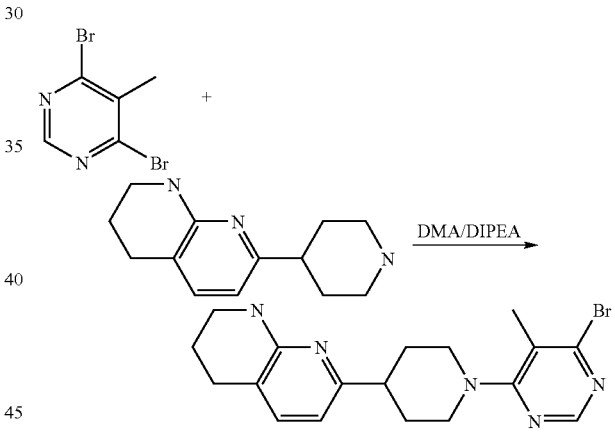

70 ml dimethylacetamide, 7.56 g (30 mmoles) of 4,6-dibromo-5-methylpyrimidine in solution in 40 ml of dimethylacetamide and 14 ml of diisopropylethylamine are added into a single-necked flask containing 8 g (36.8 mmoles) of 4-(1,2,3,4-tetrahydro-1,8-naphthyridin-7-yl)-1-piperidine released from its salt. This mixture is heated at 140° C. for 4 hours then concentrated to dryness under reduced pressure (2 kPa). The residue obtained is taken up in a mixture of water, ethyl acetate and a saturated solution of sodium bicarbonate. The organic phase is separated and the aqueous phase reextracted with ethyl acetate. The combined organic phases are dried over magnesium sulphate then the solvent is evaporated off under reduced pressure (2 kPa). The solid obtained is washed several times with diisopropyl ether then with pentane, 7.7 g of the expected product is obtained in the form of a light brown powder. The filtrate is concentrated to dryness then chromatographed on silicagel eluting with a gradient of ethyl acetate (100%) then ethyl acetate-methanol (95-5). 533 mg of expected product is obtained in the form of a yellow powder. (Overall yield=70%)

Preparation of naphthyridine in free amine form:

22 g of naphthyridine is displaced from its salt by 6 mass equivalents of basic amberlyst A21 resin (resin of R-NMe$_2$ type) in a CH$_2$Cl$_2$/MeOH/AcOEt mixture 1/1/1 under stirring for 30 minutes. The resin is washed beforehand and left to swell for 20 minutes in this solvent mixture. This operation must be repeated 3 times for the displacement of the salt to be complete. After filtration of the resin and evaporation of the solvents, 8 g (36.8 mmoles) of free naphthyridine is obtained.

TLC: Rf-0.33 (silicagel, eluent: ethyl acetate (100%)).

1H-NMR (DMSO-d6): δ 1.7 to 1.85 (m, 6H, NH—CH2-CH2-CH2, N—CH2-CH2-CH—CH2); 2.23 (s, 3H, CH3-); 2.60 (m, 3H, CH2-CH—CH2, NH—CH2-CH2-CH2); 3.23 (m, 2H, NH—CH2-CH2-CH2); 2.97 and 3.92 (2m, 4H, CH2-CH2-N—CH2-CH2); 6.3 and 7.05 (2d, 2H, CH=CH naphthyridine); 8.28 (s, 1H, N=CH—N).

MS (FAB): 388(M); 389(MH+)

Synthesis of (1,1-dimethylethyl) 3-[[5-methyl-6-[4-(1,2,3,4-tetrahydro-1,8-naphthyridin-7-yl)-1-piperidinyl]-4-pyrimidinyl]amino]-N-[(phenylmethoxy)carbonyl]alaninate.

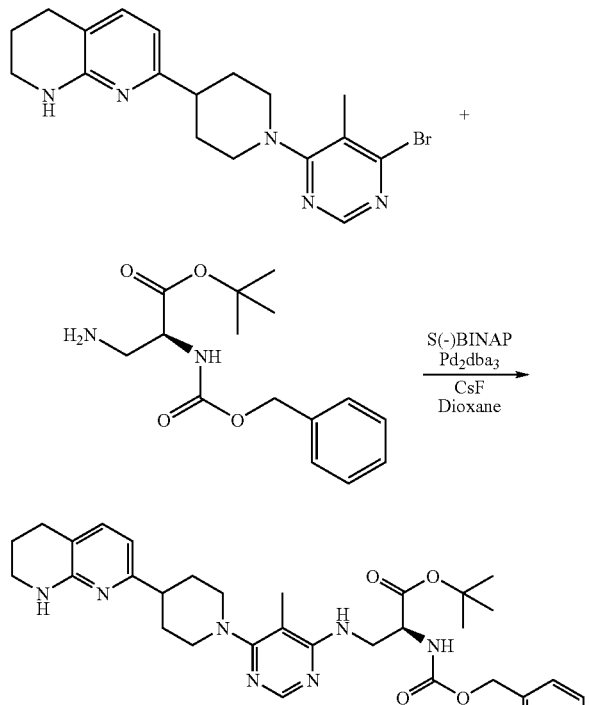

A mixture of 620 mg (1.6 mmoles) of 4-bromo-5-methyl-6-[4-(1,2,3,4-tetrahydro-1,8-naphthyridin-7-yl)-1-piperidinyl]-pyrimidine, 565 mg (1.92 mmoles) of (1,1-dimethylethyl)3-amino-N-[(phenylmethoxy)carbonyl]alaninate (prepared according to J. Med. Chem.(2001), 44(8), 1158-1176), 340 mg (2.25 mmoles) of caesium fluoride, 73 mg (0.08 mmoles) of tris(dibenzylideneacetone) dipalladium(0), 100 mg (0.16 mmoles) of S(−)2,2'-bis(diphenyl-phosphino)-1,1'-binaphthyl in 50 ml of dioxane is heated under reflux for 5 hours. After cooling down another 280 mg (0.96 mmoles) of (1,1-dimethylethyl)3-amino-N-[(phenylmethoxy)carbonyl] alaninate, 340 mg (2.25 mmoles) of caesium fluoride, 73 mg (0.08 mmoles) of tris(dibenzylideneacetone) dipalladium(0), and 100 mg (0.16 mmoles) of S(−)2,2'-bis(diphenyl-phosphino)-1,1'-binaphthyl are then added and the reaction mixture is heated under reflux for 5 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed a first time on silicagel eluting with a gradient of ethyl acetate-methylene chloride-triethylamine-methanol from 50-50-0-0 to 50-50-2-2. The product obtained is chromatographed a second time on alumina eluting with a mixture of heptane-methylene chloride 50-50 then with ethyl acetate-diisopropyl ether 50-50. 360 mg (Yield=37%) of expected product is obtained in the form of an amorphous white solid.

TLC: Rf=0.20 (silicagel, eluent: methylene chloride-methanol 95-5).

IR (CHCl3): 3435 (NH); 1717 (C=O); 1583.1555.1501 cm-1 (Heterocycle+Aromatic+Amide).

1H-NMR (CDCl3): δ 1.47 (s, 9H, tBu); 1.94 (s, 3H, C—CH$_3$); 1.75 to 2.05 (m, 6H, CH$_2$—CH$_2$—CH$_2$—NH and CH$_2$—CH—CH$_2$); 2.60 to 2.77 (m, 3H, CH$_2$—CH—CH$_2$ and CH$_2$—CH$_2$—CH$_2$—NH); 2.93 and 3.90 (2m, 4H, CH$_2$—CH$_2$—N—CH$_2$—CH$_2$); 3.42 (m, 2H, CH$_2$—CH$_2$—CH$_2$—NH); 3.66 (m, 2H, NH—CH$_2$—CH—NH); 4.45 (m, 1H, NH—CH$_2$—CH—NH); 4.95, 5.25 and 6.20 (3m, 3H CH$_2$—CH$_2$—CH$_2$—NH  NH—CH$_2$—CH—NH, NH—CH$_2$—CH—NH); 5.12 (s, 2H, CH$_2$-Ph); 7.35 (m, 5H, Ph); 8.29 ppm (s, N=CH—N).

MS: 602 (MH+); 546 (MH-tBu+); 412 (MH-COOCH2Ph+).

[α$_D$] (0.625% EtOH): −4.5°

Synthesis of 3-[[5-methyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis(trifluoroacetate).

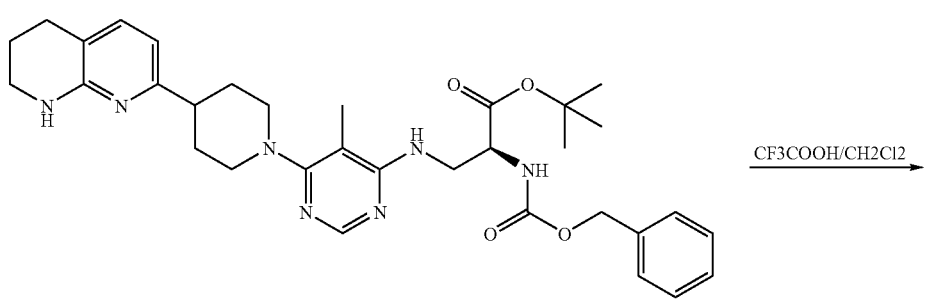

-continued

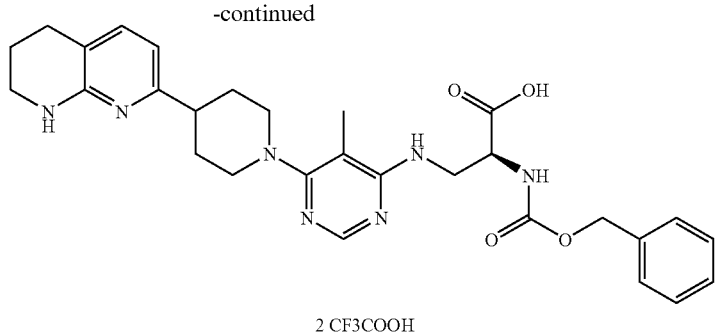

2 CF3COOH 350 mg (0.58 mmoles) of (1,1-dimethylethyl) 3-[[5-methyl-6-[4-(1,2,3,4-tetrahydro-1,8-naphthyridin-7-yl)-1-piperidinyl]-4-pyrimidinyl]amino]-N-[(phenylmethoxy)carbonyl]alaninate in 15 ml of dichloromethane is stirred with 3 ml of trifluoroacetic acid at ambient temperature until the starting product disappears according to TLC (silicagel, eluent: CH2Cl2-MeOH-H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 330 mg (Yield=73% expressed as ditrifluoroacetate) of expected product is obtained in the form of a white solid.

TLC: Rf=0.44 (silicagel, eluent: dichloromethane-methanol-water-acetic acid 90-10-1-1)

1H-NMR (CDCl3): δ 1.96 (s, 3H, C—$\underline{CH_3}$); 1.80 to 2.05 (m, 6H, $CH_2$—$CH_2$—$CH_2$—NH and $\overline{CH_2}$—CH—$CH_2$); 2.76 (t, 2H, NH—$\overline{CH2}$-CH2-$\underline{CH2}$-); 2.96 (t, 1H, N—$\overline{CH2}$-CH2-$\underline{CH}$—); 3.21 and 3.83 (2m, 4H, N—$\underline{CH2}$-CH2-CH—); 3.50 (m, 2H, N—$\underline{CH2}$-CH2-CH2-); 3.83 and 4.05 (2m, 2H, NH—$\underline{CH2}$-CH—NH); 4.54 (q, 1H, NH—CH2-$\underline{CH}$—NH); 5.50 (s, 2H, O—$\underline{CH2}$-Ph); 6.40 (d, 1H, H naphthyridine); 6.55 (bd, 1H, $\underline{NH}$); 7.28 (m, 5H, Ph); 7.45 (ml, 1H, $\underline{NH}$); 8.22 (d, 1H, H naphthyridine), 8.22 (s, 1H, N=$\underline{CH}$—N); 9.62 ppm (bs, 1H).

MS: 546 (MH+); 412 (MH-COOCH2Ph+); 544- (M-H-); 436- (544-OCH2Ph-); 1089- (2M-H-)

[α$_D$] (0.60% MeOH): −14.0.

Example 7

Preparation of Naphthyridine in Free Amine Form 22 g of naphthyridine is displaced from its salt by 6 mass equivalents of basic amberlyst A21 resin (resin of R-NMe$_2$ type) in a CH$_2$Cl$_2$/MeOH /AcOEt mixture 1/1/1 under stirring for 30 minutes. The resin is washed beforehand and left to swell for 20 minutes in this solvent mixture. This operation must be repeated 3 times for displacement of the salt to be complete. After filtration of the resin and evaporation of the solvents, 8 g (36.8 mmoles) of free naphthyridine is obtained.

TLC: Rf=0.33 [silicagel, eluent: ethyl acetate (100%)]

1H-NMR (DMSO-d6): δ 1.7 to 1.85 (m, 6H, NH—CH2-$\underline{CH2}$-CH2, N—CH2-$\underline{CH2}$-CH—$\underline{CH2}$); 2.23 (s, 3H, CH3-); 2.60 (m, 3H, CH2-$\underline{CH}$—CH2, NH—CH2-CH2-$\underline{CH2}$); 3.23 (m, 2H, NH—CH2-CH2-$\underline{CH2}$); 2.97 and 3.92 (2m, 4H, CH2-$\underline{CH2}$-N—$\underline{CH2}$-CH2); 6.3 and 7.05 (2d, 2H, $\underline{CH}$=$\underline{CH}$ naphthyridine); 8.28 (s, 1H, N=$\underline{CH}$—N).

MS (FAB): (rt=0.50 min and 2.80 min): 388(M); 389(MH+)

Synthesis of ethyl N-(alpha)-Z-L,2-3-diaminopropionate.

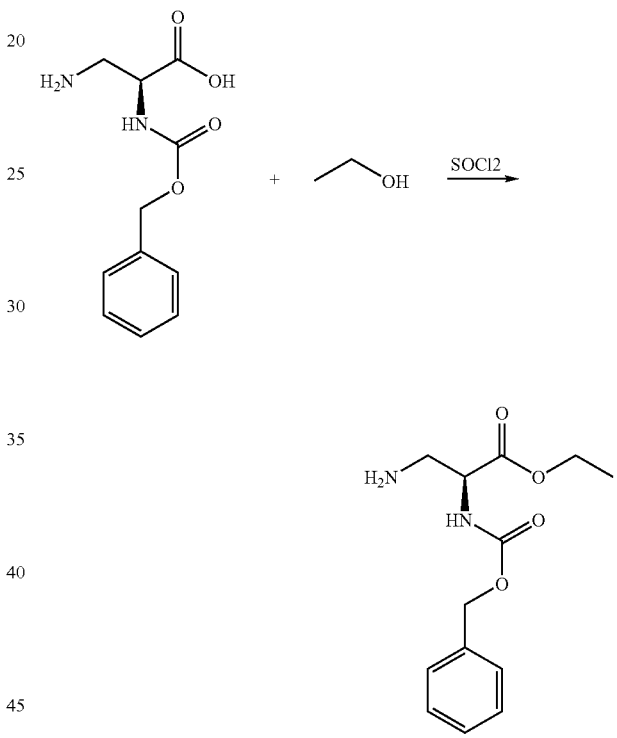

12 ml (168 mmoles) of thionyl chloride is added dropwise and at 0° C. into a single-necked flask containing 26 ml of absolute ethanol. This mixture is stirred for about twenty minutes at AT then 2 g (8.4 mmoles) of N-(alpha)-Z-L,2-3-diamino-propionic acid is added to it in small quantities, a white cloudiness appears.

The reaction mixture is then taken to reflux (78° C.) for 2 hours (after heating for a few minutes, the solution becomes clear).

After cooling down the solution is concentrated to dryness, a yellow liquid is obtained to which isopropyl ether is added. The expected product solidifies, then the supernatant is removed and the residue is taken up in a mixture of water, ethyl acetate and a saturated solution of sodium bicarbonate. The organic phase is separated and the aqueous phase is again extracted with ethyl acetate. The combined organic phases are dried over magnesium sulphate then the solvent is evaporated off under vacuum. 1.4 g of a pale yellow oil is obtained, it is the ester in free amine form (Yield=63%).

TLC: Rf =0.41 [Silicagel, eluent: methylene chloride-methanol (85-15)and 2% of water-acetic acid (1-1).

1H-NMR (CDCl3): 1.33 (t, 3H, CH3-CH2-O); 2.53 (m, 2H, NH2-CH2-CH) 3.15 (m, 2H, NH2-CH2-CH); 4.22 (q, 2H, CH3-CH2-O); 4.42 (m, 1H, NH2-CH2-CH—NH); 5.85 (m, 1H, CH—NH—CO); 5.15 (s, 2H, O—CH2-Ph); 7.35 (m, 5H, Ph)

MS (FAB): (rt=0.51 min and 1.2 min): 267(MH+); 533 (2MH+)

[α]$_D$ (CHCl3)=+6.336

Synthesis of ethyl 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alaninate.

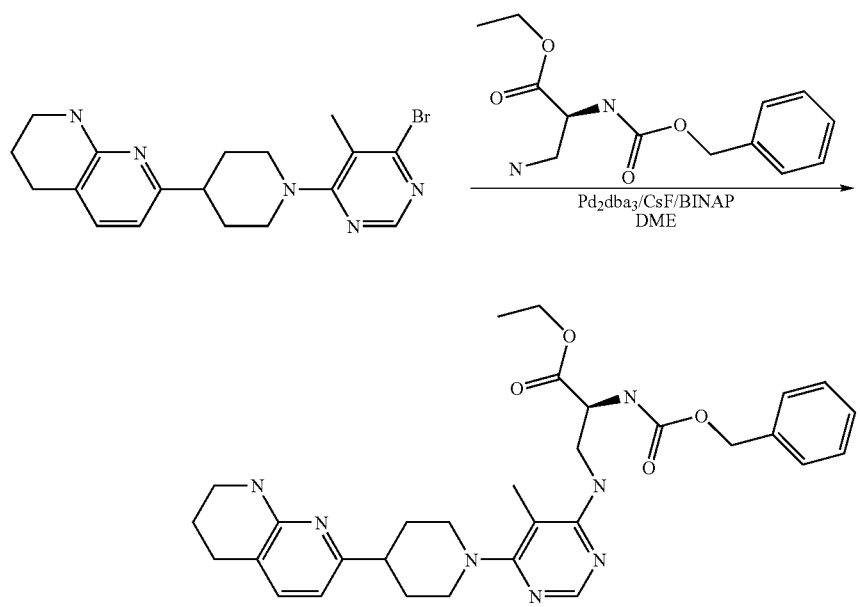

A mixture of 1.9 g (4.9 mmoles) of 6-[4-(1,2,3,4-tetrahydro-1,8-naphthyridin-7-yl)-1-piperidinyl]-5-methyl-4-bromo-pyrimidine and 1.62 g (6.08. mmoles) of ethyl 3-amino-N-[(phenylmethoxy)carbonyl]alaninate, is heated under reflux for 4 hours in the presence of 1.06 g (6.86 mmoles) of caesium fluoride, 310 mg (490 pmoles)of (2,2'-bis(diphenylphosphino)-1,1'-binaphthyl and 230 mg (245 μmoles) of tris(dibenzylideneacetone) dipalladium(o) in 40 ml of 1,2-dimethoxyethane. The reaction mixture is then taken to temperature for the addition of 230 mg (245 μmoles) of tris(dibenzylideneacetone)dipalladium(o), then again taken to reflux for 16 hours.

After cooling down the solution is concentrated to dryness then taken up in a mixture of water, ethyl acetate and a saturated solution of sodium bicarbonate. The organic phase is decanted and the aqueous phase is extracted with ethyl acetate. The combined organic phases are dried over magnesium sulphate and evaporated to dryness under vacuum. The residue is chromatographed on silicagel with 100% ethyl acetate. 1.15 g of expected product is obtained in the form of a pale yellow oil (yield=40%)

TLC: Rf=0.16 (silicagel eluent: 100% ethyl acetate

1H-NMR (CDCl3): δ 1.25 (t, 3H, CH3-CH2-O); 1.80 to 2.05 (m, 9H, NH—CH2-CH2-CH2, N—CH2-CH2-CH— CH2,CH3-C═C—); 2.72 (m, 3H, CH2-C—CH2, NH—CH2-CH2-CH2); 2.95 and 3.93 (2m, 4H, CH2-CH2-N—CH2-CH2); 3.45 (m, 2H, NH—CH2-CH2-CH2); 3.68 (d, 2H, NH—CH2-CH—NH) 4.23 (t, 2H, CH3-CH2-O), 4.45 (m, 1H, NH—CH2-CH—NH); 5.10 and 5.17 (syst AB, 2H, O—CH2-Ph); −6.41 and 7.18 (2d, 2H, CH═CH naphthyridine); 7.35 (m, 5H, Ph); 8.27 (s, 1H, N═CH—N).

HPLC/MS: (rt=0.48 min and 2.9 min): 574 (MH+); 440 [MH-Z+]; 287 [MH-(tBu-Z+)]

[α]$_D$ (CHCl3)=+0.788

Formation of the hydrochloride:

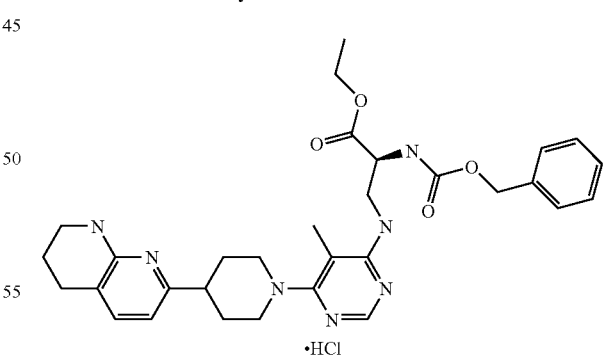

1.15 g of ethyl 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alaninate are solubilized in a minimum amount of methylene chloride. This solution is poured into ethyl ether, the solution must remain clear. Then, 2.65 ml of 2N HCl diluted in a little ethyl ether is added dropwise, under stirring. The hydrochloride solidifies, the supernatant is removed, then the residue crystallizes from isopropyl ether. Then a solid is obtained which is filtered, rinsed with ether then with pentane. After drying, 890 mg of a pale yellow powder is obtained. (Yield=73%)

Example 8

Preparation of Naphthyridine in Free Amine Form 22 g of naphthyridine is displaced from its salt by 6 mass equivalents of basic amberlyst A21 resin (resin of R—NMe$_2$ type) in a CH$_2$Cl$_2$/MeOH/AcOEt mixture 1/1/1 under stirring for 30 minutes. The resin is washed beforehand and left to swell for 20 minutes in this solvent mixture. This operation must be repeated 3 times for the displacement of the salt to be complete. After filtration of the resin and evaporation of the solvents, 8 g (36.8 mmoles) of free naphthyridine is obtained.

TLC: Rf=0.33 [silicagel, eluent: ethyl acetate (100%)]

1H-NMR (DMSO-d6): δ 1.7 to 1.85 (m, 6H, NH—CH2-CH2-CH2, N—CH2-CH2-CH—CH2); 2.23 (s, 3H, CH3-); 2.60 (m, 3H, CH2-CH—CH2, NH—CH2-CH2-CH2); 3.23 (m, 2H, NH—CH2-CH2-CH2); 2.97 and 3.92 (2m, 4H, CH2-CH2-N—CH2-CH2); 6.3 and 7.05 (2d, 2H, CH=CH naphthyridine); 8.28 (s, 1H, N=CH—N).

MS (FAB): (rt=0.50 min and 2.80 min): 388(M); 389(MH+)

Synthesis of isopropyl N-(alpha)-Z-L,2-3-diaminopropionate.

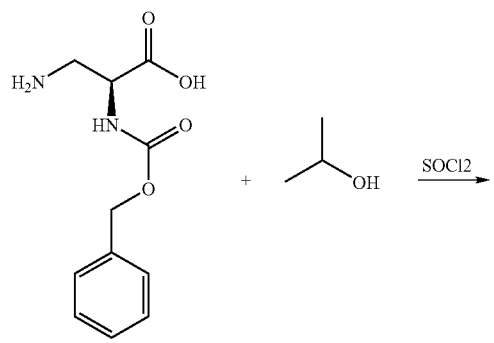

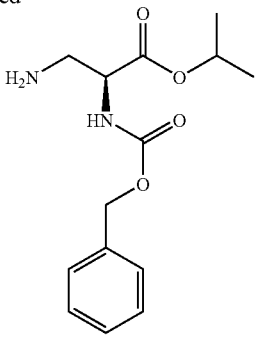

46 ml (840 mmoles) of thionyl chloride is added dropwise and at 0° C. into a single-necked flask containing 125 ml of isopropanol. This mixture is stirred for about twenty minutes at AT then 10 g (42 mmoles) of N-(alpha)-Z-L,2-3-diaminopropionic acid is added to it in small quantities, a white cloudiness appears.

The reaction mixture is then taken to reflux (78° C.) for 2 hours (after a heating for a few minutes, the solution becomes clear).

After cooling down the solution is concentrated to dryness, a yellow liquid is obtained to which isopropyl ether is added. The expected product solidifies, then the supernatant is removed and the residue is taken up in a mixture of water, ethyl acetate and a saturated solution of sodium bicarbonate. The organic phase is separated and the aqueous phase is again extracted with ethyl acetate. The combined organic phases are dried over magnesium sulphate then the solvent is evaporated off under vacuum. 7.4 g of a white powder is obtained, it is the ester in free amine form (Yield=42%).

TLC: Rf=0.5 [Silicagel, eluent: methylene chloride-methanol (85-15)and 2% of water-acetic acid (1-1).

1H-NMR (CDCl3): δ 1.25 (d, 6H, CH3-CH—CH3); 1.60 (m, 2H, NH2-CH2-CH) 3.10 (m, 2H, NH2-CH2-CH); 4.35 (m, 1H, NH2-CH2-CH—NH) 5.10 (m, 1H, CH3-CH—CH3); 5.15 (s, 2H, O—CH2-Ph); 5.2 (m, 1H, CH—NH—CO), 7.37 (m, 5H, Ph)

MS (FAB): (rt=0.52 min and 2.09 min): 281(MH+); 239 (MH-ipr+)

[α]$_D$ (CHCl3)=+15.02

Synthesis of isopropyl 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alaninate.

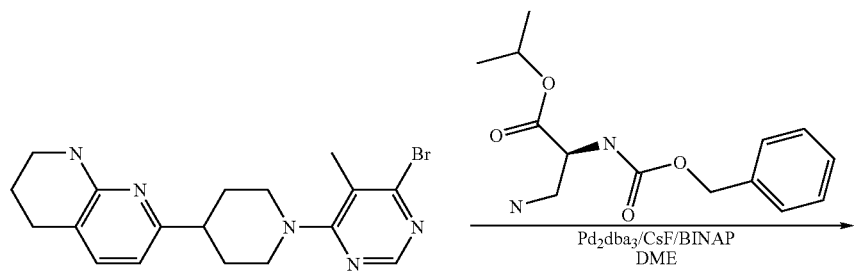

-continued

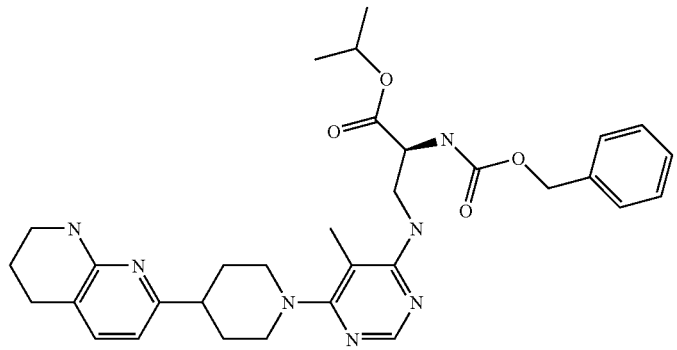

A mixture of 1.5 g (3.86 mmoles) of 6-[4-(1,2,3,4-tetrahydro-1,8-naphthyridin-7-yl)-1-piperidinyl]-5-methyl-4-bromo-pyrimidine and 1.30 g (4.63 mmoles) of isopropyl 3-amino-N-[(phenylmethoxy)carbonyl]alaninate, is heated under reflux for 5 hours and 30 minutes in the presence of 825 mg (5.41 mmoles) of caesium fluoride, 241 mg (386 μmoles) of (2,2'-bis(diphenylphosphino)-1,1'-binaphthyl and 180 mg (193 μmoles) of tris(dibenzylideneacetone) dipalladium(o) in 40 ml of 1,2-dimethoxyethane. The reaction mixture is then taken to temperature for the addition of 180 mg (245 μmoles) of tris(dibenzylideneacetone) dipalladium(o), then again taken to reflux for 16 hours.

The next day, the reaction mixture is heated for another 9 hours after having added 180 mg (193 μmoles) of tris(dibenzylideneacetone) dipalladium(o. After cooling down the solution is concentrated to dryness then taken up in a mixture of water, ethyl acetate and a saturated solution of sodium bicarbonate. The organic phase is decanted and the aqueous phase is extracted with ethyl acetate. The combined organic phases are dried over magnesium sulphate and evaporated to dryness under vacuum. The residue is chromatographed on silicagel with 100% ethyl acetate. 1.52 g of expected product is obtained in the form of crystals yellow pale (yield=50%)

TLC: Rf=0.18 (silicagel eluent: 100% ethyl acetate

1H-NMR (CDCl3): δ 1.27 (d, 6H, CH3-CH—CH3); 1.83 to 2.05 (m, 9H, NH—CH2-CH2-CH2, N—CH2-CH2-CH—CH2, CH3-C═C—); 2.72 (m, 3H, CH2-CH—CH2, NH—CH2-CH2-CH2); 2.95 and 3.93 (2m, 4H, CH2-CH2-N—CH2-CH2); 3.45 (m, 2H, NH—CH2-CH2-CH2); 3.68 (d, 2H, NH—CH2-CH—NH), 4.50 (m, 1H, NH—CH2-CH—NH); 5.07 (m, 1H, CH3-CH—CH3); 5.12 (s, 2H, O—CH2-Ph); 6.42 and 7.18 (2d, 2H, CH═CH naphthyridine); 7.35 (m, 5H, Ph); 8.28 (s, 1H, N═CH—N).

HPLC/MS : (rt=0.48 min and 3.03 min): 588 (MH+); 454 [MH-Z+]; 412 [MH-(ipr-Z)+]

[α]_D (CHCl3)=+0.7655

Formation of the hydrochloride:

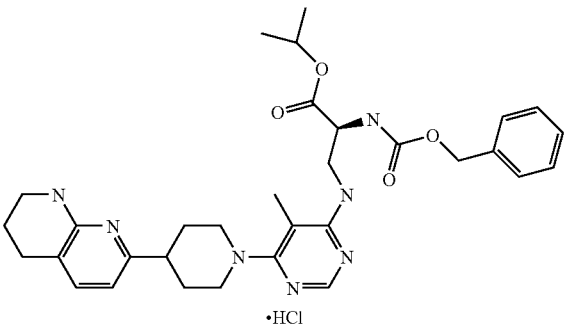

3.8 g of isopropyl 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alaninate is solubilized in 20 ml of methylene chloride. This solution is poured into ethyl ether, the solution must remain clear. Then, 3.23 ml of 2N HCl diluted in a little ethyl ether is added dropwise, under stirring. The hydrochloride solidifies, the supernatant is removed, then the residue is crystallized from isopropyl ether. Then a solid is obtained which is filtered, rinsed with ether then with pentane. After drying, 3.44 g of a white powder is obtained. (Yield=85%)

Example 9

Synthesis of 4,6-dibromo-5-ethyl-pyrimidine

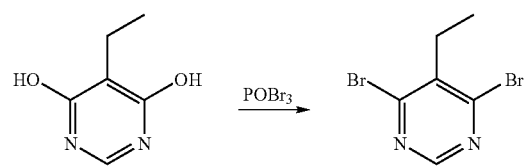

A mixture of 2.8 g (20 mmoles) of 5-ethyl-4,6-dihydroxy-pyrimidine (marketed by Aldrich) and 8.85 g (31 mmoles) of phosphorus oxybromide is taken to 160° C. for 1 hour. After returning to ambient temperature, the reaction mixture is poured into a mixture of ice, a saturated solution of sodium bicarbonate and ethyl acetate. After decanting, the organic phase is washed with a saturated solution of sodium bicarbonate, followed by drying over magnesium sulphate and the solvent is eliminated by evaporation under reduced pressure (2 kPa). The residue is chromatographed on silicagel eluting with a gradient of 100% heptane to heptane-ethyl acetate 50-50. 3.92 g (Yield=74%) of a light brown solid of expected product is obtained which is used as it is for the following.

TLC: Rf0.5 (silicagel, eluent: heptane-ethyl acetate 90-10)

IR (CHCl$_3$): 1538; 1503 (C=C, C=N)

1H-NMR (DMSO-d6): δ 1.16 (t, 3H, CH$_2$—CH$_3$); 2.86 (q, 2H, CH$_2$—CH$_3$); 8.63 ppm (s, 1H, N=CH—N)

MS: 266 (MH+); 249 (MH-CH3+); 184 (MH-HBr+).

Synthesis 4-bromo-5-ethyl-6-[4-(1,2,3,4-tetrahydro-1,8-naphthyridin-7-yl)-1-piperidinyl]-pyrimidine

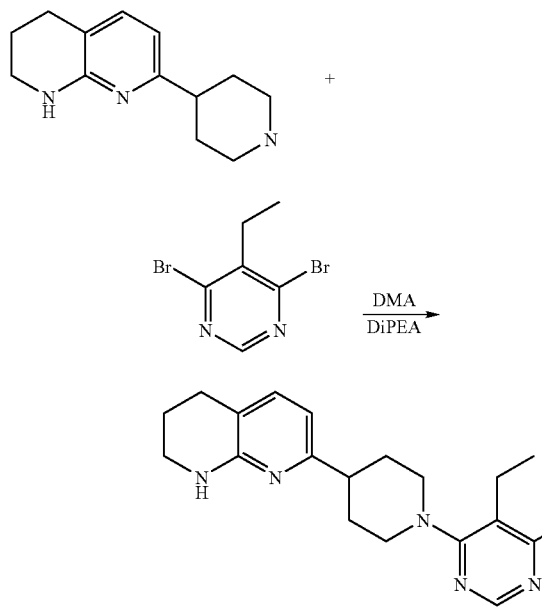

A mixture of 3.67 g (6.45 mmoles) of 1,2,3,4-tetrahydro-7-(4-piperidinyl)-1,8-naphthyridine, tris(trifluoroacetate) (prepared according to Patents EP1065207 or WO 0078317) and of 25 g of Amberlyst A-21 resin (origin Fluka 06424 washed beforehand with a dichloromethane-ethyl acetate-methanol solution 1-1-1) in 150 ml of solution of dichloromethane-ethyl acetate-methanol 1-1-1 is stirred at ambient temperature for 1 hour. The mixture is filtered and the resin is washed with the ternary solution. The filtrate obtained is stirred at ambient temperature for 1 hour in the presence of 25 g of Amberlyst A-21 resin treated as previously; this operation is carried out three times. The filtrate thus obtained is concentrated to dryness under reduced pressure (2 kPa) producing 1.4 g of free amine. 2.06 g (7.74 mmoles) of 4,6-dibromo-5-ethyl-pyrimidine, 200 ml of dimethylacetamide and 5 ml of diisopropylethylamine are added to this residue followed by heating at 100° C. for 3.5 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated under reduced pressure (2 kPa). The residue is chromatographed on silicagel eluting with a gradient of 100% heptane to heptane-ethyl acetate 50-50. 1.5 g (Yield=58%) of expected product is obtained in the form of a beige solid.

TLC: Rf=0.5 (alumina, eluent: heptane-ethyl acetate 50-50)

IR (CHCl3): 3440 (NH); 1596, 1586, 1547, 1508, 1480 cm-1 (Heterocycle+Aromatic)

1H-NMR (DMSO-d6): δ 1.23 (t, 3H, CH$_2$—CH$_3$); 1.75 (m, 6H, CH$_2$—CH$_2$—CH$_2$—NH, CH$_2$—CH—CH$_2$); 2.67 (m, 5H, CH$_2$—CH$_3$, CH$_2$—CH—CH$_2$, CH$_2$—CH$_2$—CH$_2$—NH); 3.02 (t, 2H, CH$_2$—CH$_2$—N); 3.23 (m, 2H, CH$_2$—CH$_2$—CH$_2$—NH); 3.90 (d, 2H, CH$_2$—CH$_2$—N); 6.20 (s, 1H, CH$_2$—CH$_2$—CH$_2$—NH); 6.30 and 7.04 (2d, 2H, H naphthyridine); 8.27 ppm (s, N=CH—N).

MS: 403 (MH+).

Synthesis of (1,1-dimethylethyl)3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate.

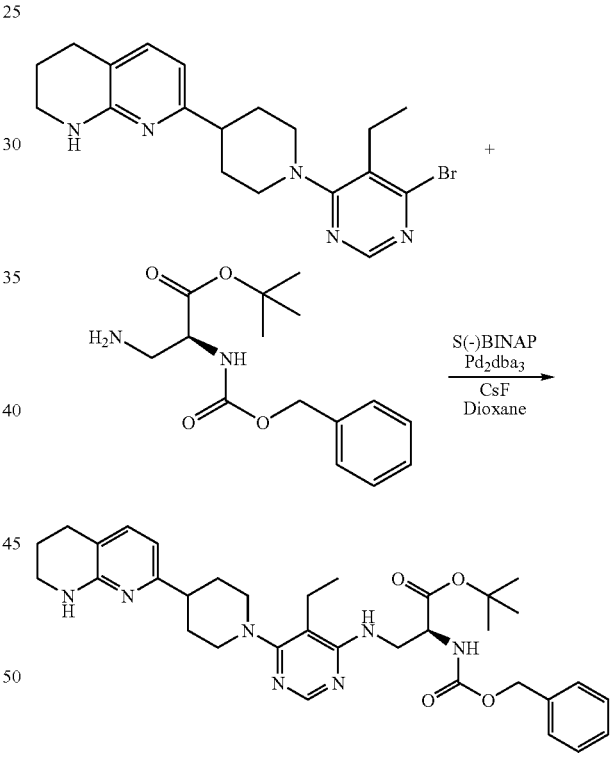

A mixture of 317 mg (0.79 mmoles) of 4-bromo-5-ethyl-6-[4-(1,2,3,4-tetrahydro-1,8-naphthyridin-7-yl)-1-piperidinyl]-pyrimidine, 279 mg (0.95 mmoles) of (1,1-dimethylethyl) 3-amino-N-[(phenylmethoxy)carbonyl]alaninate (prepared according to J. Med. Chem.(2001), 44(8), 1158-1176), 168 mg (1.11 mmoles) of caesium fluoride, 36 mg (0.04 mmoles) of tris(dibenzylideneacetone)dipalladium(0), 49 mg (0.08 mmoles) of S(–)2,2'-bis(diphenyl-phosphino)-1,1'-binaphthyl in 11 ml of dioxane is heated under reflux for 21 hours. After cooling down another 140 mg (0.48 mmoles) of (1,1-dimethylethyl) 3-amino-N-[(phenylmethoxy)carbonyl]alaninate, 168 mg (1.11 mmoles) of caesium fluoride, 36 mg (0.04 mmoles) of tris(dibenzylideneacetone)dipalladium (0), and 49 mg (0.08 mmoles) of S(−)2,2'-bis(diphenyl-phosphino)-1,1'-binaphthyl in 2 ml of dioxane are added and the reaction medium is heated under reflux for 3.5 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on silicagel eluting with a gradient of heptane-ethyl acetate-methanol 50-50-0, 25-75-0, 0-100-0, and finally 0-100-3. 400 mg (Yield=83%) of expected product is obtained in the form of an oil.

TLC: Rf=0.55 (silicagel, eluent: ethyl acetate-methanol-triethylamine 95-2-2).

IR (CHCl3): 3435 (NH); 1717 (C=O); 1583.1555.1501 cm-1 (Heterocycle+Aromatic+Amide).

1H-NMR (DMSO-d6): δ 1.06 (t, 3H, $CH_2$—$C_3$); 1.31 (s, 9H, tBu); 1.75 (m, 2H, $CH_2$—$CH_2$—$CH_2$—$NH$); 1.77 (m, 4H, $CH_2$—CH—$CH_2$); 2.46 (m, 2H, $CH_2$—$CH_3$); 2.53 (m, 1H, $CH_2$—$CH$—$CH_2$); 2.62 (t, 2H, $CH_2$—$CH_2$—$CH_2$—NH); 2.83 and 3.44 (2m, 4H, $CH_2$—$CH_2$—N—$CH_2$—$CH_2$); 3.24 (m, 2H, $CH_2$—$CH_2$—$CH_2$—NH); 3.72 (m, 2H, NH—$CH_2$—CH—NH); 4.23 (q, 1H, NH—$CH_2$—$CH$—NH); 5.02 (s, 2H, $CH_2$-Ph); 6.24 (s, 1H, $CH_2$—$CH_2$—$CH_2$—$NH$); 6.30 and 7.06 (2d, 2H, H naphthyridine); 6.36 (m, H, $NH$—$CH_2$—CH—NH); 7.34 (m, 5H, Ph); 7.62 (d, 1H, NH—$CH_2$—CH—$NH$); 8.11 ppm (s, N=CH—N).

MS: 616 (MH+); 560 (MH-tBu+); 426 (MH-COOCH2Ph+).

[α$_D$] (1% CHCl3): +2.4°

[α$_D$] (1.05% EtOH): −6.1°

Synthesis of 3-[[5-ethyl-6-[4-(1,2,3,4-tetrahydro-1,8-naphthyridin-7-yl)-1-piperidinyl]-4-pyrimidinyl] amino]-N-[(phenylmethoxy)carbonyl]alanine, bis (trifluoroacetate).

475 mg (0.77 mmoles) of 3-[[5-ethyl-6-[4-(1,2,3,4-tetrahydro-1,8-naphthyridin-7-yl)-1-piperidinyl]-4-pyrimidinyl]amino]-N-[(phenylmethoxy) carbonyl]alaninate of (1,1-dimethylethyl) in 15 ml of dichloromethane with 3.5 ml of trifluoroacetic acid is stirred at ambient temperature until the starting product has disappeared according to TLC (silicagel, eluent: CH2Cl2-MeOH-H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 368 mg (Yield=61% expressed as ditrifluoroacetate) of expected product is obtained in the form of an amorphous solid.

TLC: Rf=0.33 (silicagel, eluent: dichloromethane-methanol-water-acetic acid 90-10-1-1)

IR (CHCl$_3$): 1677 (C=O); 1625; 1587; 1492 cm-1 (Conjugated system+Aromatic).

1H-NMR (DMSO-d6): δ 1.04 (t, 3H, CH2-$CH_3$); 1.77 and 1.90 (2m, 4H, N—CH2-$CH_2$-CH—); 1.81 (m, 2H, NH—CH2-$CH_2$-CH2-); 2.45 (q, 2H, $CH_2$-CH3); 2.73 (t, 2H, NH—CH2-CH2-$CH_2$-); 2.78 (t, 1H, N—CH2-CH2-$CH$—); 2.87 and 3.48 (2m, 4H, N—$CH_2$-CH2-CH—); 3.23 (m, 2H, N—$CH_2$-CH2-CH2-); 3.58 and 3.83 (2m, 2H, NH—$CH_2$-CH—NH); 4.28 (q, 1H, NH—CH2-$CH$—NH); 5.01 (syst AB, 2H, O—$CH_2$-Ph); 6.65 (d, 1H, H naphthyridine); 6.55 (bs, 1H, $NH$—CH2-CH—NH); 7.33 (m, 5H, Ph); 7.68 (d, 1H, NH—CH2-CH-$NH$); 7.58 (d, 1H, H naphthyridine); 8.15 (s, 1H, N=$CH$—N); 6.24 ppm (bs, 1H, $NH$—CH2-CH2-CH2-).

MS: 560 (MH+); 426 (MH-COOCH2Ph+); 558- (M-H-); 450- (558-OCH2Ph-); 1117- (2M-H-)

[α$_D$] (1% CHCl3): +2.4°

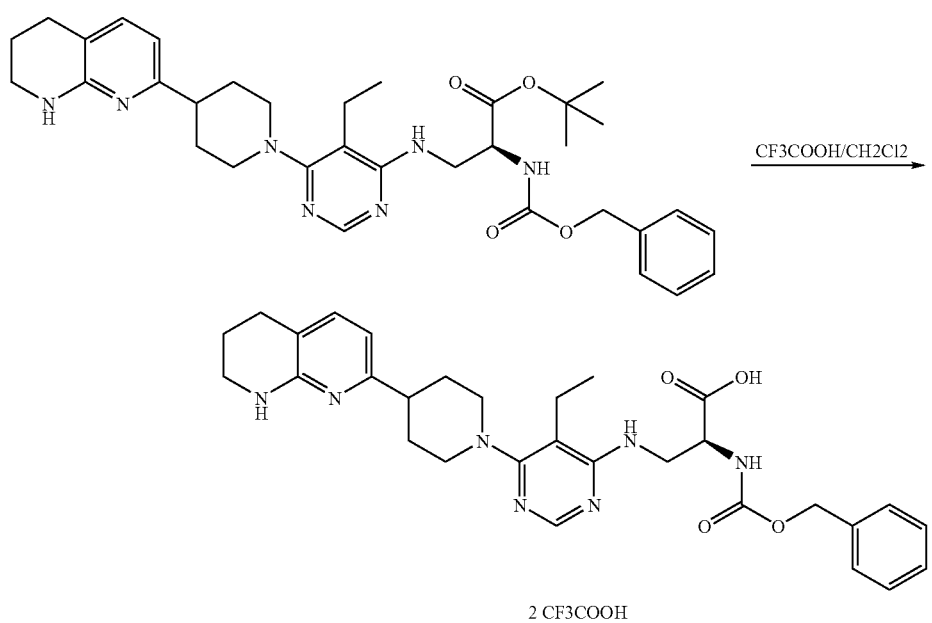

EXAMPLE 10

(1,1 dimethylethyl) N-[(phenylmethoxy)carbonyl]alaninate

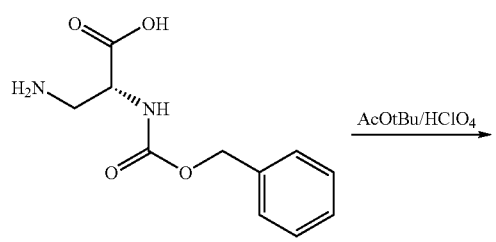

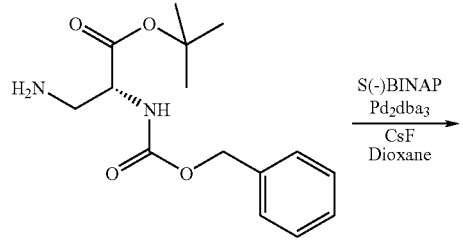

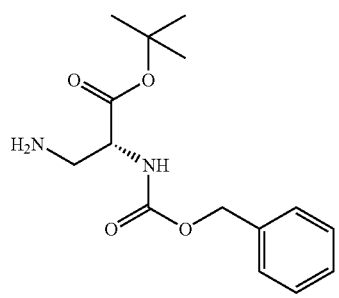

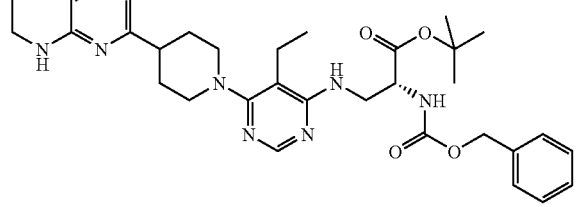

1 ml of perchloric acid is added dropwise to 480 mg (2 mmoles) of N-[(phenylmethoxy)carbonyl]alanic acid in 15 ml of terbutyl acetate. The biphasic mixture is stirred for 24 hours at ambient temperature. The mixture is taken up in ethyl acetate, water and a saturated solution of sodium bicarbonate. The organic phase is separated, dried over magnesium sulphate and the solvent is evaporated off under reduced (2 kPa). The residue is chromatographed on silicagel eluting with a gradient of heptane-ethyl acetate-methanol 100-0-0, 0-100-0, and finally 0-95-05. 50 mg (Yield=10%) of expected product is obtained in the form of an oil.

TLC: Rf=0.20 (silicagel, eluent: dichloromethane-methanol-water-acetic acid 90-10-1-1)

[α$_D$] (1.25% CHCl3): −9.0°

Synthesis of (1,1 dimethylethyl) 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate.

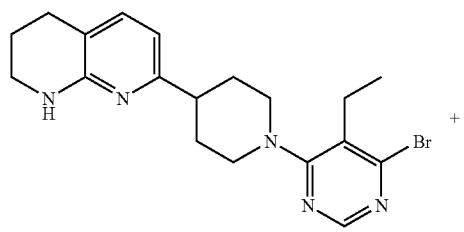

A mixture of 200 mg (0.5 mmole) of 4-bromo-5-ethyl-6-[4-(1,2,3,4-tetrahydro-1,8-naphthyridin-7-yl)-1-piperidinyl]-pyrimidine, 50 mg (0.17 mmole) of (1,1dimethylethyl) (D) 3-amino-N-[(phenylmethoxy)carbonyl]alaninate, 40 mg (0.26 mmole) of caesium fluoride, 15 mg (0.016 mmole) of tris(dibenzylideneacetone)dipalladium(0), 20 mg (0.032 mmole) of 2,2'-bis(diphenyl-phosphino)-1,1'-binaphthyl in 20 ml of dioxane is heated under reflux for 5 hours. After cooling down another 15 mg (0.016 mmole) of tris(dibenzylideneacetone)dipalladium(0) is then added and the reaction mixture heated under reflux for 15 hours, followed by evaporating to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed a first time on alumina eluting with a gradient of ethyl acetate-diisopropyl ether-methylene chloride 50-50-50, 10-50-50, and finally 10-20-70 then on silicagel eluting with ethyl acetate. 40 mg (Yield=38%) of expected product is obtained in the form of an oil.

TLC: Rf=0.25 (silicagel, eluent: ethyl acetate).

MS: 616 (MH+); 560 (MH-tBu+).

[α$_D$] (1.0% CHCl3): −2.4

Synthesis of 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis (trifluoroacetate).

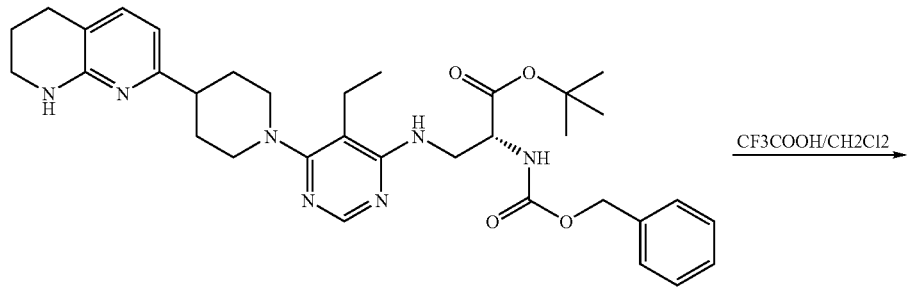

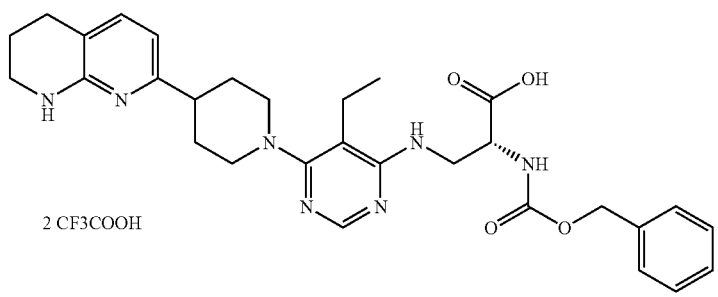

40 mg (0.77 mmoles) of (1,1-dimethylethyl)3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate in 10 ml of dichloromethane with 1 ml of trifluoroacetic acid is stirred at ambient temperature until the starting product has disappeared according to TLC (silicagel, eluent: CH2Cl2-MeOH—H2O—AcOH 90-10-1-1). Toluene is added and the reaction mixture is evaporated to dryness under reduced pressure (2 kPa). The residue is chromatographed on silicagel eluting with a CH$_2$Cl$_2$-MeOH—H$_2$O—AcOH mixture 90-10-1-1. 25 mg (Yield=48% expressed as ditrifluoroacetate) of expected product is obtained in the form of an amorphous solid.

TLC: Rf=0.10 (silicagel, eluent: dichloromethane-methanol-water-acetic acid 90-10-1-1)

MS: 560 (MH+); 426 (MH-COOCH2Ph+); 558- (M-H-); 450- (558–OCH2Ph-); 1117- (2M-H-)

[α$_D$] (1.75% CHCl3): −6.0

Example 11

Ethyl 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate, dihydrochloride

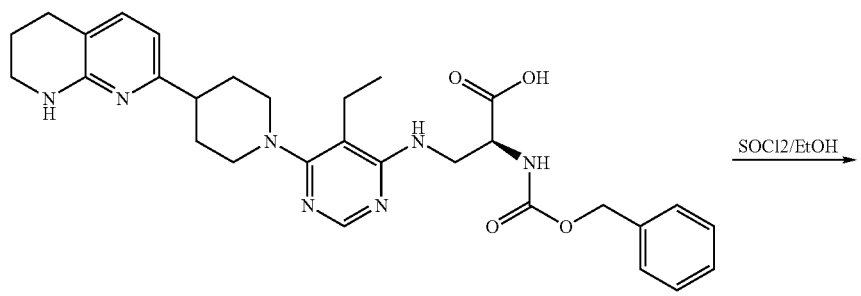

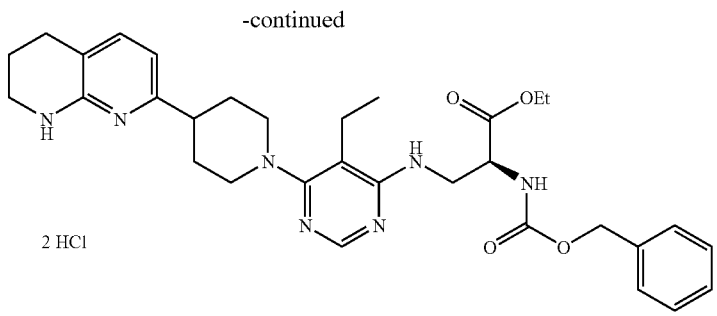

2 HCl

160 μl (2.19 mmoles) of thionyl chloride is added to 5 ml of ethanol cooled down to −12° C. under a nitrogen atmosphere and the mixture is stirred for 30 minutes. Then a solution of 354 mg (0.45 mmoles) of 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis(trifluoroacetate) in 13 ml of ethanol is added. The mixture is stirred for 30 minutes at −12° C. then left to return to ambient temperature and finally heated at 40° C. for 4 hours under nitrogen. The reaction mixture is evaporated to dryness under reduced pressure (2 kPa) and the residue crystallizes from a mixture of diisopropyl ether and pentane and the solid is filtered. 284 mg (Yield=95%) of expected product is obtained in the form of an amorphous beige solid.

TLC: Rf=0.4 (silicagel, eluent: dichloromethane-methanol-water-acetic acid 90-10-1-1)

IR (CHCl$_3$): 3400-3000(OH, NH); 1719(C=O); 1654; 1623; 1580; 1504 cm-1 (C=C, C=N, aromatic)

1H-NMR (DMSO-d6): δ 1.09 (t, 3H, CH2-C<u>H</u>3); 1.14 (t, 3H, O—CH2-C<u>H</u>3); 1.85 (m, 2H, NH—CH2-C<u>H</u>2-CH2); 1.85 and 2.00 (2m, 4H, N—CH2-C<u>H</u>2-CH); 2.48 (m, 2H, C<u>H</u>2-CH3); 2.75 (t, 2H, NH—CH2-CH2-C<u>H</u>2); 2.92 (m, 1H, N—CH2-CH2-C<u>H</u>); 3.03 and 3.57 (2m, 4H, N—C<u>H</u>2-CH2-CH); 3.44 (t, 2H, N—C<u>H</u>2-CH2-CH2); 3.76 and 3.87 (2m, 2H, NH—C<u>H</u>2-CH—NH); 4.07 (q, 2H, O—C<u>H</u>2-CH3); 4.39 (q, 1H, NH—CH2-C<u>H</u>—NH); 5.03 (s, 2H, O—C<u>H</u>2-Ph); 6.62 (d, 1H, H naphthyridine); 6.86 (bs, 1H, N<u>H</u>—CH2-CH—NH); 7.30 (m, 5H, Ph); 7.33 (bs, 1H, NH—CH2-CH—N<u>H</u>) 7.58 (d, 1H, H naphthyridine); 8.20 ppm (s, 1H, N=C<u>H</u>—N).

MS: 588 (MH+); 454 (MH-COOCH2Ph+); 426 (454-C2H4+).

[αD] (1% CHCl3): +4

Example 12 ethyl N-[(phenylmethoxy)carbonyl]alaninate

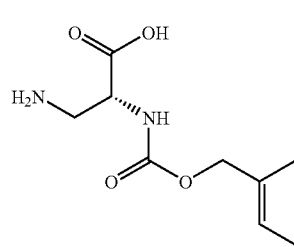

SOCl2/EtOH →

-continued

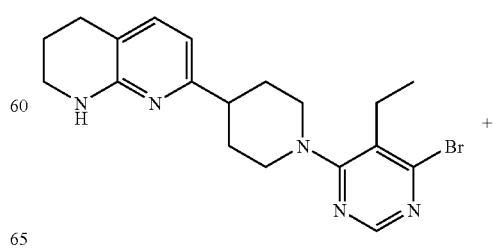

6 ml (63 mmoles) of thionyl chloride is added to 12 ml of ethanol cooled down to 0° C. under a nitrogen atmosphere and the mixture is stirred for 20 minutes at ambient temperature. Then a solution of 950 mg (4 mmoles) of N-[(phenylmethoxy)carbonyl]alanic acid in 5 ml of ethanol is added. The mixture is stirred under reflux for 1 hour under nitrogen. The reaction mixture is evaporated to dryness under reduced pressure (2 kPa) and the residue crystallizes from a mixture of diisopropyl ether and pentane and the solid is filtered. The solid obtained is taken up in ethyl acetate, water and a saturated solution of sodium bicarbonate. 535 mg (Yield=50%) of expected product is obtained in the form of a colourless oil.

TLC: Rf=0.4 (silicagel, eluent: dichloromethane-methanol-water-acetic acid 90-10-1-1)

HPLC/MS : (rt=0.5 and 1.4 min) 267 (MH+).

[αD] (1.0% CHCl3): −11.2

Synthesis of ethyl 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate.

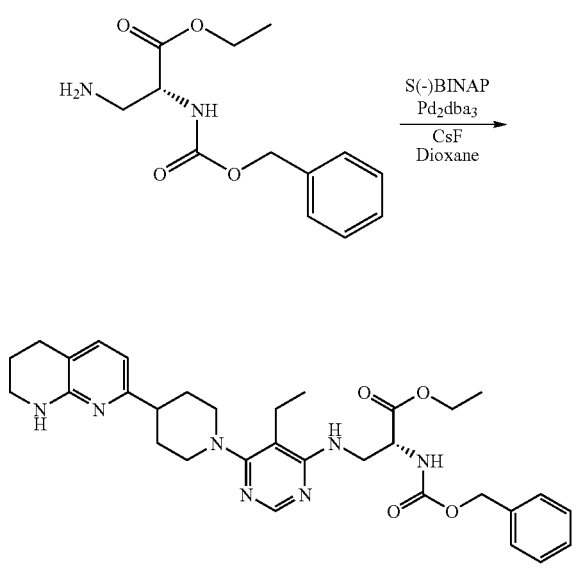

A mixture of 320 mg (0.8 mmole) of 4-bromo-5-ethyl-6-[4-(1,2,3,4-tetrahydro-1,8-naphthyridin-7-yl)-1-piperidinyl]-pyrimidine, 215 mg (1.04 mmole) of ethyl (D) 3-amino-N-[(phenylmethoxy)carbonyl]alaninate, 190 mg (1.25 mmoles) of caesium fluoride, 37 mg (0.04 mmole) of tris(dibenzylideneacetone)dipalladium(0), 50 mg (0.08 mmole) of S(−)2,2'-bis(diphenyl-phosphino)-1,1'-binaphthyl in 15 ml of dioxane is heated under reflux for 5 hours. After cooling down another 37 mg (0.04 mmole) of tris(dibenzylideneacetone)dipalladium(0) is then added and the reaction mixture is heated under reflux for 7 hours, followed by evaporating to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on alumina eluting with a gradient of ethyl acetate-diisopropyl ether-methylene chloride 50-50-50, 10-50-50, and finally 10-20-70. 260 mg (Yield=55%) of expected product is obtained in the form of an oil.

TLC: Rf=0.25 (silicagel, eluent: ethyl acetate).

1H-NMR (CDCl3): δ 1.16 (t, 3H, CH2-CH3); 1.27 (t, 3H, O—CH2-CH3); 1.85 to 2.00 (m, 6H, N—CH2-CH2-CH and NH—CH2-CH2-CH2); 2.46 (m, 2H, CH2-CH3); 2.75 (t, 3H, NH—CH2-CH2-CH2 and N—CH2-CH2-CH); 3.89 (t, 2H, N—CH2-CH2-CH2); 3.47 and 3.61 (2m, 4H, N—CH2-CH2-CH); 3.00 and 3.98 (2m, 2H, NH—CH2-CH—NH); 4.22 (m, 2H, O—CH2-CH3); 4.54 (m, 1H, NH—CH2-CH—NH); 5.13 (s, 2H, O—CH2-Ph); 6.43 (d, 1H, H naphthyridine); 7.22 (d, 1H, H naphthyridine); 7.35 (m, 5H, Ph); 8.27 ppm (s, 1H, N=CH—N).

MS: 588 (MH+); 454 (MH-COOCH2Ph+).

[αD] (1.3% CHCl3): −6.0

Example 13

Synthesis of 6-[4-(1,2,3,4-tetrahydro-1,8-naphthyridin-7-yl)-1-piperidinyl]-5-ethyl-4-chloro-pyrimidine

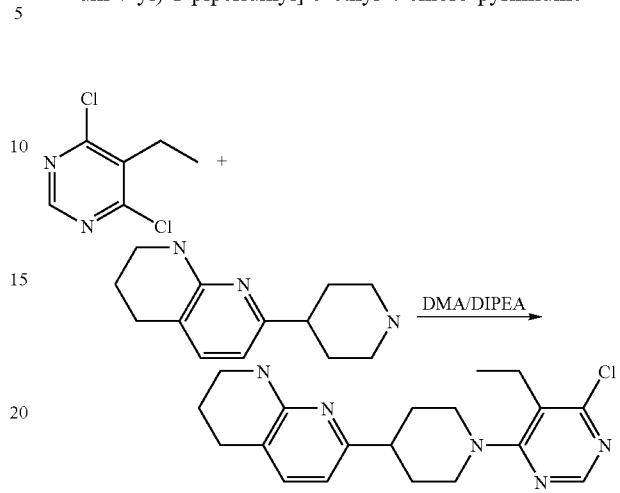

80 ml dimethylacetamide, 11.8 g (30 mmoles) of 4,6-dichloro-5-ethyl-pyrimidine solubilized in 40 ml of dimethylacetamide and 24 ml of diisopropylethylamine are added into a single-necked flask containing 12.5 g (57.5 mmoles) of 4-(1,2,3,4-tetrahydro-1,8-naphthyridin-7-yl)-1-piperidine released from its salt. This mixture is heated at 140° C. for 5 hours then concentrated to dryness under vacuum. The residue obtained is taken up in a mixture of water, ethyl acetate and a saturated solution of sodium bicarbonate. The organic phase is separated and the aqueous phase reextracted with ethyl acetate. The combined organic phases are dried over magnesium sulphate then the solvent is evaporated off under vacuum in order to produce 15.5 g of an orange oil. This oil is solubilized in a minimum amount of methylene chloride and precipitated from isopropyl ether, 9 g of the expected product is obtained in the form of a beige powder. The filtrate is concentrated to dryness then chromatographed on silicagel eluting with a gradient of cyclohexane (100%), ethyl acetate-cyclohexane (50-50) then ethyl acetate-cyclohexane (70-30).

3 g of expected product is obtained in the form of a pale yellow powder. (Overall yield=58%)

Preparation of the naphthyridine in free amine form:

28.5 g of naphthyridine is displaced from its salt by 6 mass equivalents of basic amberlyst A21 resin (resin of R—NMe2 type) in a CH2Cl2/MeOH/AcOEt mixture 1/1/1 under stirring for 30 minutes. The resin is washed beforehand and left to swell for 20 minutes in this solvent mixture.

This operation must be repeated 3 times for the displacement of the salt to be complete.

After filtration of the resin and evaporation of the solvents, 12.5 g (57.5 mmoles) of free naphthyridine is obtained.

TLC: Rf=0.32 [silicagel, eluent: ethyl acetate (100%)]

1H-NMR ( ): δ 1.32 (t, 3H, CH3-CH2); 1.81 to 2.05 (m, 6H, NH—CH2-CH2-CH2, N—CH2-CH2-CH—CH2); 2.70 (m, 5H, CH2-CH—CH2, NH—CH2-CH2-CH2, CH3-CH2); 3.43 (m, 2H, NH—CH2-CH2-CH2); 3.05 and 3.97 (2m, 4H, CH2-CH2-N—CH2-CH2); 6.4 and 7.12 (2d, 2H, CH=CH naphthyridine); 8.37 (s, 1H, N=CH—N).

HPLC/MS: (rt=0.51 min and 2.93 min): 358 (MH+)

Synthesis of isopropyl 3-[[6-[4-(1,2,3,4-tetrahydro-1,8-naphthyridin-7-yl)-1-piperidinyl]-5-ethyl-4-pyrimidinyl]amino]-N-[(phenylmethoxy)carbonyl]alaninate.

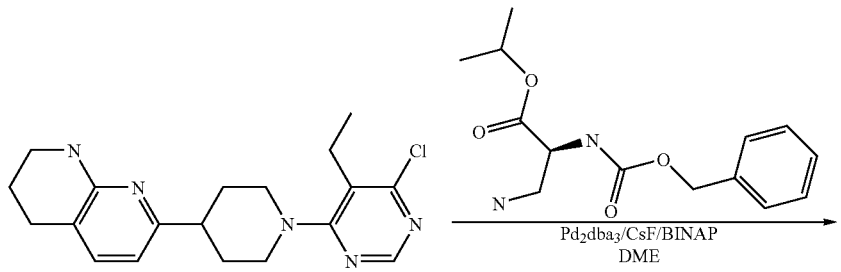

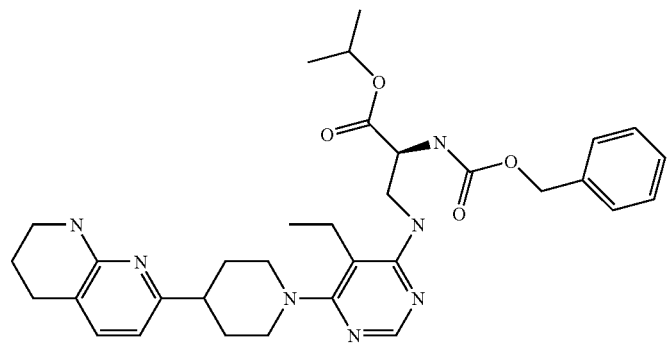

A mixture of 1 g (2.79 mmoles) of 6-[4-(1,2,3,4-tetrahydro-1,8-naphthyridin-7-yl)-1-piperidinyl]-5-ethyl-4-chloropyrimidine and 940 mg (3.35 mmoles) of isopropyl 3-amino-N-[(phenylmethoxy)carbonyl]alaninate is heated under reflux for 5 hours, in the presence of 594 mg (3.91 mmoles) of caesium fluoride, 174 mg (279 μmoles) of (2,2'-bis(diphenylphosphino)-1,1'-binaphthyl and 130 mg (140 μmoles) of tris(dibenzylideneacetone)dipalladium(o) in 35 ml of 1,2-dimethoxyethane. The reaction mixture is then taken to temperature for the addition of 180 mg (140 μmoles) of tris(dibenzylideneacetone)dipalladium(o), then again taken to reflux for 16 hours.

After cooling down the solution is concentrated to dryness then taken up a mixture of water, ethyl acetate and a saturated solution of sodium bicarbonate. The organic phase is decanted and the aqueous phase is extracted with ethyl acetate. The combined organic phases are dried over magnesium sulphate and evaporated to dryness under vacuum. The residue is chromatographed on silicagel with 100% ethyl acetate. 1.07 g of expected product is obtained in the form of pale yellow crystals (yield=64%)

TLC: Rf=0.20 (silicagel eluent: ethyl acetate 100%

1H-NMR (CDCl3): δ 1.18 (t, 3H, CH3-CH2); 1.25 (d, 6H, CH3-CH—CH3); 1.83 to 2.05 (m, 6H, NH—CH2-CH2-CH2, N—CH2-CH2-CH—CH2); 2.45 (q, 2H, CH3-CH2); 2.72 (m, 3H, CH2-CH—CH2, NH—CH2-CH2-CH2); 2.97 and 3.93 (2m, 4H, CH2-CH2-N—CH2-CH2); 3.45 (m, 2H, NH—CH2-CH2-CH2); 3.60 (d, 2H, NH—CH2-CH—NH), 4.50 (m, 1H, NH—CH2-CH—NH); 4.97 to 5.20 (m, 3H, CH3-CH—CH3, O—CH2-Ph); 6.43 and 7.18 (2d, 2H, CH═CH naphthyridine); 7.35 (m, 5H, Ph); 8.28 (s, 1H, N═CH—N).

HPLC/MS : (rt=0.50 min and 3.14 min): 602 (MH+); 468 [MH-Z+]; 426 [MH-(ipr-Z)+]

$[\alpha]_D$ (CHCl3)=+2.175

Formation of the hydrochloride:

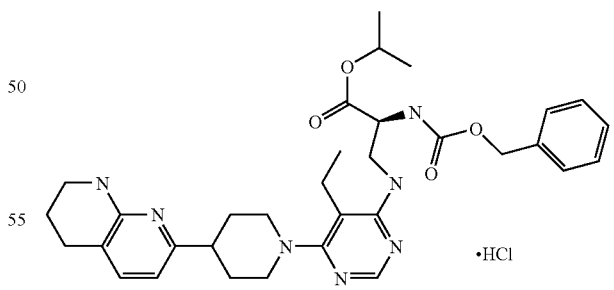

3.2 g (5.3 mmoles) of isopropyl 3-[[6-[4-(1,2,3,4-tetrahydro-1,8-naphthyridin-7-yl)-1-piperidinyl]-5-ethyl-4-pyrimidinyl]amino]-N-[(phenylmethoxy)carbonyl]alaninate is solubilized in a minimum amount of methylene chloride. This solution is poured into ethyl ether, the solution must remain clear. Then, 2.65 ml of 2N HCl in ethyl ether is added dropwise, under stirring. The hydrochloride solidifies, the supernatant is removed, then the residue is recrystallized from isopropyl ether. Then a solid is obtained which is filtered, rinsed with ether then with pentane. After drying, 3.5 g of an off-white powder is obtained. (Yield=quantitative).

Example 14

Synthesis of terbutyl 2-(2-benzyloxycarbonylamino-3-{5-ethyl-6-[4-(5,6,7,8-tetrahydro-[1,8]naphthyridin-2-yl)-piperidin-1-yl]-pyrimidin-4-ylamino}-propinylamino)-4-methylpentanoate

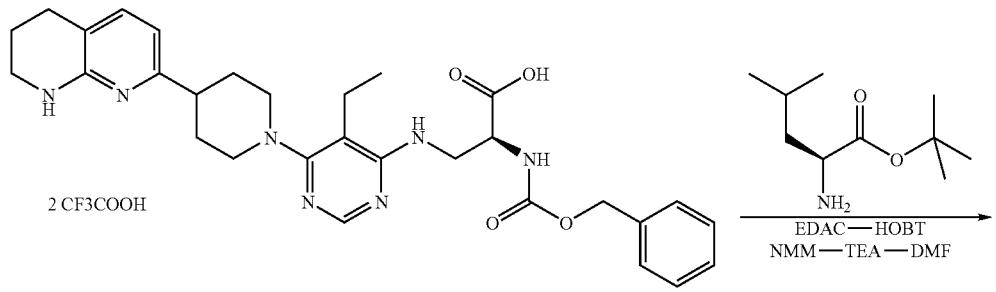

80 mg (0.15 mmole) of 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, 45 mg (0.20 mmole) of terbutyl L-leucinate hydrochloride, 22 mg (0.16 mmole) of 1-hydoxy benzotriazole, 30 mg (0.16 mmole) of 1-[3-(dimethylamino) propyl]-3-ethyl carbodiimide hydrochloride, 0.050 ml (0.45 mmole) of N-methhylmorpholine and 0.070 ml (0.50 mmole) of triethylamine in 5 ml of dimethylformamide are stirred for 24 hours at ambient temperature. The reaction mixture is evaporated to dryness under reduced pressure (2 kPa) and the residue is taken up in ethyl acetate and a saturated solution of sodium bicarbonate. The organic phase is separated, dried over magnesium sulphate and the solvent is evaporated off under reduced pressure (2 kPa). The residue is chromatographed on silicagel eluting with a gradient of ethyl acetate-methylene chloride-methanol of 50-50-0 to 50-45-5. 60 mg (Yield=55%) of expected product is obtained in the form of a white solid.

TLC: Rf=0.66 (silicagel, eluent: dichloromethane-methanol-water-acetic acid 85-15-2-2)

1H-NMR (CDCl3): δ 0.91 (t, 3H, CH2-<u>CH3</u>); 1.16 (d, 6H, CHCH2CH(<u>CH3)2</u>); 1.28 (bt, 2H, CH<u>CH2</u>CH(CH3)2); 1.41 to 1.57 (m, 1H, CHCH2<u>CH</u>(CH3)2); 1.48 (s, 9H, tBu); 1.80 to 2.05 (m, 6H, CH$_2$—<u>CH$_2$</u>—CH$_2$—NH, <u>CH$_2$</u>—CH—<u>CH$_2$</u>); 2.49 (m, 2H, <u>CH$_2$</u>—CH$_3$); 2.67 (tt, 1H, <u>CH$_2$</u>—CH—<u>CH$_2$</u>); 2.73 (t, 2H, <u>CH$_2$</u>—CH$_2$—CH$_2$—NH); 2.98 and 3.66 (bq and m, 4H, CH$_2$—<u>CH$_2$</u>—N—<u>CH$_2$</u>—CH$_2$); 3.43 (m, 2H, CH$_2$—CH$_2$—<u>CH$_2$</u>—NH); 3.70 and 4.16 (2m, 2H, NH—<u>CH$_2$</u>—CH—NH); 4.32 (m, 1H, NH—CH$_2$—<u>CH</u>—NH); 4.49 (m, 1H, CONH—<u>CH</u>CH2CH(CH3)2)-CO); 5.13 (m, 2H, <u>CH$_2$</u>-Ph); 5.42, 6.83 and 7.92 (3H, mobile Hs); 6.43 and 7.15 (2d, 2H, H naphthyridine); 7.37 (m, 5H, Ph); 8.2 ppm (s, 1H, N=<u>CH</u>—N).

MS: 729 (MH+).

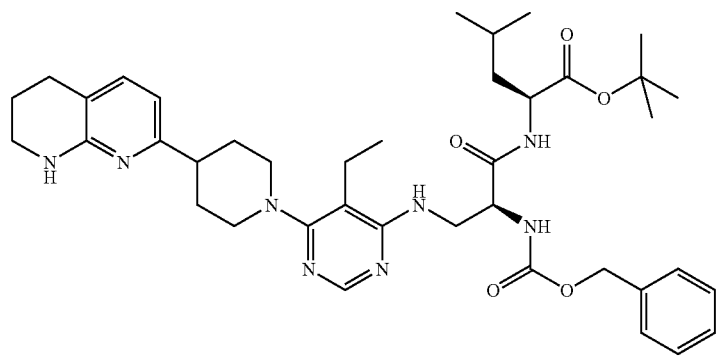

Synthesis of 2-(2-benzyloxycarbonylamino-3-{5-ethyl-6-[4-(5,6,7,8-tetrahydro-[1,8]naphthyridin-2-yl)-piperidin-1-yl]-pyrimidin-4-ylamino}-propinylamino)-4-methylpentanoic acid.

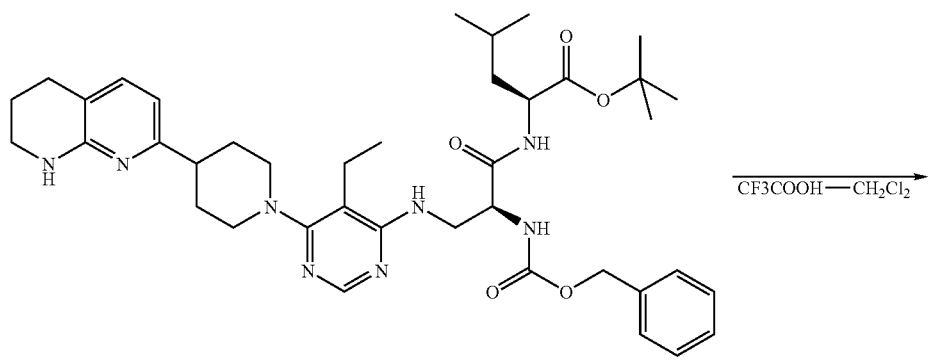

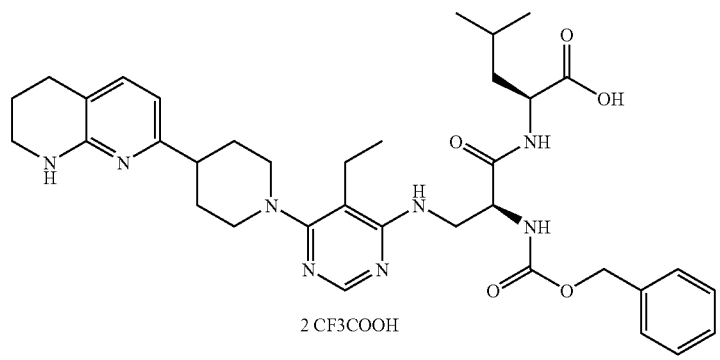

60 mg (0.083 mmoles) of terbutyl 2-(2-benzyloxycarbonylamino-3-{5-ethyl-6-[4-(5,6,7,8-tetrahydro-[1.8]naphthyridin-2-yl)-piperidin-1-yl]-pyrimidin-4-ylamino}-propinylamino)-4-methylpentanoate in 5 ml of dichloromethane with 0.5 ml of trifluoroacetic acid is stirred at ambient temperature until the starting product disappears according to TLC (silicagel, eluent: CH2Cl 2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 55 mg (Yield=74% expressed as ditrifluoroacetate) of expected product is obtained in the form of a white solid.

TLC: Rf=0.52 (silicagel, eluent: dichloromethane-methanol-water-acetic acid 85-15-2-2)

MS: 673 (MH+).

Example 15

Synthesis of 4,6-dihydroxy-5-propyl-pyrimidine

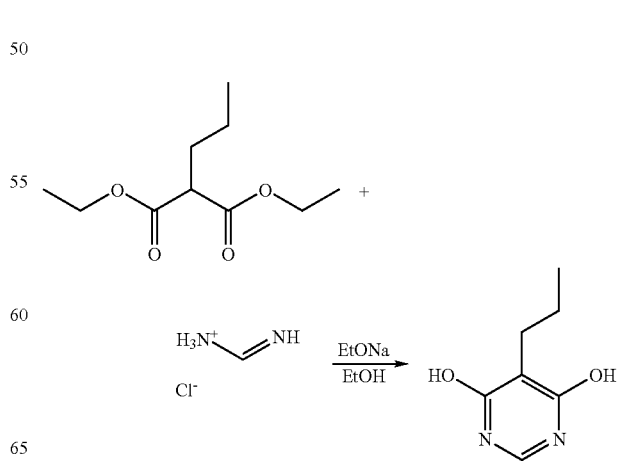

102 ml (282 mmoles) of a solution of 21% sodium ethylate in ethanol is added to a solution of 7.5 g (94 mmoles) of formamidine hydrochloride in 200 ml of ethanol cooled down to 0° C. and the mixture is stirred for 30 minutes; then a solution of 19.5 ml (94 mmoles) of diethyl propyl malonate in 50 ml of ethanol is added and the reaction mixture is stirred overnight at ambient temperature, followed by evaporating to dryness under reduced pressure (2 kPa). The residue is taken up in 100 ml of a saturated solution of sodium chloride and extraction is carried out with 800 and 200 ml of n-butanol. The organic phases are dried over sodium sulphate, filtered and evaporated to dryness under reduced pressure (2 kPa). 7.3 g (Yield=50%) of expected product is obtained in the form of a beige solid.

1H-NMR (DMSO d6): 0.85(t, 3H, CH$_2$—CH$_2$—CH$_3$); 1.39(sext, 2H, CH$_2$—CH$_2$—CH$_3$); 2.23(t, 2H, CH$_2$—CH$_2$—CH$_3$); 7.85 ppm (s, N=CH—N).

MS: 155 (MH+); 159 (M-H-).

Synthesis of 4,6-dichloro-5-propyl-pyrimidine

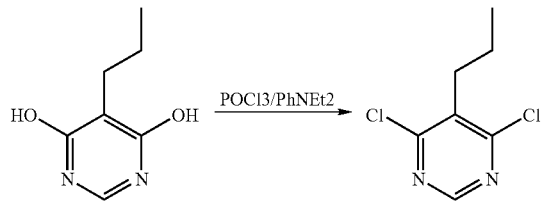

A mixture of 3 g (19.5 mmoles) of 5-propyl-4,6-dihydroxy-pyrimidine in 20 ml of phosphorus oxychloride is taken to reflux for 1 hour. After returning to ambient temperature, a mixture of 3 ml of N,N-diethylaniline in 10 ml of phosphorus oxychloride is added dropwise and the reaction mixture is taken to reflux for 4 hours. After returning to ambient temperature, the reaction mixture is poured into a mixture of ice and water then sodium bicarbonate is added slowly to a basic pH, followed by extracting with ethyl acetate, drying over magnesium sulphate and evaporating to dryness under reduced pressure (2 kPa). The residue is chromatographed on alumina eluting with a gradient of heptane-methylene chloride 100-0 to 80-20. 2 g (Yield=54%) of expected product is obtained in the form of a blueish solid.

TLC: Rf=0.35 (silicagel, eluent: heptane-ethyl acetate 90-10).

Synthesis of 6-[4-(1,2,3,4-tetrahydro-1,8-naphthyridin-7-yl)-1-piperidinyl]-5-propyl-4-chloro-pyrimidine:

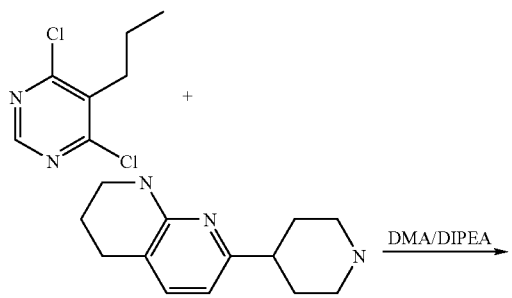

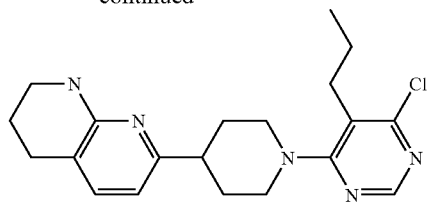

50 ml dimethylacetamide, 2 g (10.5 mmoles) of 4,6-dichloro-5-propyl-pyrimidine and 4 ml of diisopropylethylamine are added into a single-necked flask containing 1.6 g (7.4 mmoles) of 4-(1,2,3,4-tetrahydro-1,8-naphthyridin-7-yl)-1-piperidine released from its salt. This mixture is heated at 140° C. for 5 hours then concentrated to dryness under reduced pressure (2 kPa). The residue obtained is taken up in a mixture of water, ethyl acetate and a saturated solution of sodium bicarbonate. The organic phase is separated and the aqueous phase reextracted with ethyl acetate. The combined organic phases are dried over magnesium sulphate then the solvent is evaporated off under reduced pressure (2 kPa). The residue is chromatographed on silicagel eluting with a gradient of heptane-methylene chloride-ethyl acetate of 50-50-0 to 0-0-100. 875 mg of expected product is obtained in the form of an amorphous solid. (Yield=50%)

TLC: Rf=0.25 [silicagel, eluent: ethyl acetate (100%)]

1H-NMR (CDCl3): δ 1.02(t, 3H, C—CH$_2$—CH$_2$—CH$_3$); 1.72(sext, 2H, C—CH$_2$—CH$_2$—CH$_3$); 1.81 to 2.07 (m, 6H, NH—CH2-CH2-CH2, N—CH2-CH2-CH—CH2); 2.64(t, 2H, C—CH$_2$—CH$_2$—CH$_3$); 2.73 (m, 3H, CH2-CH—CH2, NH—CH2-CH2-CH2); 3.46 (t, 2H, NH—CH2-CH2-CH2); 3.06 and 3.96 (m and d, 4H, CH2-CH2-N—CH2-CH2); 5.00 (m, 2H, NH—CH2-CH2-CH2); 6.40 and 7.14 (2d, 2H, CH=CH naphthyridine); 8.38 (s, 1H, N=CH—N).

MS: 372.374 (MH+).

Synthesis of (1,1-dimethylethyl)3-[[5-propyl-6-[4-(1,2,3,4-tetrahydro-1,8-naphthyridin-7-yl)-1-piperidinyl]-4-pyrimidinyl]amino]-N-[(phenylmethoxy)carbonyl]alaninate.

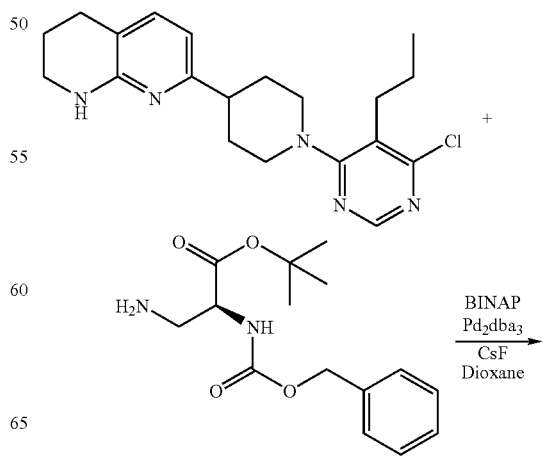

-continued

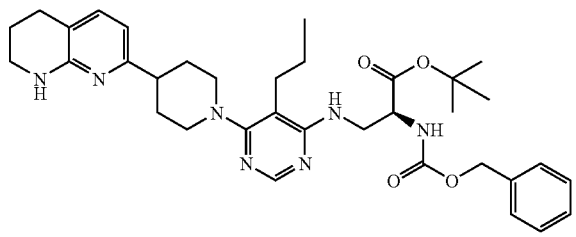

A mixture of 600 mg (1.62 mmoles) of 4-chloro-5-propyl-6-[4-(1,2,3,4-tetrahydro-1,8-naphthyridin-7-yl)-1-piperidinyl]-pyrimidine, 590 mg (2 mmoles) of (1,1-dimethylethyl) 3-amino-N-[(phenylmethoxy)carbonyl]alaninate (prepared according to J. Med. Chem. (2001), 44(8), 1158-1176), 380 mg (2.51 mmoles) of caesium fluoride, 76 mg (0.083 mmole) of tris(dibenzylideneacetone)dipalladium(0), 102 mg (0.163 mmole) of 2,2'-bis(diphenyl-phosphino)-1,1'-binaphthyl in 50 ml of dioxane are heated under reflux for 20 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on alumina eluting with a gradient of methylene chloride-diisopropyl ether-ethyl acetate-methanol from 50-50-0-0 to 0-50-50-0 then 0-0-100-0 and finally 0-0-90-10. 620 mg (Yield=61%) of expected product is obtained in the form of an amorphous yellow solid.

TLC: Rf=0.12 (silicagel, eluent: ethyl acetate).

1H-NMR (CDCl3): δ 0.90(t, 2H, C—CH$_2$—CH$_2$CH$_3$); 1.01(t, 3H, C—CH$_2$—CH$_2$—CH$_3$); 1.48 (s, 9H, tBu); 1.81 to 2.07 (m, 6H, NH—CH2-CH2-CH2, N—CH2-CH2-CH—CH2); 2.39(t, 2H, C—CH$_2$—CH$_2$—CH$_3$ ); 2.65 (bt, 1H, CH2-CH—CH2); 2.73 (t, 2H, NH—CH2-CH2-CH2); 2.97 and 3.55 (bt and bd, 4H, CH2-CH2-N—CH2-CH2); 3.44 (m, 2H, NH—CH2-CH2-CH2); 3.85 and 3.93 (2m, 2H, NH—CH$_2$—CH—NH); 4.46 (m, 1H, NH—CH$_2$—CH—NH); 5.14 (s, 2H, CH$_2$-Ph); 6.16 (d, 1H CH$_2$—CH$_2$—CH$_2$—NH); 6.44 (d, 1H, H naphthyridine); 7.15 (d, 1H, H naphthyridine), 7.37 (m, 5H, CH2Ph); 8.29 (s, 1H, N=CH—N);

MS: 630 (MH+); 574 (MH-tBu+); 440 (MH-COOCH2Ph+).

Synthesis of 3-[[5-propyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis (trifluoroacetate).

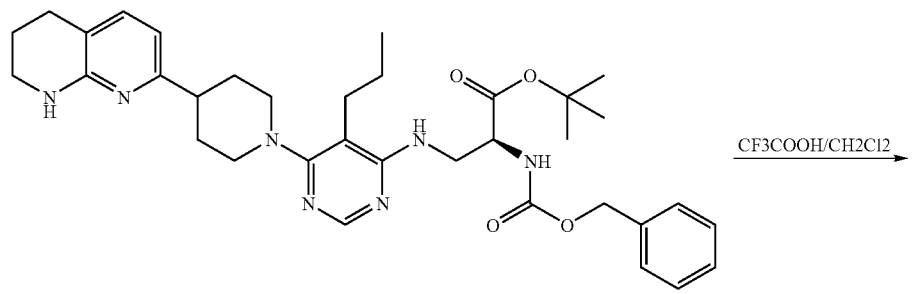

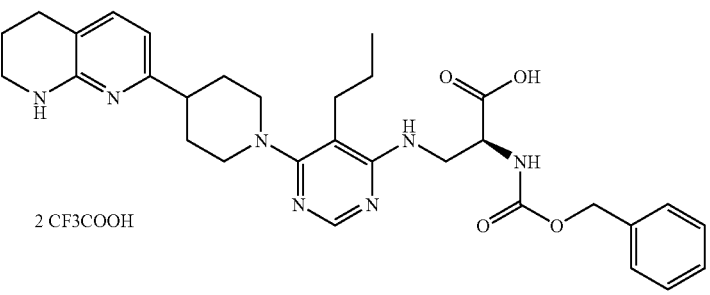

610 mg (0.97 mmole) of (1,1-dimethylethyl) 3-[[5-propyl-6-[4-(1,2,3,4-tetrahydro-1,8-naphthyridin-7-yl)-1-piperidinyl]-4-pyrimidinyl]amino]-N-[(phenylmethoxy)carbonyl] alaninate in 50 ml of dichloromethane with 5 ml of trifluoroacetic acid is stirred at ambient temperature until the starting product disappears according to TLC (silicagel, eluent: CH2Cl2-MeOH-H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 400 mg (Yield=51% expressed as ditrifluoroacetate) of expected product is obtained in the form of a beige solid.

TLC: Rf=0.40 (silicagel, eluent: dichloromethane-methanol-water-acetic acid 85-15-2-2)

1H-NMR (DMSO d6): δ 0.93(t, 3H,C—CH$_2$—CH$_2$—CH$_3$); 1.48(m, 2H, C—CH$_2$—CH$_2$—CH$_3$); 1.67 to 2.00(m, 6H, CH$_2$—CH$_2$—CH$_2$—NH and CH$_2$—CH—CH$_2$); 2.40 (t, 2H, C—CH$_2$—CH$_2$—CH$_3$); 2.65 to 2.96 (m, 5H, NH—CH2-CH2-CH2-, N—CH2-CH2-CH—, N—CH2-CH2-CH—); 3.32 to 3.51 (m, 4H, N—CH2-CH2-CH— and NH—CH2-CH2-CH2-); 3.56 and 3.84 (2m, 2H, NH—CH2-CH—NH); 4.31 (q, 1H, NH—CH2-CH—NH); 5.02 (s, 2H, O—CH2-Ph); 6.68 (d, 1H, H naphthyridine); 7.33 (m, 5H, Ph); 7.61 (m, 1H, H naphthyridine); 8.20 (s, 1H, N=CH—N).

MS: 574 (MH+); 440 (MH-COOCH2Ph+); 572−(M-H-); 464−(572−OCH2Ph-); 1145=(2M-H-)

[α$_D$] (1.20% CHCl3): −17.7.

Example 16

Synthesis of 4,6-dihydroxy-5-isobutyl-pyrimidine

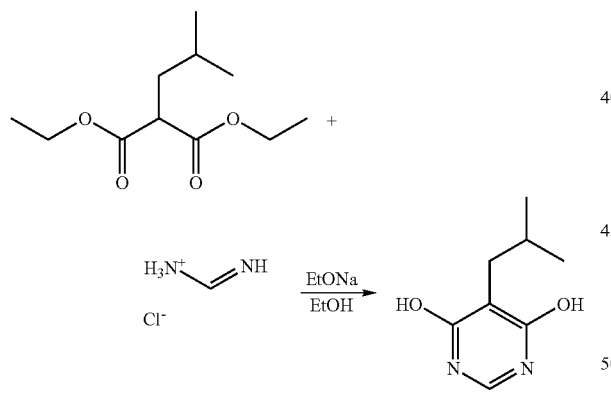

102 ml (282 mmoles) of a solution of 21% sodium ethylate in ethanol is added to a solution of 7.5 g (94 mmoles) of formamidine hydrochloride in 200 ml of ethanol cooled down to 0° C. and the mixture is stirred for 30 minutes; then a solution of 20.6 ml (94 mmoles) of diethyl propyl malonate in 50 ml of ethanol is added and the reaction mixture is stirred overnight at ambient temperature, followed by evaporating to dryness under reduced pressure (2 kPa). The residue is taken up in 100 ml of a saturated solution of sodium chloride and extracted with 800 and 200 ml of n-butanol. The organic phases are dried over sodium sulphate, filtered and evaporated to dryness under reduced pressure (2 kPa). 13.7 g (Yield=86%) of expected product is obtained in the form of a beige solid.

TLC: Rf=0.53 (silicagel, eluent: dichloromethane-methanol-water-acetic acid 85-15-2-2)

1H-NMR (DMSO d6): δ 0.81(d, 6H, CH$_2$—CH—(CH$_3$)2); 1.85 (m, 1H, —CH$_2$—CH—(CH$_3$)2); 2.13(d; 2H, —CH$_2$—CH—(CH$_3$)$_2$); 7.81 ppm (s, N=CH—N).

MS: 169 (MH+); 167 (M-H-).

Synthesis of 4,6-dichloro-5-isobutyl-pyrimidine

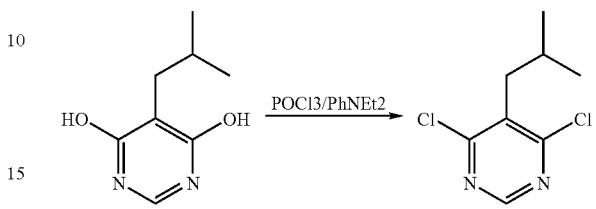

A mixture of 3 g (17.9 mmoles) of 5-isobutyl-4,6-dihydroxy-pyrimidine in 20 ml of phosphorus oxychloride is taken to reflux for 1 hour. After returning to ambient temperature, a mixture of 3 ml of N,N-diethylaniline in 10 ml of phosphorus oxychloride is added dropwise and the reaction mixture is taken to reflux for 4 hours. After returning to ambient temperature, the reaction mixture is poured into a mixture of ice and water then sodium bicarbonate is added slowly to basic pH, followed by extracting with ethyl acetate, drying over magnesium sulphate and evaporating to dryness under reduced pressure (2 kPa). The residue is chromatographed on alumina eluting with a gradient of heptane-methylene chloride 100-0 to 80-20. 0.9 g (Yield=25%) of a brown oil is obtained.

TLC: Rf=0.25 (silicagel, eluent: heptane-ethyl acetate 95-5).

Synthesis of 6-[4-(1,2,3,4-tetrahydro-1,8-naphthyridin-7-yl)-1-piperidinyl]-5-isobutyl-4-chloro-pyrimidine

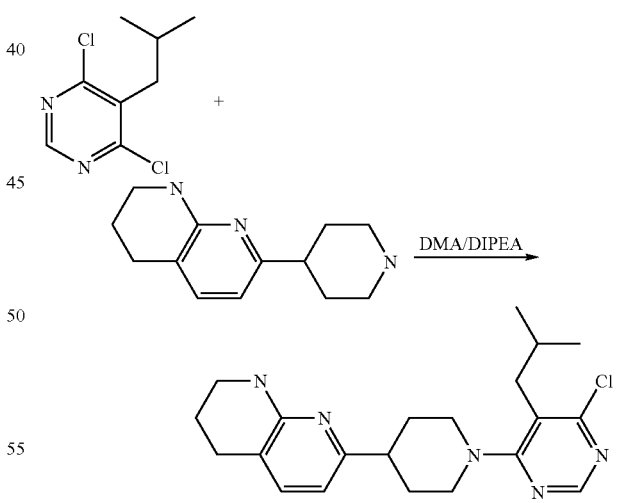

25 ml dimethylacetamide, 0.9 g (4.4 mmoles) of 4,6-dichloro-5-isobutyl-pyrimidine and 2 ml of diisopropylethylamine are added into a single-necked flask containing 0.95 g (4.4 mmoles) of 4-(1,2,3,4-tetrahydro-1,8-naphthyridin-7-yl)-1-piperidine released from its salt. This mixture is heated at 120° C. for 5 hours then concentrated to dryness under reduced pressure (2 kPa). The residue obtained is taken up in a mixture of water, ethyl acetate and a saturated solution of sodium bicarbonate. The organic phase is separated and the aqueous phase reextracted with ethyl acetate. The combined organic phases are dried over magnesium sulphate then the solvent is evaporated off under reduced pressure (2 kPa). The residue is chromatographed on silicagel eluting with a gradient of heptane-methylene chloride-ethyl acetate from 50-50-0 to 0-0-100. 1 g of expected product is obtained in the form of a beige solid. (Yield=60%)

TLC: Rf=0.25 [silicagel, eluent: ethyl acetate (100%)]

1H-NMR (CDCl3): δ 0.89(d, 6H,CH$_2$—CH—(CH$_3$)$_2$); 1.77 to 2.12 (m, 7H, NH—CH2-CH2-CH2, N—CH2-CH2-CH—CH2 and CH$_2$—CH—(CH$_3$)$_2$); 2.66 (d, 2H, —CH$_2$—CH—(CH$_3$)$_2$); 2.73 (t, 2H, NH—CH2-CH2-CH2); 2.61 to 2.77 (1H, masked, CH2-CH—CH2); 3.44 (m, 2H, NH—CH2-CH2-CH2); 3.03 and 3.87 (t and d, 4H, CH2-CH2-N—CH2-CH2); 5.11 (m, 2H, NH—CH2-CH2-CH2); 6.41 and 7.15 (2d, 2H, CH=CH naphthyridine); 8.40 (s, 1H, N=CH—N).

MS: 386.388 (MH+).

Synthesis of (1,1-dimethylethyl)3-[[5-isobutyl-6-[4-(1,2,3,4-tetrahydro-1,8-naphthyridin-7-yl)-1-piperidinyl]-4-pyrimidinyl]amino]-N-[(phenylmethoxy)carbonyl]alaninate

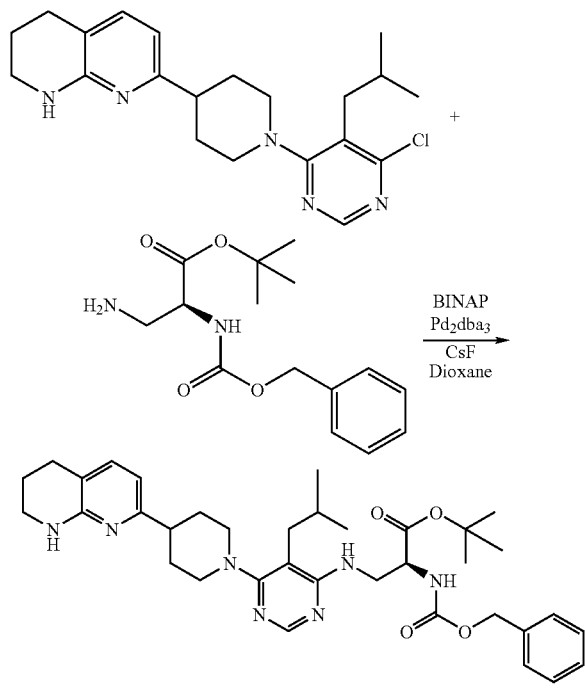

A mixture of 450 mg (1.17 mmoles) of 4-chloro-5-isobutyl-6-[4-(1,2,3,4-tetrahydro-1,8-naphthyridin-7-yl)-1-piperidinyl]-pyrimidine, 413 mg (1.4 mmoles) of (1,1-dimethylethyl)3-amino-N-[(phenylmethoxy)carbonyl]alaninate (prepared according to J. Med. Chem.(2001), 44(8), 1158-1176), 275 mg (1.81 mmoles) of caesium fluoride, 55 mg (0.060 mmole) of tris(dibenzylideneacetone)dipalladium(0), 75 mg (0.12 mmole) of 2,2'-bis(diphenyl-phosphino)-1,1'-binaphthyl in 35 ml of dioxane is heated under reflux for 20 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on alumina eluting with a gradient of methylene chloride-diisopropyl ether- ethyl acetate-methanol from 50-50-0-0 to 0-50-50-0 then 0-0-100-0 and finally 0-0-90-10. 630 mg (Yield=83%) of expected product is obtained in the form of an amorphous yellow solid.

TLC: Rf=0.12 (silicagel, eluent: ethyl acetate).

1H-NMR (CDCl3): δ 0.91(d, 6H,CH$_2$—CH—(CH$_3$)$_2$); 1.49 (s, 9H, tBu); 1.77 to 2.07 (m, 7H, —CH$_2$—CH—(CH$_3$)$_2$), NH—CH2-CH2-CH2 and N—CH2-CH2-CH—CH2); 2.32(d, 2H, —CH$_2$—CH—(CH$_3$)$_2$); 2.65 (bt, 1H, CH2-CH—CH2); 2.73 (t, 2H, NH—CH2-CH2-CH2); 2.95 (bt, 2H CH2-CH2-N—CH2-CH2); 3.44 (m 4H, CH2-CH2-N—CH2-CH2 and NH—CH2-CH2-CH2); 3.85 and 3.92 (2m, 2H, NH—CH$_2$—CH—NH); 4.45 (m, 1H, NH—CH$_2$—CH—NH); 5.14 (s, 2H, CH$_2$-Ph); 6.12 (d, 1H CH$_2$—CH$_2$—CH$_2$—NH); 6.43 (d, 1H, H naphthyridine); 7.16 (d, 1H, H naphthyridine), 7.37 (m, 5H, CH2Ph); 8.31 (s, 1H, N=CH—N);

MS: 644 (MH+); 588 (MH-tBu+); 454 (MH-COOCH2Ph+).

Synthesis of 3-[[5-isobutyl-6-[4-(1,2,3,4-tetrahydro-1,8-naphthyridin-7-yl)-1-piperidinyl]-4-pyrimidinyl]amino]-N-[(phenylmethoxy)carbonyl]alanine, bis(trifluoroacetate).

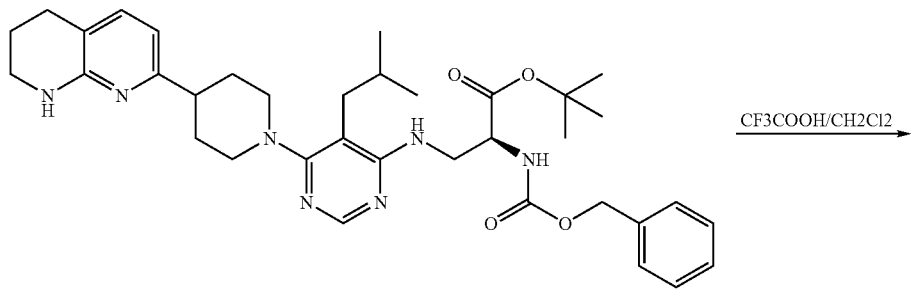

-continued

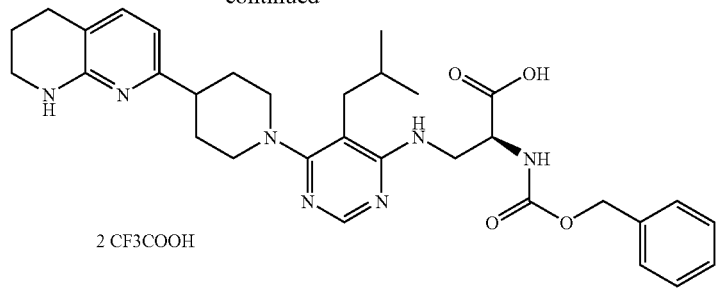

2 CF3COOH 620 mg (0.96 mmole) of (1,1-dimethylethyl) 3-[[5-isobutyl-6-[4-(1,2,3,4-tetrahydro-1,8-naphthyridin-7-yl)-1-piperidinyl]-4-pyrimidinyl]amino]-N-[(phenylmethoxy)carbonyl]alaninate in 50 ml of dichloromethane with 5 ml of trifluoroacetic acid is stirred at ambient temperature until the starting product disappears according to TLC (silicagel, eluent: CH2Cl2-MeOH-H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 525 mg (Yield=67% expressed as ditrifluoroacetate) of expected product is obtained in the form of a beige solid.

TLC: Rf=0.40 (silicagel, eluent: dichloromethane-methanol-water-acetic acid 85-15-2-2)

1H-NMR (DMSO d6): 0.83(d, 6H,CH$_2$—CH—(CH$_3$)$_2$); 1.60 to 2.05 (m, 7H, —CH$_2$—CH—(CH$_3$)$_2$), NH—CH2-CH2-CH2 and N—CH2-CH2-CH—CH2); 2.35(m, 2H, —CH$_2$—CH—(CH$_3$)$_2$); 2.65 to 2.87 (m, 3H, CH2-CH—CH2 and NH—CH2-CH2-CH2); 2.91 (bt, 2H CH2-CH2-N—CH2-CH2); 3.42 (m 4H, CH2-CH2-N—CH2-CH2 and NH—CH2-CH2-CH2); 3.57 and 3.84 (2m, 2H, NH—CH$_2$-CH—NH); 4.32 (m, 1H, NH—CH$_2$—CH—NH); 5.0 (s, 2H, CH$_2$-Ph); 6.68 (d, 1H, H naphthyridine); 7.37 (m, 5H, CH2Ph); 7.66 (d, 1H, H naphthyridine); 7.59 (d, 1H CH$_2$—CH$_2$—NH); 8.27 (s, 1H, N=CH—N).

MS: 588 (MH+); 454 (MH-COOCH2Ph+); 586- (M-H-); 478-(586-OCH2Ph-); 1173-(2M-H-)

[α$_D$] (0.75% CHCl3): +1.0.

Example 17

Synthesis of 5-methoxy-4,6-dihydroxy-pyrimidine

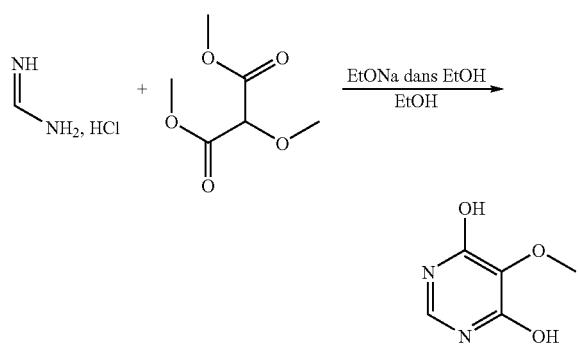

5 g (6.2 mmoles) of formamidine hydrochloride is added at 0° C. and in small quantities into a single-necked flask containing 30 ml of absolute ethanol and 90 ml of a solution of sodium ethylate at a concentration of 1.7 mol/l in ethanol. Stirring is maintained at ambient temperature for about twenty minutes, then 8.5 ml of dimethyl methoxymalonate is added dropwise. Stirring is maintained for 16 hours. The reaction mixture is then acidified with pure acetic acid to a pH between 4 and 5, then concentrated to dryness in the presence of cyclohexane. After impasting the crude product obtained is chromatographed on silicagel eluting with a mixture of methylene chloride-methanol (85-15)and 2% water-acetic acid (1-1). 9.5 g of the expected product is obtained containing a small quantity of sodium acetate salts.

TLC: Rf=0 [Silicagel, eluent: methylene chloride-methanol (85-15)and 2% of water-acetic acid (1-1).

1H-NMR (MeOD): δ 3.67 (s, CH3-O); 7.73 (s, 1H, N=CH—N) 2.00 (s, 3H, CH3-COO—)

HPLC/MS: (rt=0.5 min)

Synthesis of 4,6-dichloro-5-methoxy-pyrimidine:

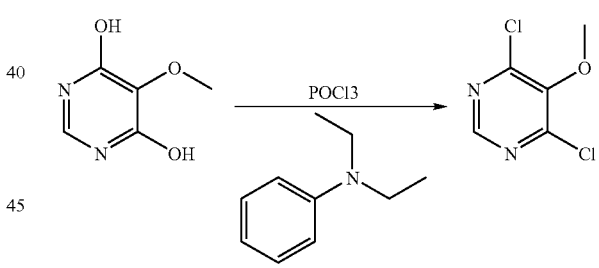

A mixture of 5 g (35.2 mmoles) of 5-methoxy-4,6-dihydroxy-pyrimidine and 40 ml of phosphorus oxychloride, is taken to reflux for one hour. After returning to ambient temperature, a mixture of 4.8 ml of N,N-diethylaniline and 18 ml of phosphorus oxychloride is added dropwise.

The mixture is again taken to reflux for 4 hours 30 minutes. After cooling down, the reaction mixture is poured slowly into a mixture of ice and water then neutralized by a saturated solution of sodium bicarbonate. This aqueous phase is extracted with ethyl acetate. The combined organic phases are dried over magnesium sulphate and evaporated to dryness under vacuum.

The residue obtained is purified on silica eluting with a mixture of cyclohexane and acetate (95-5).

2.5 g (Yield=40%) of expected product is obtained in the form of a white powder.

TLC: Rf=0.48 [Silicagel, eluent: cyclohexane-ethyl acetate (80-20)]

1H-NMR (MeOD): δ 4.00 (s, CH3-O); 8.55 (s, 1H, N=CH—N)

HPLC/MS: rt=1.3 min

Synthesis of 6-[4-(1,2,3,4-tetrahydro-1,8-naphthyridin-7-yl)-1-piperidinyl]-5-methoxy-4-chloro-pyrimidine

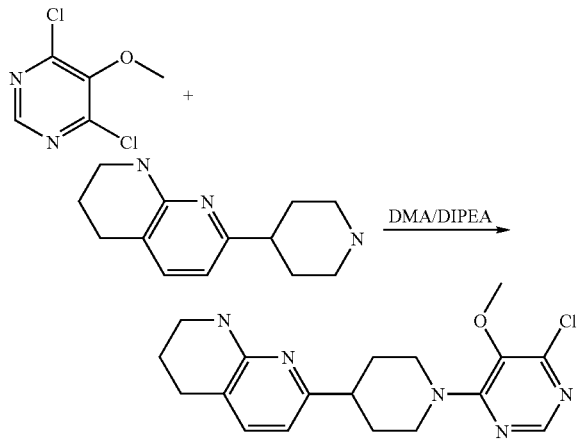

2.2 g (12.3 mmoles) of 4,6-dichloro-5-methoxy-pyrimidine solubilized in 25 ml of dimethylacetamide and 3640 μl of diisopropylethylamine are added into a single-necked flask containing 800 mg (3.68 mmoles) of 4-(1,2,3,4-tetrahydro-1,8-naphthyridin-7-yl)-1-piperidine released from its salt. This mixture is heated at 130° C. for 2 hours then concentrated to dryness under vacuum. The residue obtained is taken up in a mixture of water, ethyl acetate and a saturated solution of sodium bicarbonate. The organic phase is separated and the aqueous phase reextracted with ethyl acetate. The combined organic phases are dried over magnesium sulphate then the solvent is evaporated off under vacuum. The residue is chromatographed on alumina eluting with a mixture of cyclohexane and acetate (80-20). 900 mg (Yield=68%) of expected product is obtained in the form of a yellow powder.

Preparation of the naphthyridine in free amine form:

2.4 g of naphthyridine is displaced from its salt by 6 mass equivalents of basic amberlyst A21 resin (resin of R—NMe$_2$ type) in a CH$_2$Cl$_2$/MeOH/AcOEt mixture 1/1/1 under stirring for 30 minutes. The resin is washed beforehand and left to swell for 20 minutes in this solvent mixture. This operation must be repeated 3 times for the displacement of the salt to be complete. After filtration of the resin and evaporation of the solvents, 800 mg (3.68 mmoles) of free naphthyridine is obtained. (Yield=88%).

TLC: Rf0.4 [alumina, eluent: ethyl acetate cyclohexane (30-70)]

1H-NMR (MeOD): δ 1.75 to 1.95 (m, 6H, NH—CH2-CH2-CH2, N—CH2-CH2-CH—CH2); 2.70 (t, 1H, CH2-CH—CH2); 2.8 (m, 2H, NH—CH2-CH2-CH2); 3.15 and 3.75 (2m, 4H, CH2-CH2-N—CH2-CH2); 3.75 (s, CH3-O); 6.4 and 7.15 (2d, 2H, CH=CH naphthyridine); 8.1 (s, 1H, N=CH—N).

HPLC/MS: (rt=0.53 min and 2.56 min): 359(M); 360(MH+); 361 (M+2H++).

Synthesis of (1,1-dimethylethyl) 3-[[6-[4-(1,2,3,4-tetrahydro-1,8-naphthyridin-7-yl)-1-piperidinyl]-5-methoxy-4-pyrimidinyl]amino]-N-[(phenylmethoxy)carbonyl]alaninate

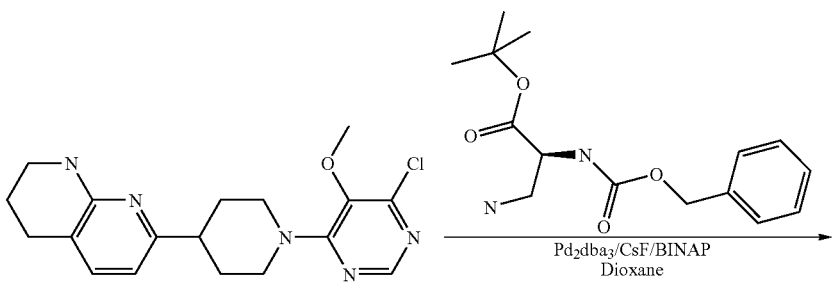

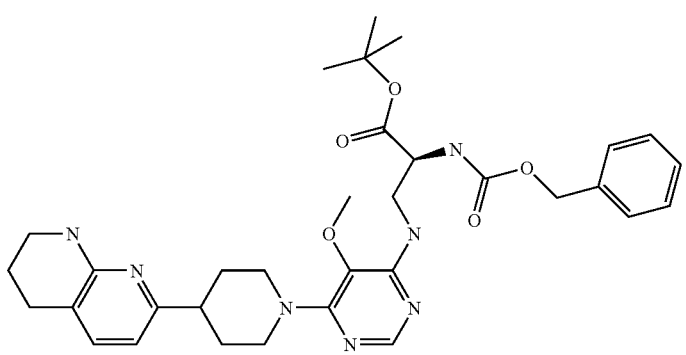

A mixture of 300 mg (0.83 mmoles) of 6-[4-(1,2,3,4-tetrahydro-1,8-naphthyridin-7-yl)-1-piperidinyl]-5-methoxy-4-chloro-pyrimidine and 295 mg (1. mmole) of (1,1-dimethylethyl) 3-amino-N-[(phenylmethoxy)carbonyl]alaninate (prepared according to J. Med. Chem. (2001), 44(8), 1158-1176), is heated under reflux for 3 hours 30 minutes in the presence of 177 mg (1.17 mmoles) of caesium fluoride, 52 mg (83 μmoles)of (2,2'-bis(diphenylphosphino)-1,1'-binaphthyl and 40 mg (42 μmoles) of tris-dibenzylideneacetone) dipalladium(o), in 10 ml of dioxane. The reaction mixture is then taken to temperature then 0.5 mmoles of (1,1-imethylethyl) 3-amino-N-[(phenylmethoxy)carbonyl]alaninate and 1.17 mmoles of caesium fluoride, 83 μmoles of (2,2'-bis(diphenylphosphino)-1,1'-binaphthyl and 42 μmoles of tris-dibenzylideneacetone) dipalladium(o) are added then the reaction mixture is taken to reflux for another 8 hours.

After cooling down the solution is concentrated to dryness then taken up in a mixture of water, ethyl acetate and a saturated solution of sodium bicarbonate. The organic phase is decanted and the aqueous phase is extracted with ethyl acetate. The combined organic phases are dried over magnesium sulphate and evaporated to dryness under vacuum. The residue is chromatographed on alumina with a gradient of isopropyl ether and ethyl acetate (70-30, 60-40, 50-50) ending with 100% ethyl acetate. The fractions containing the expected product are combined for a second purification on silicagel with a gradient of 100% ethyl acetate. The expected product is obtained in the form of a pale yellow oil which is taken up in an isopropyl ether and pentane mixture in order to produce 220 mg (Yield=43%) of a white powder.

TLC: Rf=0.3 (alumina eluent: isopropyl ether-ethyl acetate 60-40)

1H-NMR (MeOD): δ 1.46 (s, 9H, tBu); 1.80 (m, 2H, NH—CH2-CH2-CH2); 1.90 (m, 4H, N—CH2-CH2-CH—CH2); 2.65 (m, 1H, CH2-CH—CH2); 2.69 (t, 2H, NH—CH2-CH2-CH2); 2.95 and 3.78 (2m, 4H, CH2-CH2-N—CH2-CH2); 3.38 (t, 2H, NH—CH2-CH2-CH2); 3.59 (s, CH3-O); 4.35 (m, 1H, NH—CH2-CH—NH); 4.45 (d, 2H, NH—CH2-CH—NH); 5.03 and 5.12 (syst AB, 2H, O—CH2-Ph); 6.38 and 7.15 (2d, 2H, CH═CH naphthyridine); 7.32 (m, 5H, Ph); 7.90 (s, 1H, N═CH—N).

HPLC/MS: (rt=3.4 min): 618 (MH+); 562 (MH-tBu); 428 [MH-(tBu-Z+)]

Synthesis of corresponding acid

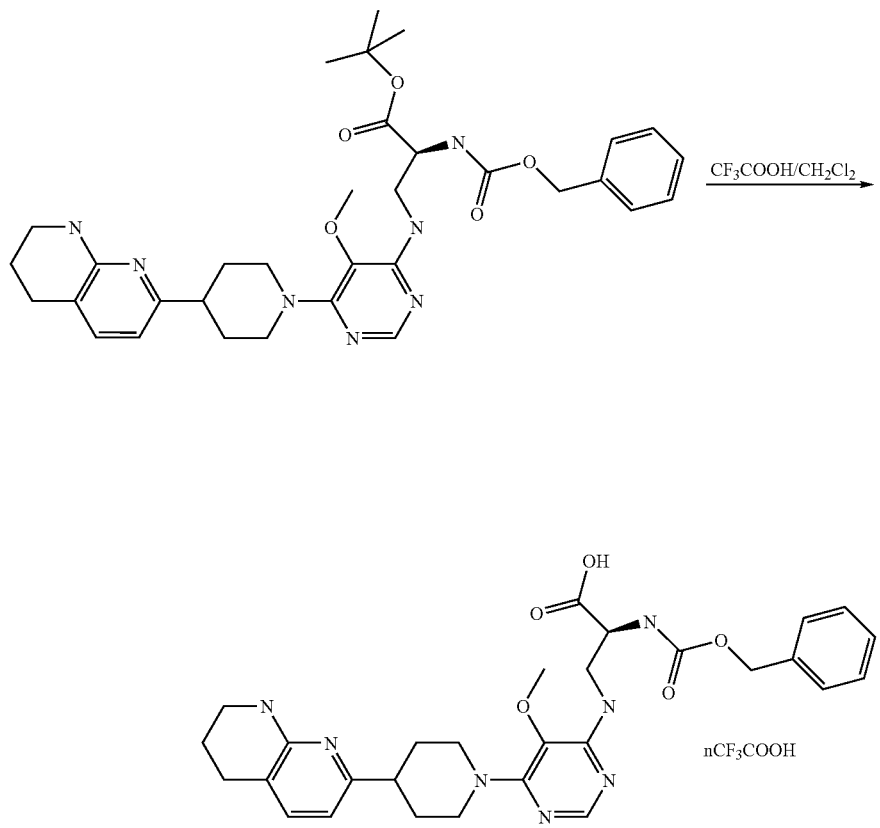

A mixture of 200 mg (0.32 mmoles) of (1,1-dimethylethyl) 3-[[5-methoxy-6-[4-(1,2,3,4-tetrahydro-1,8-naphthyridin-7-yl)-1-piperidinyl]-5-methyl-4-pyrimidinyl]amino]-N-[(phenyl methoxy)carbonyl]alaninate and 1.5 ml of trifluoroacetic acid in 15 ml of dichloromethane is stirred at ambient temperature for 8 hours. Then toluene is added and the mixture is evaporated to dryness. 350 mg of a yellow oil is obtained, this oil is taken up in a minimum amount of methylene chloride and precipitated from isopropyl ether, in this way the impure trifuoroacetate salt is obtained. Precipitation is repeated from ether to purification (checked by TLC). Finally 156 mg of the expected product (Yield=71%) is obtained in the form of a white powder.

TLC: Rf=0.4 (silicagel, eluent: dichloromethane-methanol-water-acetic acid 90-10-1-1).

1H-NMR (MeOD): δ 1.85 (m, 2H, NH—CH2-CH2-CH2); 2.00 (m, 4H, N—CH2-CH2-CH—CH2); 2.83 (t, 2H, NH—CH2-CH2-CH2); 3.90 (m, 1H, CH2-CH—CH2); 3.12 and 3.72 (2m, 4H, CH2-CH2-N—CH2-CH2); 3.52 (t, 2H, NH—CH2-CH2-CH2); 3.62 (s, 3H, CH3-O); 4.52 (m, 2H, NH—CH2-CH—NH); 4.60 (m, 1H, NH—CH2-CH—NH); 5.06 and 5.10 (syst AB, 2H, O—CH2-Ph); –6.65 and 7.62 (2d, 2H, CH=CH naphthyridine); 7.43 (m, 5H, Ph); 8.00 (s, 1H, N=CH—N).

HPLC/MS: (rt=0.5 min and 2.75 min): 562 (MH+); 428 [MH-(tBu-Z+)]; 428

Example 18

Synthesis of 4,6-dibromo-5-fluoro-pyrimidine

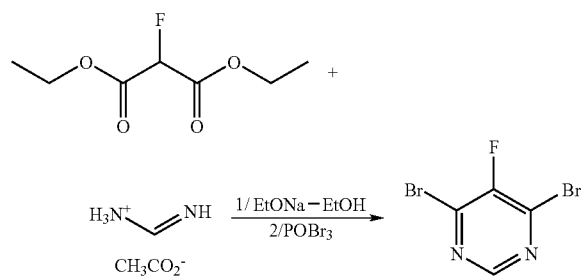

1/ 60.7 ml (168 mmoles) of a solution of sodium ethylate to 21% in the ethanol is added to a solution of 5.83 g (56 mmoles) of formamidine acetate in 300 ml of ethanol cooled down to 0° C. and the mixture is stirred for 30 minutes; then a solution of 10 g (56 mmoles) of diethyl fluoro malonate in 25 ml of ethanol is added at ambient temperature and the reaction mixture is stirred overnight, followed by cooling down to 0° C. then 17.85 ml of concentrated hydrochloric acid is added in order to adjust the pH to 6. The precipitate is filtered then washed successively with water, isopropanol, diethyl ether and finally pentane. 14.2 g (theory=7.3 g) of expected product and mineral salts are obtained used as they are for the following.

2/ A mixture of 14.2 g (56 mmoles) of 5-fluoro-4,6-dihydroxy-pyrimidine in 21 g of phosphorus oxybromide is taken to 200° C. for 3 hours. After returning to ambient temperature, the reaction mixture is taken up in a mixture of iced water and sodium bicarbonate and extracted with ethyl acetate, the organic phases are washed with water, dried over magnesium sulphate and evaporated to dryness under reduced pressure (2 kPa). The residue is chromatographed on silicagel eluting with a gradient of methylene chloride-heptane from 0-100 to 100-0. 850 mg (Yield=06%) of expected product is obtained in the form of beige solid used as it is for the following.

TLC: Rf=0.50 (silicagel, eluent: dichloromethane-heptane 50-50)

Synthesis 4-bromo-5-fluoro-6-[4-(1,2,3,4-tetrahydro-1,8-naphthyridin-7-yl)-1-piperidinyl]-pyrimidine A mixture of 840 mg (1.5 mmoles) of 1,2,3,4-tetrahydro-7-(4-piperidinyl)-1,8-naphthyridine, tris(trifluoroacetate) (prepared according to the Patents EP1065207 or WO 0078317) and 5 g of Amberlyst A-21 resin (origin Fluka 06424 washed beforehand with a dichloromethane-ethyl acetate-methanol solution 1-1-1) in 100 ml of a dichloromethane-ethyl acetate-methanol solution 1-1-1 is stirred at ambient temperature for 1 hour. The mixture is filtered and the resin washed with the ternary solution. The filtrate obtained is stirred at ambient temperature for 1 hour in the presence of 5 g of Amberlyst A-21 resin treated as previously. The filtrate thus obtained is concentrated to dryness under reduced pressure (2 kPa) producing 320 mg of free amine. 384 mg (1.5 mmoles) of 4,6-dibromo-5-fluoro-pyrimidine, 6 ml of dimethylacetamide and 1.5 ml of diisopropylethylamine are added to this residue and the reaction mixture is taken to 130° C. for 1.5 hours, followed by evaporating to dryness under reduced pressure (2 kPa). The residue is taken up in ethyl acetate, water and a saturated solution of sodium bicarbonate. The organic phase is separated, dried over magnesium sulphate and the solvent is evaporated off under reduced pressure (2 kPa). The residue is chromatographed on silicagel eluting with heptane-ethyl acetate 50-50. 300 mg (Yield=52%) of expected product is obtained in the form of an amorphous solid.

TLC: Rf=0. 15 (silicagel, eluent: heptane-ethyl acetate 50-50).

IR (CHCl3): 3440 (NH); 1573, 1542, 1503 cm-1 (Heterocycle)

1H-NMR (CDCl3): δ 1.82, 1.92 and 2.02(dt, t and d 6H, CH$_2$—CH$_2$—CH$_2$—NH and CH$_2$—CH—CH$_2$); 2.72 (t, 2H, CH$_2$—CH$_2$—CH$_2$—NH); 2.80 (bt, 1H, CH$_2$—CH—CH$_2$); 3.13 and 4.68 (bt and d, 4H, CH$_2$—CH$_2$—N—CH$_2$—CH$_2$); 3.42 (m, 2H, CH$_2$—CH$_2$—CH$_2$—NH); 5.00 (m, 1H NH); 6.37 (d, 1H, naphthyridine); 7.14 (d, 1H, naphthyridine); 8.11 ppm (s, N=CH—N).

MS: 392 (MH+).

Synthesis of (1,1-dimethylethyl) 3-[[5-fluoro-6-[4-(1,2,3,4-tetrahydro-1,8-naphthyridin-7-yl)-1-piperidinyl]-4-pyrimidinyl]amino]-N-[(phenylmethoxy)carbonyl]alaninate

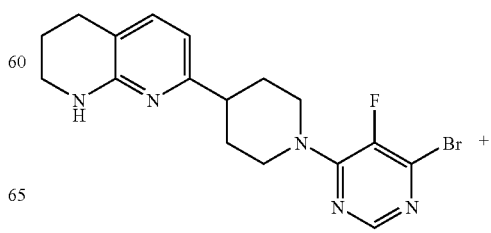

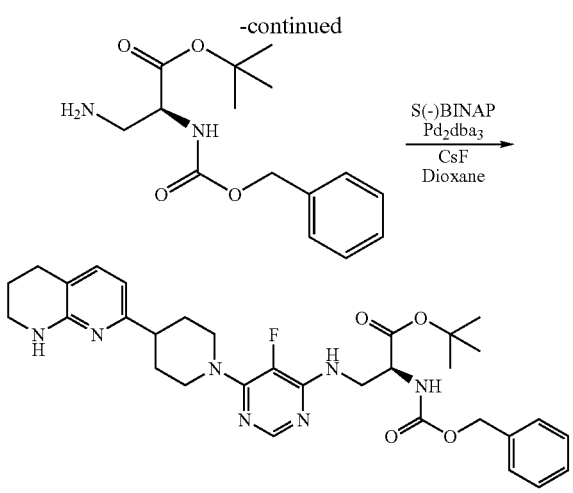

A mixture of 280 mg (0.72 mmole) of 4-bromo-5-fluoro-6-[4-(1,2,3,4-tetrahydro-1,8-naphthyridin-7-yl)-1-piperidinyl]-pyrimidine, 253 mg (0.86 mmole) of (1,1-dimethylethyl)3-amino-N-[(phenylmethoxy)carbonyl]alaninate (prepared according to J. Med. Chem. (2001), 44(8), 1158-1176), 152 mg (1.00 mmole) of caesium fluoride, 33 mg (0.036 mmole) of tris(dibenzylideneacetone)dipalladium(0), 45 mg (0.072 mmole) of 2,2'-bis(diphenyl-phosphino)-1,1'-binaphthyl in 50 ml of dioxane is heated under reflux for 6 hours. The reaction medium is cooled down then another 125 mg (0.43 mmole) of (1,1-dimethylethyl) 3-amino-N-[(phenylmethoxy)carbonyl]alaninate, 152 mg (1.0 mmole) of caesium fluoride, 33 mg (0.036 mmole) of tris(dibenzylideneacetone)dipalladium(0), and 45 mg (0.072 mmole) of 2,2'-bis(diphenyl-phosphino)-1,1'-binaphthyl are added and the reaction mixture is heated under reflux for 4 hours, followed by evaporating to dryness under reduced pressure (2 kPa). The residue is taken up in ethyl acetate, water and a saturated solution of sodium bicarbonate. The organic phase is separated, dried over magnesium sulphate and the solvent is evaporated off under reduced pressure (2 kPa). The residue is chromatographed on silicagel eluting with a gradient of heptane-ethyl acetate-methanol from 100-0-0 to 0-100-0 and finally 0-95-5. The product obtained is chromatographed a second time on alumina eluting with a heptane-methylene chloride mixture 50-50 then with an ethyl acetate-diisopropyl ether mixture 50-50. 300 mg (Yield=70%) of expected product is obtained in the form of a yellow oil.

TLC: Rf=0.35 (silicagel, eluent: ethyl acetate.

IR (CHCl3): 3439 (NH); 1718 (C═O); 1609.1503 cm-1 (Heterocycle+Aromatic+Amide).

1H-NMR (CDCl3): δ 1.47 (s, 9H, tBu); 1.70 to 2.05(m, 6H, CH$_2$—CH$_2$—CH$_2$—NH and CH$_2$—CH—CH$_2$); 2.73 (t, 2H, CH$_2$—CH$_2$—CH$_2$—NH); 2.80 (bt, 1H, CH$_2$—CH—CH$_2$); 3.01 and 3.90 (bt and m, 4H, CH$_2$—CH$_2$—N—CH$_2$—CH$_2$); 3.43 (m, 2H, CH$_2$—CH$_2$—CH$_2$—NH); 4.42 (m, 1H, NH—CH$_2$—CH—NH); 4.51 (bd, 2H, NH—CH$_2$—CH—NH); 5.11 (m, 1H NH); 5.14 (s, 2H, CH$_2$-Ph); 6.12 (m, 1H CH$_2$—CH$_2$—CH$_2$—NH); 6.37 (d, 1H, naphthyridine); 7.16 (d, 1H, naphthyridine); 7.35 (m, 5H, Ph); 7.98 ppm (s, N═CH—N).

MS: 606 (MH+); 550 (MH-tBu+); 416 (550-COOCH2Ph+), 604-[(M-H)]-, 650-[(604+HCOOH)]-, 496-[(604-OCH2Ph)]-.

[α$_D$] (1.0% CHCl3): +4.4

Synthesis of 3-[[5-fluoro-6-[4-(1,2,3,4-tetrahydro-1,8-naphthyridin-7-yl)-1-piperidinyl]-4-pyrimidinyl] amino]-N-[(phenylmethoxy)carbonyl]alanine, bis (trifluoroacetate)

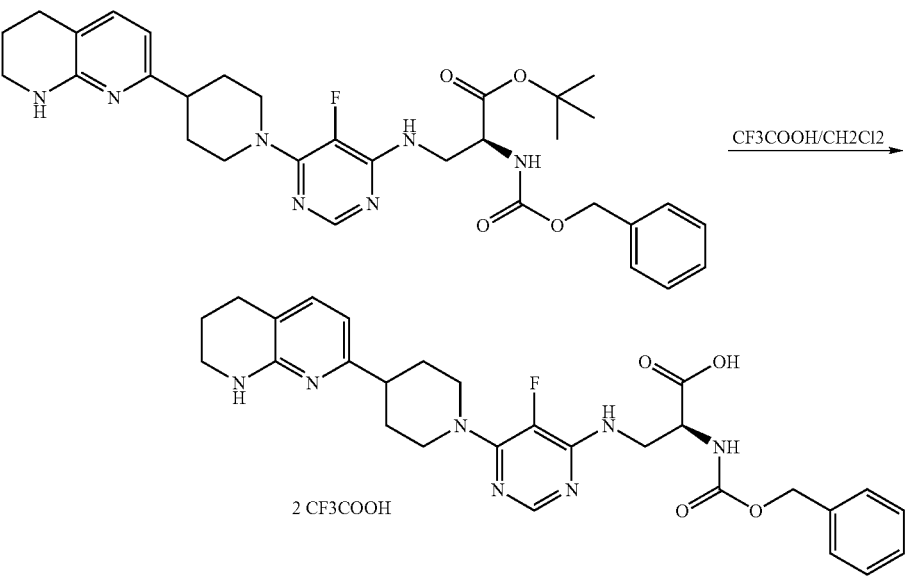

290 mg (0.48 mmole) of (1,1-dimethylethyl)3-[[5-fluoro-6-[4-(1,2,3,4-tetrahydro-1,8-naphthyridin-7-yl)-1-piperidinyl]-4-pyrimidinyl]amino]-N-[(phenylmethoxy)carbonyl] alaninate in 40 ml of dichloromethane with 4 ml of trifluoroacetic acid stirred at ambient temperature until the disappearance of the starting product according to TLC (silicagel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 310 mg (Yield=83% expressed as ditrifluoroacetate) of expected product is obtained in the form of a white solid.

TLC: Rf=0.44 (silicagel, eluent: dichloromethane-methanol-water-acetic acid 90-10-1-1)

MS: 550 (MH+); 416 (MH-COOCH2Ph+); 548–(M-H-); 440–(548–OCH2Ph-); 1097–(2M-H-)

[$\alpha_D$] (0.30% MeOH): −9.3.

Example 19

Synthesis of (1,1-dimethylethyl) 3-[5-ethyl-6-[4-(1,2,3,4-tetrahydro-1,8-naphthyridin-7-yl)-1-piperidinyl]-4-pyrimidinyl]amino]alaninate

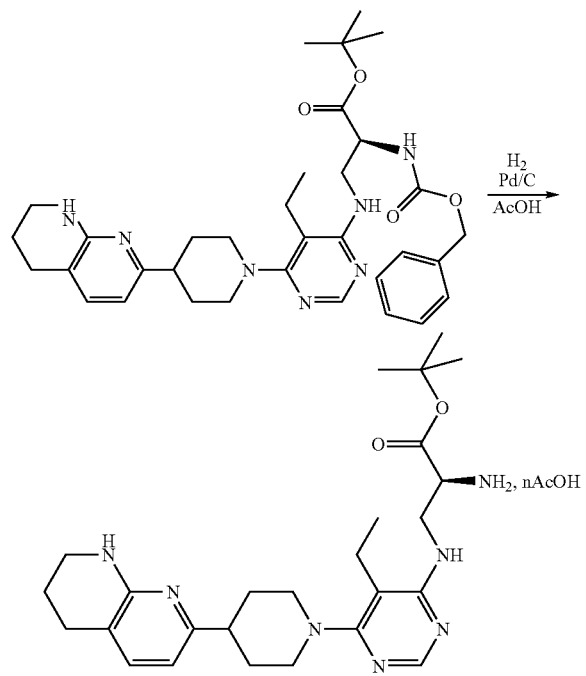

150 ml of 100% acetic acid and 300 mg of activated palladium on carbon (5-10%) are loaded into a single-necked flask containing 3 g (4.87 mmoles) of 3-[[6-[4-(1,2,3,4-tetrahydro-1,8-naphthyridin-7-yl)-1-piperidinyl]-5-ethyl-4-pyrimidinyl]amino]-N-[(phenylmethoxy)carbonyl]alanine. This mixture is purged under reduced pressure (2 kPa) then left under stirring at ambient temperature and under atmospheric pressure of hydrogen for 22 hours.

The heterogeneous medium obtained is filtered on clarcel. The filtrate is concentrated to dryness then taken up in a mixture of water, ethyl acetate and a saturated solution of sodium bicarbonate. The organic phase is extracted with ethyl acetate and dried over magnesium sulphate then the solvent is evaporated off under reduced pressure (2 kPa). 1.95 g of a pale yellow oil is obtained.

TLC: Rf=0.65 (silicagel, eluent: ethyl acetate-methanol-triethylamine 90-5-5)

1H-NMR (CDCl3): δ 1.09 (t, 3H, $CH_2$—$CH_3$); 1.35 (s, 9H, tBu); 1.75 (m, 6H, $CH_2$—CH—$CH_2$ and $CH_2$—$CH_2$—$CH_2$—NH); 2.44 (m, 2H, $CH_2CH_3$); 2.60 (t, 2H, $CH_2$—$CH_2$—$CH_2$—NH); 2.81 (m, 2H, $CH_2$—CH—$CH_2$ and NH—$CH_2$—CH—NH); 3.23 (m, 2H, $CH_2$—$CH_2$—$CH_2$—NH); 3.41 (m, 4H, $CH_2$—$CH_2$—N—$CH_2$—$CH_2$); 3.42 and 3.57 (2m, 2H, NH—$CH_2$—CH—NH); 6.25 (m, 2H, $CH_2$—$CH_2$—$CH_2$—NH and NH—$CH_2$—CH—NH); 6.30 and 7.04 (2d, 2H, H naphthyridine); 8.08 ppm (s, 1H, N═CH—N).

IR (CHCl3): 3439 (NH); 1726 (C═O); 1580, 1502 cm-1 (heterocycle).

MS: 482+ [MH]+; 426+ [MH+-tBu]+; 339+ [MH+-CH2CH(NH2)CO2tBu]+; 241.7+ [M+2H]2

[$\alpha_D$]: −3 (1% CHCl3)

Synthesis of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-[(adamantylmethoxy)carbonyl]alaninate

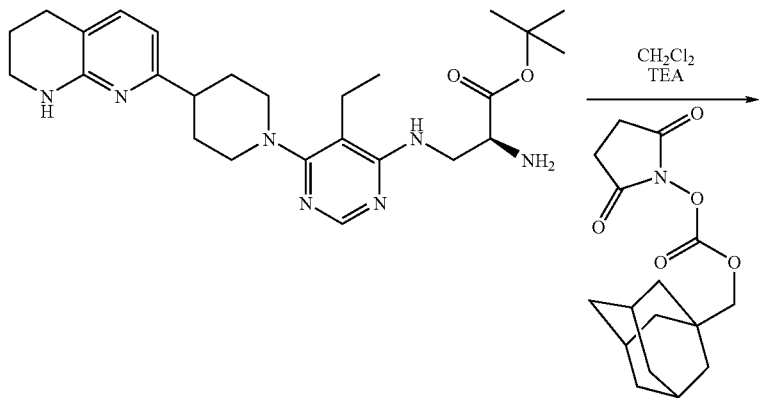

-continued

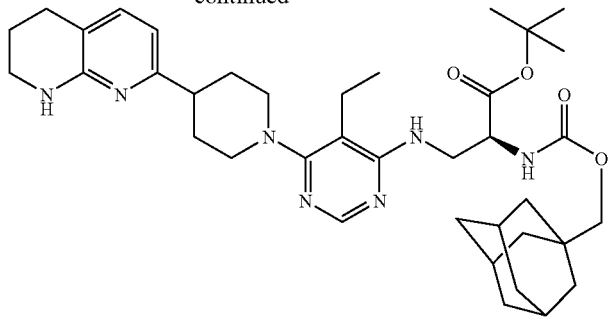

A mixture of 239 mg (0.49 mmoles) of (1,1-dimethylethyl) 3-[5-ethyl-6-[4-(1,2,3,4-tetrahydro-1,8-naphthyridin-7-yl)-1-piperidinyl]-4-pyrimidinyl]amino]alaninate, 152 mg (0.49 mmoles) of N-adamantylmethoxycarbonyloxysuccinimide and 0.104 ml (0.75 mmoles) of triethylamine in 50 ml of methylene chloride is stirred for 5 hours at ambient temperature. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on silicagel eluting with a gradient of methylene chloride 100% to methylene chloride-methanol 90-10. 77 mg (Yield=17%) of expected product is obtained in the form of a beige solid.

TLC: Rf=0.45 (silicagel, eluent: methylene chloride-methanol-acetic acid-water 90-10-1-1).

IR (CHCl3): 3437 (NH); 1711 (C=O); 1583, 1556, 1501 cm-1 (Heterocycle)

1H-NMR (DMSO-d6): δ 1.08 (t, 3H, $CH_2$—$CH_3$); 1.45 to 1.92 (m, 15H, adamantyl); 1.32 (s, 9H, tBu); 1.77 (m, 6H, $CH_2$—CH—$CH_2$ and $CH_2$—$CH_2$—$CH_2$—NH); 2.44 (q, 2H, $CH_2$—$CH_3$); 2.50 (m, 1H, $CH_2$—CH—$CH_2$); 2.61 (t, 2H, $CH_2$—$CH_2$—$CH_2$—NH); 2.82 and 3.44 (2m, 4H, $CH_2$—$CH_2$—N—$CH_2$—$CH_2$); 3.22 (m, 2H, $CH_2$—$CH_2$—$CH_2$—NH); 3.56 (s, 2H, O—$CH_2$-adam); 3.66 (m, 2H, NH—$CH_2$—CH—NH); 4.17 (q, 1H, NH—$CH_2$—CH—NH); 6.24 (s, 1H, $CH_2$—$CH_2$—$CH_2$—NH); 6.30 and 7.05 (2d, 2H, H naphthyridine); 6.37 (t, 1H, NH—$CH_2$—CH—NH); 7.44 (d, 1H, NH—$CH_2$—CH—NH); 8.10 ppm (s, N=CH—N).

MS: 674 (MH+); 618 (MH-tBu+); 426 (618-COOCH2adam+); 337.7 (M2H++); 718- (M-H-HCOOH); 672-(M-H).

[α]$_D$: +2.5 (1% CHCl3).

Synthesis of 3-[[5-ethyl-6-[4-(1,2,3,4-tetrahydro-1,8-naphthyridin-7-yl)-1-piperidinyl]-4-pyrimidinyl]amino]-N-[(adtamantylmethoxy)carbonyl]alanine

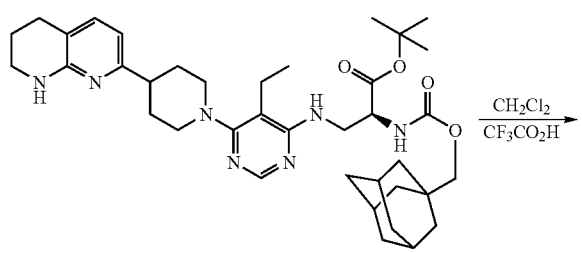

-continued

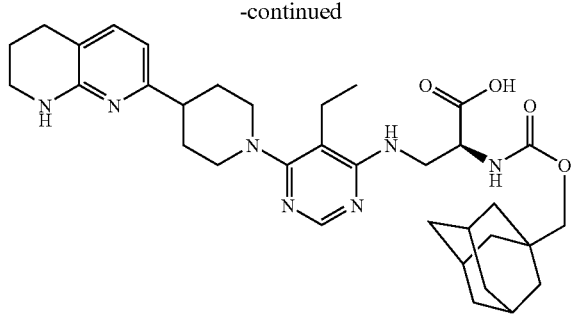

130 mg (0.19 mmoles) of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-[(adamantylmethoxy)carbonyl]alaninate in 20 ml of dichloromethane with 2 ml of trifluoroacetic acid is stirred at ambient temperature until the starting product disappears according to TLC (silicagel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 368 mg (Yield=61% expressed as ditrifluoroacetate) of expected product is obtained in the form of an amorphous solid.

TLC: Rf=0.35 (silicagel, eluent: dichloromethane-methanol-water-acetic acid 90-10-1-1)

IR (CHCl3): 3401 (NH); 1668 (C=O); 1581, 1492 cm-1 (Heterocycle)

1H-NMR (DMSO-d6): δ 1.08 (t, 3H, $CH_2$—$CH_3$); 1.45 to 1.92 (m, 15H, adamantyl); 1.76 (m, 6H, $CH_2$—CH—$CH_2$, $CH_2$—$CH_2$—$CH_2$—NH); 2.43 (q, 2H, $CH_2$—$CH_3$); 2.50 (m, 1H, $CH_2$—$CH_2CH_2$); 2.60 (t, 2H, $CH_2$—$CH_2$—$CH_2$—NH); 2.82 and 3.45 (2m, 4H, $CH_2$—$CH_2$—N—$CH_2$—$CH_2$); 3.23 (m, 2H, $CH_2$—$CH_2$—$CH_2$—NH); 3.49 and 3.58 (m, 2H, O—$CH_2$-adam); 3.56 and 3.76 (m, 2H, NH—$CH_2$—CH—NH); 4.18 (m, 1H, NH—$CH_2$—CH—NH); 6.26 (s, 1H, $CH_2$—$CH_2$—$CH_2$—NH); 6.30 and 7.05 (2d, 2H, H naphthyridine); 6.44 (m, 1H, NH—$CH_2$—CH—NH); 7.25 (d, 1H, NH—$CH_2$—CH—NH); 8.11 ppm (s, N=CH—N).

MS: 618 (MH+); 426 (MH-COOCH2Ph+); 1235 (2MH+); 309.8 (M2H++); 616-(M-H-)

[α$_D$] (0.7% CH3OH): −2.8

Example 20

Synthesis of (1,1-dimethylethyl)3-[5-ethyl-6-[4-(1,2,3,4-tetrahydro-1,8-naphthyridin-7-yl)-1-piperidinyl]-4-pyrimidinyl]amino]alaninate

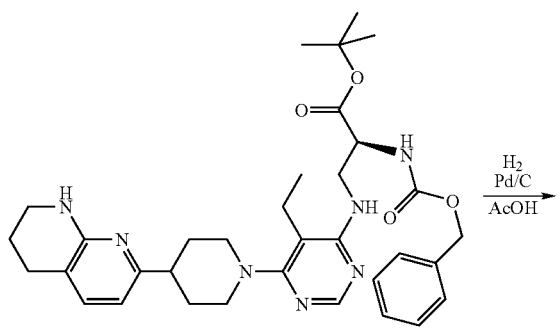

150 ml of 100% acetic acid and 300 mg of palladium on activated carbon (5-10%) is loaded into a single-necked flask containing 3 g (4.87 mmoles) of 3-[[6-[4-(1,2,3,4-tetrahydro-1,8-naphthyridin-7-yl)-1-piperidinyl]-5-ethyl-4-pyrimidinyl]amino]-N-[(phenylmethoxy)carbonyl]alanine. This mixture is purged under reduced pressure (2 kPa) then left under stirring at AT under atmospheric pressure of hydrogen for 22 hours.

The heterogeneous medium obtained is filtered on clarcel. The filtrate is concentrated to dryness under reduced pressure (2 kPa) then taken up in a mixture of water, ethyl acetate and a saturated solution of sodium bicarbonate. The organic phase is extracted with ethyl acetate and dried over magnesium sulphate then the solvent is evaporated off under reduced pressure (2 kPa). 1.95 g of a pale yellow oil is obtained.

TLC rf=0.65 (silicagel eluent AcOEt-MeOH-TEA=90-5-5)

$\alpha_d=-3$ (1% CHCl$_3$)

1H-NMR (CDCl3): δ 1.09 (t, 3H, CH$_2$—CH$_3$); 1.35 (s, 9H, tBu); 1.75 (m, 6H, CH$_2$—CH—CH$_2$ and CH$_2$—CH$_2$—CH$_2$—NH); 2.44 (m, 2H, CH$_2$—CH$_3$); 2.60 (t, 2H, CH$_2$—CH$_2$—CH$_2$—NH); 2.81 (m, 2H, CH$_2$—CH—CH$_2$ and NH—CH$_2$—CH—NH); 3.23 (m, 2H, CH$_2$—CH$_2$' CH$_2$—NH); 3.41 (m, 4H, CH$_2$—CH$_2$—N—CH$_2$—CH$_2$); 3.42 and 3.57 (2m, 2H, NH—CH$_2$—CH—NH); 6.25 (m, 2H, CH$_2$—CH$_2$—CH$_2$—NH and NH—CH$_2$—CH—NH); 6.30 and 7.04 (2d, 2H, H naphthyridine); 8.08 ppm (s, 1H, N=CH—N).

IR (CHCl3) 3439 (NH); 1726 (C=O); 1580–1502 (heterocycle)

HPLC/MS 482$^+$ [MH]$^+$; 426$^+$ [MH$^+$-tBu]$^+$; 339$^+$ [MH$^+$-CH$_2$CH(NH$_2$)CO$_2$tBu]$^+$; 241.7$^+$ [M+2H]$^2$

Examples 21 to 31

Example 28

Stage a

Synthesis of (1,1-dimethylethyl)3-[[5-ethyl-6-[4-(1,2,3,4-tetrahydro-1,8-naphthyridin-7-yl)-1-piperidinyl]-4-pyrimidinyl]amino]-N-(4-methoxy-benzenesulphonyl)alaninate

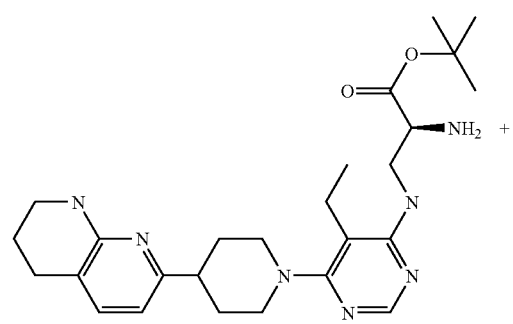

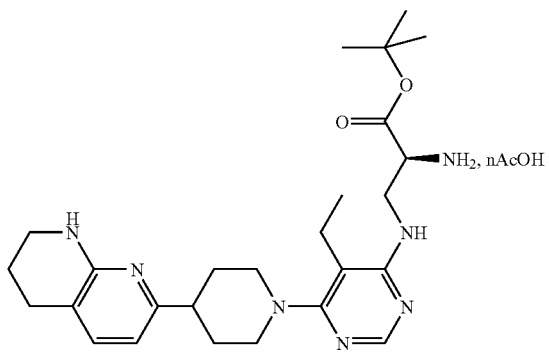

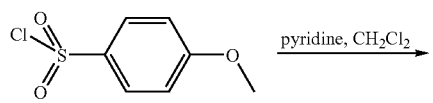

-continued

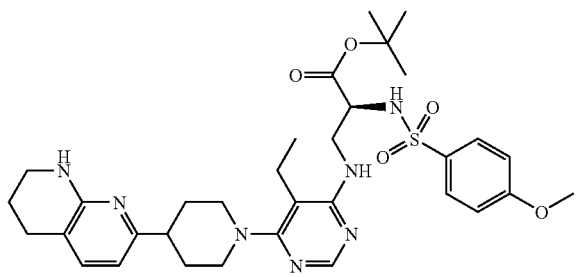

64.3 mg (0.31 mmoles) of 4-methoxy-benzenesulphonyl chloride in solution in 3 ml of dichloromethane is added to a mixture of 150 mg (0.31 mmoles) of (1,1-dimethylethyl)3-[5-ethyl-6-[4-(1,2,3,4-tetrahydro-1,8-naphtiridin-7-yl)-1-piperidinyl]-4-pyrimidinyl]amino]alaninate in solution in 6 ml of dichloromethane and 650 μl of pyridine. The reaction mixture is stirred at ambient temperature for 5 hours. Then, the solvent is evaporated off under reduced pressure (2 kPa) and the residue is chromatographed on silicagel with the following eluent: ethyl acetate-dichloromethane/methanol (95/5) 50-50 to ethyl acetate-methanol 90-10. 55.8 mg (Yield=28%) of expected product is obtained.

TLC: Rf=0.63 (silicagel, eluent: dichloromethane-methanol-water-acetic acid 85-15-2-2)

1H-NMR (CDCl$_3$): δ 1.21 (t, 3H, CH2-CH3); 1.30 (s, 9H, tBu); 1.92 and 2.02 (2m, 6H, N—CH2-CH2-CH—CH2-CH2, CH2-CH2-CH2-NH); 2.48 (q, 2H, CH2-CH3); 2.72 (m, 3H, N—CH2-CH2-CH—CH2-CH2, CH2-CH2-CH2-NH); 2.97 and 3.61 (2m, 4H, N—CH2-CH2-CH—CH2-CH2); 3.45 (m, 2H, CH2-CH2-CH2-NH); 3.74 and 3.86 and 3.95 (3m, 6H, NH—CH2-CH—NH, OCH3); 4.95 (t, 1H, mobile NH); 5.92 (bd, 1H, mobile NH); 6.43 and 7.20 (2d, 2H, CH═CH naphthyridine); 6.95 and 7.79 (2d, 4H, CH═CH benzene); 8.29 (s, 1H, N═CH—N).

MS: 652(MH+).

Stage b

Synthesis of 3-[[5-ethyl-6-[4-(1,2,3,4-tetrahydro-1,8-naphthyridin-7-yl)-1-piperidinyl]-4-pyrimidinyl]amino]-N-(4-methoxy-benzenesulphonyl)alanine

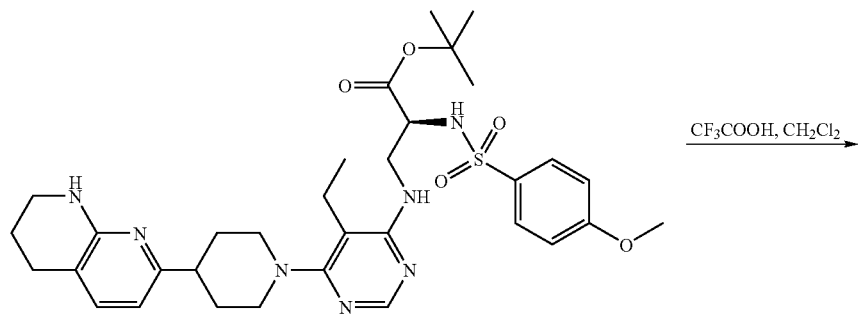

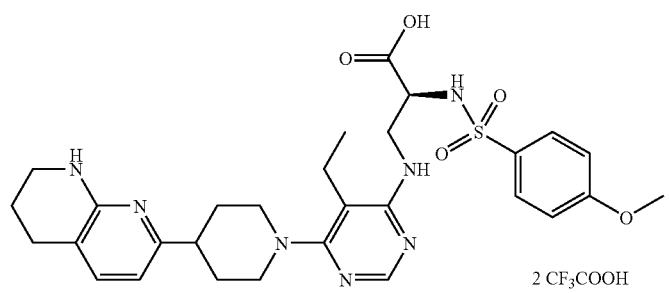

55.8 mg (0.086 mmoles) of (1,1-dimethylethyl)3-[[5-ethyl-6-[4-(1,2,3,4-tetrahydro-1,8-naphthyridin-7-yl)-1-piperidinyl]-4-pyrimidinyl]amino]-N-(4-methoxy-benzene-sulphonyl)alaninate in 5 ml of dichloromethane with 0.5 ml of trifluoroacetic acid is stirred at ambient temperature until the starting product disappears according to TLC (silicagel, eluent: CH2Cl2-MeOH-H2O—AcOH 85-15-2-2). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 59.8 mg (Yield=85% expressed as ditrifluoroacetate) of expected product is obtained.

TLC: Rf=0.33 (silicagel, eluent: dichloromethane-methanol-water-acetic acid 85-15-2-2).

1H-NMR (MeOD): δ 1.22 (t, 3H, CH2-CH3); 1.96 and 2.10 (2m, 6H, N—CH2-CH2-CH—CH2-CH2, CH2-CH2-CH2-NH); 2.55 (q, 2H, CH2-CH3); 2.85 (t, 2H, CH2-CH2-CH2-NH); 2.95 (m, 1H, N—CH2-CH2-CH—CH2-CH2); 3.20 and 3.67 and 3.92 (3m, 6H, N—CH2-CH2-CH—CH2-CH2, NH—CH2-CH—NH); 3.51 (m, 2H, CH2-CH2-CH2-NH); 4.24 (m, 1H, NH—CH2-CH—NH); 6.71 and 7.64 (2d, 2H, CH=CH naphthyridine); 6.99 and 7.74 (2d, 4H, CH=CH benzene); 8.27 (s, 1H, N=CH—N).

MS: 596(MH+).

General operating method for the preparation of sulphonamides

Stage a

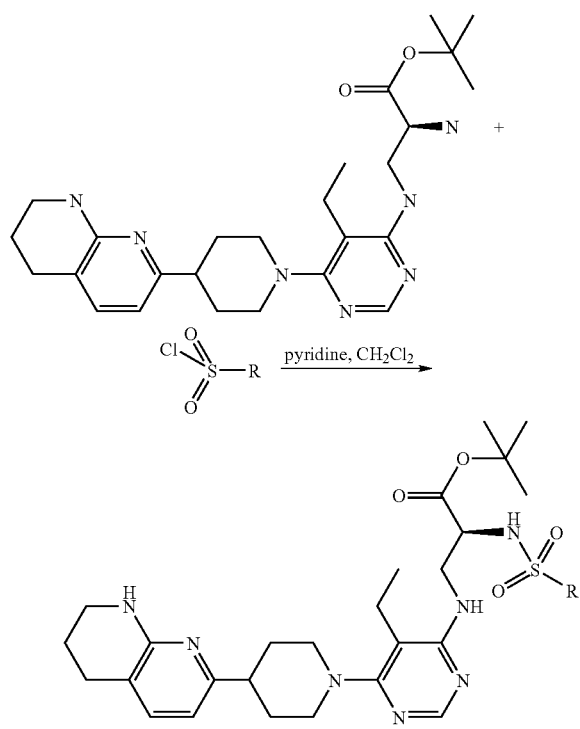

0.31 mmoles (mass $m_x$) of sulphonyl chloride in solution in 3 ml of dichloromethane is added to a mixture of 150 mg (0.31 mmoles) of (1,1-dimethylethyl)3-[5-ethyl-6-[4-(1,2,3,4-tetrahydro-1,8-naphtiridin-7-yl)-1-piperidinyl]-4-pyrimidinyl]amino]alaninate in solution in 6 ml of dichloromethane and 650 μl of pyridine. The reaction mixture is stirred at ambient temperature for 5 hours. Then, the solvent is evaporated off under reduced pressure (2 kPa) and the residue is chromatographed on silicagel with the following eluent: ethyl acetate-dichloromethane/methanol(95/5) 50-50 to ethyl acetate-methanol 90-10. A mass $m_y$ of expected product is obtained.

TLC: Rf (eluent: dichloromethane-methanol-water-acetic acid 85-15-2-2).

Stage b

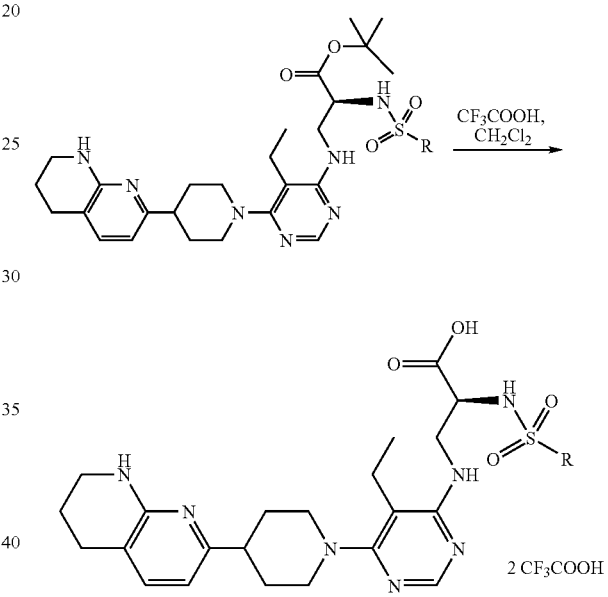

A mass $m_y$ of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N—(R-sulphonyl)alaninate in 5 ml of dichloromethane with 0.5 ml of trifluoroacetic acid is stirred at ambient temperature until the starting product disappears according to TLC (silicagel, eluent: CH2Cl2-MeOH—H2O—AcOH 85-15-2-2). Toluene is added and the reaction mixture is evaporated to dryness under reduced pressure (2 kPa). The residue is solubilized in the minimum amount of dichloromethane with a little methanol then poured into diisopropyl ether. The precipitate is filtered. A mass mi of expected product is obtained.

TLC: Rf (eluent: dichloromethane-methanol-water-acetic acid 85-15-2-2).

| Sulphonyl chloride | $M_x$ (mg) | Ester Formed | $M_y$ (mg) | Yield | MS (MH+) | Rf |
|---|---|---|---|---|---|---|
| Example 21 | 47.1 | | 30 | 22 | 672 | 0.61 |
| Example 22 | 40.4 | | 38.7 | 29 | 640 | 0.63 |
| Example 23 | 59.3 | | 48 | 24 | 636 | 0.69 |

-continued

| | Sulphonyl chloride | $M_x$ (mg) | Ester Formed | $M_y$ (mg) | Yield | MS (MH+) | Rf |
|---|---|---|---|---|---|---|---|
| Example 24 | 3-chloropropylsulfonyl chloride | 55.1 | (structure) | 18.4 | 10 | 622–624 | 0.65 |
| Example 25 | 4-chlorobenzenesulfonyl chloride | 65.6 | (structure) | 57.6 | 28 | 656–659 | 0.67 |
| Example 26 | biphenyl-4-sulfonyl chloride | 78.6 | (structure) | 70 | 32 | 698 | 0.67 |

-continued
| | $M_x$ (mg) | Ester Formed | $M_y$ (mg) | Yield | MS (MH+) | Rf |
|---|---|---|---|---|---|---|
| Sulphonyl chloride | | | | | | |
| Example 27 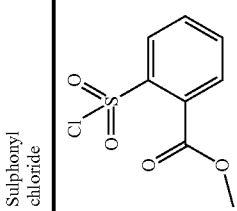 | 73.0 | 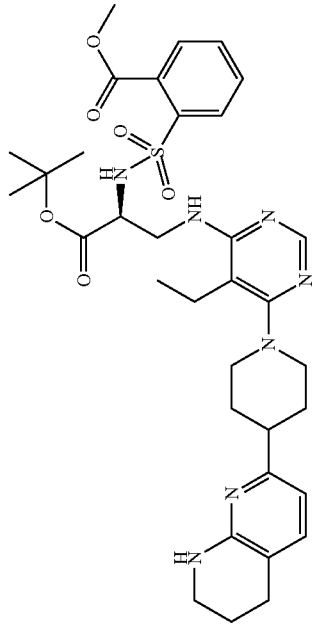 | 49.3 | 23 | 680 | 0.67 |
| Example 29 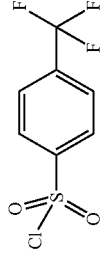 | 76.1 | 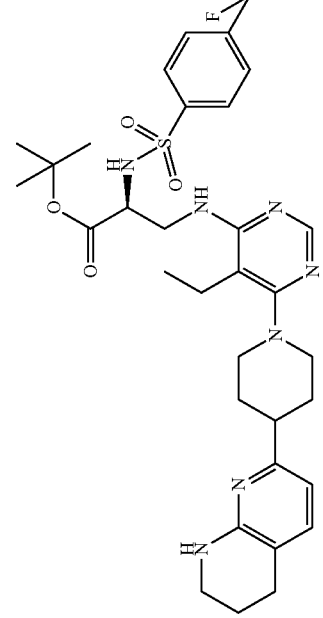 | 63.4 | 30 | 690 | 0.63 |
| Example 30 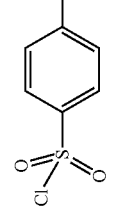 | 81.7 | 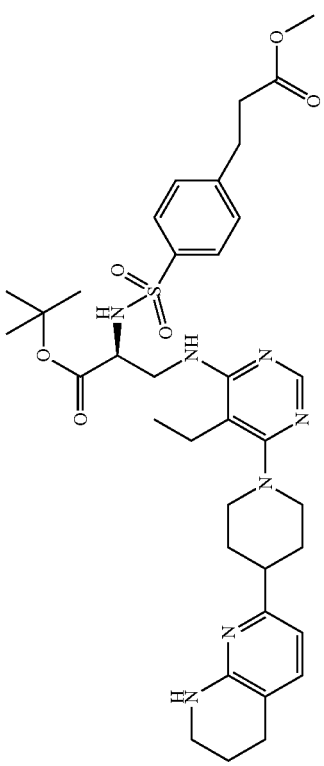 | 21.4 | 10 | 708 | 0.63 |

-continued
| | Sulphonyl chloride | $M_x$ (mg) | Ester Formed | $M_y$ (mg) | Yield | MS (MH+) | Rf |
|---|---|---|---|---|---|---|---|
| Example 31 |  | 62.7 | | 56.3 | 28 | 647 | 0.65 |
$M_x$: mass of sulphonyl chloride introduced.
$M_y$: mass of ester obtained

|  | Acid obtained | FW (free base) | free base + 2TFA | M_z (mg) | MS (MH+) | Rf |
|---|---|---|---|---|---|---|
| Example 21 | (structure with naphthalenesulfonyl group) · 2TFA | 615.76 | 843.76 | 20.8 | 616 | 0.4 |
| Example 22 | (structure with 4-fluorophenylsulfonyl group) · 2TFA | 583.69 | 811.69 | 31.2 | 584 | 0.33 |
| Example 23 | (structure with benzylsulfonyl group) · 2TFA | 579.73 | 807.73 | 45.4 | 580 | 0.3 |
| Example 24 | (structure with 3-chloropropylsulfonyl group) · 2TFA | 566.13 | 794.13 | 11.6 | 566–568 | 0.26 |
| Example 25 | (structure with 4-chlorophenylsulfonyl group) · 2TFA | 600.14 | 828.14 | 58.3 | 600–601 | 0.3 |

-continued
| Acid obtained | | FW (free base) | free base + 2TFA | $M_z$ (mg) | MS (MH+) | Rf |
|---|---|---|---|---|---|---|
| Example 26 | 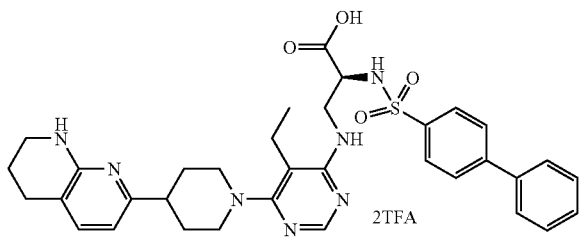 | 641.8 | 869.8 | 56.6 | 642 | 0.37 |
| Example 27 | 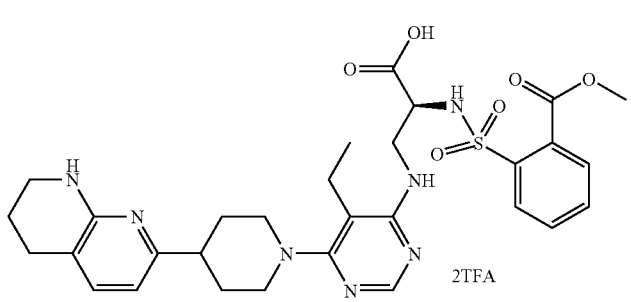 | 623.74 | 851.74 | 41.2 | 624 | 0.37 |
| Example 29 | 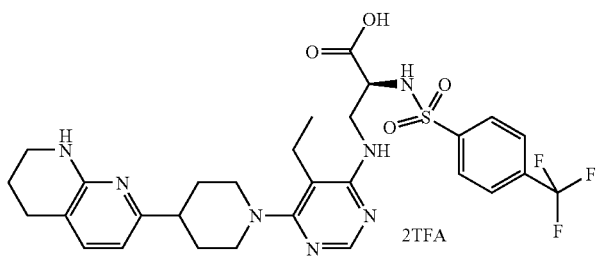 | 633.7 | 861.7 | 59.8 | 634 | 0.33 |
| Example 30 | 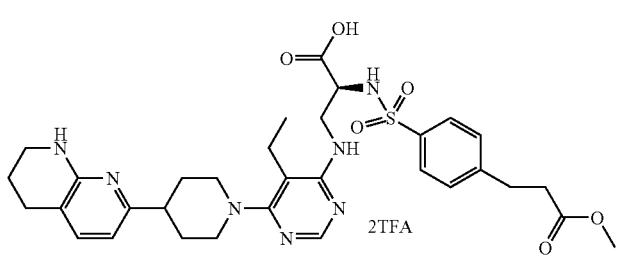 | 651.79 | 879.79 | 48.5 | 652 | 0.35 |
| Example 31 | 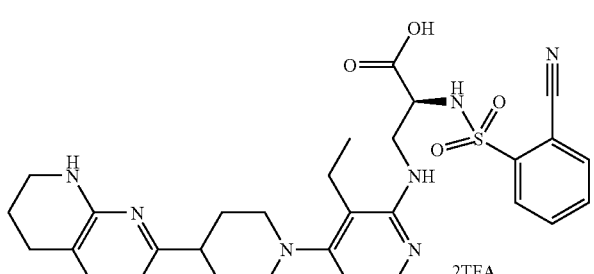 | 590.71 | 818.71 | 28 | 591 | 0.26 |
$M_z$: mass of acid obtained
$M_y$: mass of ester obtained

Example 32

Synthesis of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-(1-naphthalenesulphonyl)alaninate

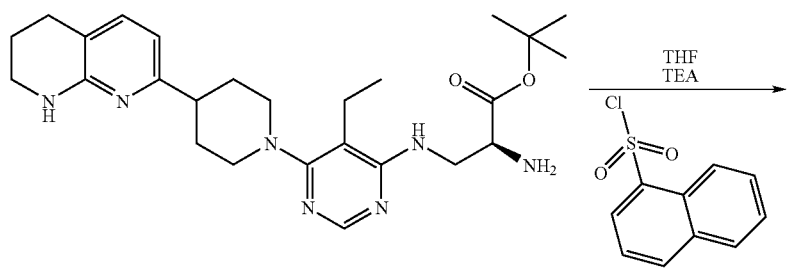

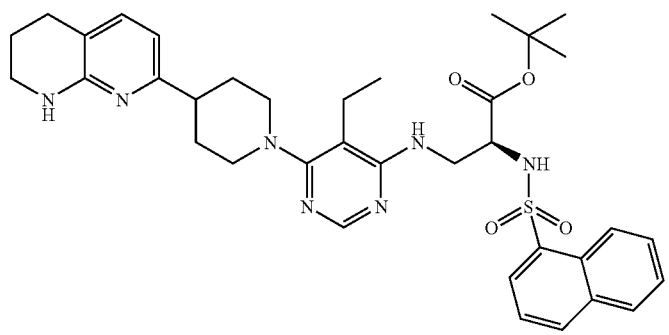

A mixture of 239 mg (0.49 mmoles) of (1,1-dimethylethyl) 3-[5-ethyl-6-[4-(1,2,3,4-tetrahydro-1,8-naphthyridin-7-yl)-1-piperidinyl]-4-pyrimidinyl]amino]alaninate, 113 mg (0.5 mmoles) of 1-naphthalenesulphonyl chloride and 0.104 ml (0.75 mmoles) of triethylamine in 50 ml of tetrahydrofuran is stirred for 5 hours at ambient temperature. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on alumina eluting with a gradient of heptane-ethyl acetate 75-25 to 0-100. 220 mg (Yield=67%) of expected product is obtained in the form of a white solid.

TLC: Rf=0.10 (silicagel, eluent: methylene chloride-methanol-acetic acid-water 90-10-1-1).

IR (CHCl3): 3440 (NH); 1728 (C=O); 1583, 1555, 1503 cm-1 (Heterocycle+aromatic)

1H-NMR (CDCl3): δ 1.02 (t, 3H, $CH_2CH_3$); 1.15 (s, 9H, tBu); 1.81 to 2.03(m, 6H, $CH_2$—CH—$CH_2$ and $CH_2$—$CH_2$—$CH_2$—NH); 2.23 and 2.31 (2q, 2H, $CH_2$—$CH_3$); 2.67 (t, 1H, $CH_2$—CH—$CH_2$); 2.72 (t, 2H, $CH_2$—$CH_2$—$CH_2$—NH); 2.93 and 3.56 (bt and bd, 4H, $CH_2$—$CH_2$—N—$CH_2$—$CH_2$); 3.43 (m, 2H, $CH_2$—$CH_2$—CH—NH); 3.66 and 3.76 (2m, 2H, NH—$CH_2$—CH—NH); 3.97 (m, 1H, NH—$CH_2$—CH—NH); 4.73 (t, 1H, t, 1H, NH—$CH_2$—CH—NH); 6.55 (s, 1H, $CH_2$—$CH_2$—$CH_2$—NH); 6.42 and 7.05 (2d, 2H, H naphthyridine); 7.51 (t, 1H, H3 1-SO2naphthyl); 7.57 and 7.62 (2t, 2H, H6 and H7 1-SO2naphthyl); 7.90 (d, 1H, H2 1-SO2naphthyl); 8.02 (d, 1H, H4 1-SO2naphthyl); 8.22 (m, 2H, N=CH—N and H5 1-SO2naphthyl); 8.61 ppm (m, 1H, H8 1-SO2naphthyl).

MS: 672 (MH+); 426 (616–SOOnaphth+); 670–(M-H).
[α]$_D$: +3.3 (1% CHCl3).

Synthesis of 3-[[5-ethyl-6-[4-(1,2,3,4-tetrahydro-1,8-naphthyridin-7-yl)-1-piperidinyl]-4-pyrimidinyl]amino]- N-(1-naphthalenesulphonyl)alanine 3.20 (m, 2H, CH$_2$—CH$_2$—CH$_2$—NH); 3.50 (m, 2H, CH—CH$_2$—CH$_2$—N); 3.66 and 3.76 (2m, 2H, NH—CH$_2$—CH—NH); 3.97 (t, 1H, NH—CH$_2$—CH—NH); 6.26 (s, 1H, CH$_2$—CH$_2$—CH$_2$—NH); 6.31 and 7.06 (2d, 2H, H naphthyridine); 7.55 (t, 1H, H3 1-SO2naphthyl); 7.62 (m, 2H, H6 and H7 1-SO2naphthyl); 7.96 ppm (s, N=CH—N); 8.02

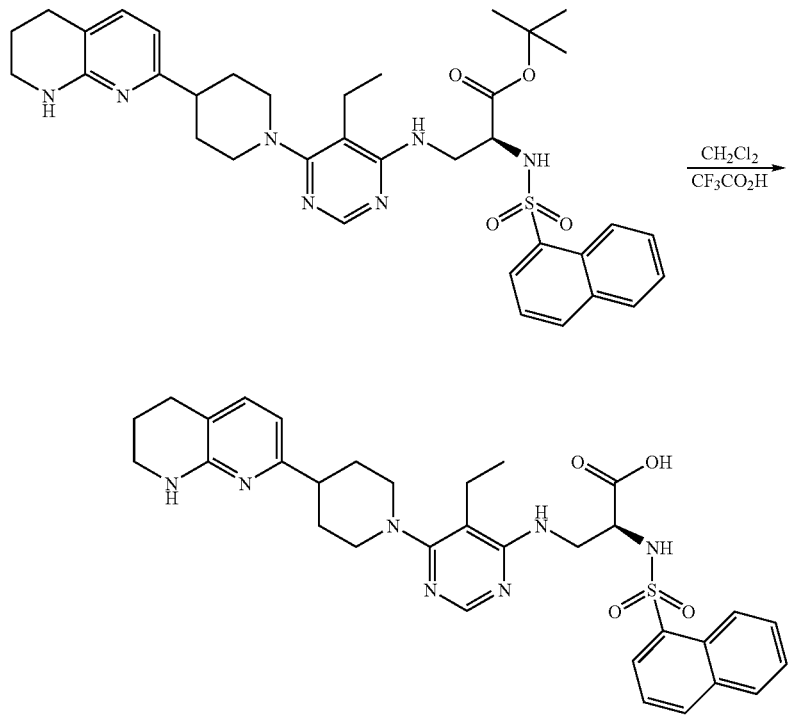

220 mg (0.33 mmoles) of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-(1-naphthalenesulphonyl) alaninate in 20 ml of dichloromethane with 2 ml of trifluoroacetic acid is stirred at ambient temperature until the starting product disappears according to TLC (silicagel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 230 mg (Yield=82% expressed as ditrifluoroacetate) of expected product is obtained in the form of a white solid.

TLC: Rf=0.10 (silicagel, eluent: dichloromethane-methanol-water-acetic acid 90-10-1-1)

IR (CHCl$_3$): 3412-3257(OH, NH); 1668(C=O); 1628, 1582, 1505 cm-1 (C=C, C=N, aromatic)

1H-NMR (DMSO-d6): δ 0.87 (t, 3H, CH$_2$—CH$_3$); 1.77 (m, 6H, CH$_2$—CH—CH$_2$, CH$_2$—CH$_2$—CH$_2$—NH); 2.05 (q, 1H, CH$_2$CH$_3$); 2.16 (q, 1H, CH$_2$—CH$_3$); 2.62 (t, 2H, CH$_2$—CH$_2$—CH$_2$—NH); 2.73 and 3.50 (2m, 4H, CH$_2$—CH$_2$—N—CH$_2$—CH$_2$); 2.80 (m, 1H, CH$_2$—CH—CH$_2$);

(m, 1H, H5 1-SO2naphthyl); 8.08 (d, 1H, H2 1-SO2naphthyl); 8.14 (d, 1H, H4 1-SO2naphthyl); 8.58 (m, 1H, H8 1-SO2naphthyl).

MS: 616 (MH+); 426 (MH-SOOnaphth+); 1231 (2MH+); 308.8 (M2H++); 614— (M-H-)

[α$_D$]: (0.4% CH3OH):+7.0

Example 33

Synthesis of (1,1-dimethylethyl)3-[[5-ethyl-6-[4-(1,2,3,4-tetrahydro-1,8-naphthyridin-7-yl)-1-piperidinyl]-4-pyrimidinyl]amino]-N-(2-pyridinyl)alaninate

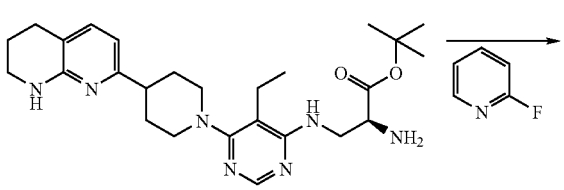

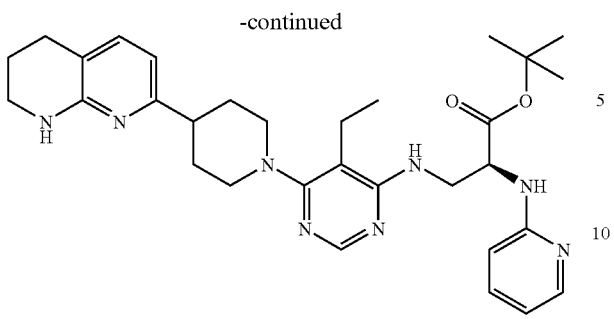

A mixture of 240 mg (0.50 mmole) of (1,1-dimethylethyl) 3-[5-ethyl-6-[4-(1,2,3,4-tetrahydro-1,8-naphthyridin-7-yl)-1-piperidinyl]-4-pyrimidinyl]amino]alaninate and 3 ml of 2-fluoropyridine is stirred for 24 hours under reflux. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on alumina eluting with a mixture of ethyl acetate-methylene chloride-methanol 80-16-4. 13 mg (Yield=05%) of expected product is obtained in the form of an oil.

TLC: Rf=0.40 (silicagel, eluent: methylene chloride-methanol 90-10).

MS: 559 (MH+).

Synthesis of 3-[[5-ethyl-6-[4-(1,2,3,4-tetrahydro-1,8-naphthyridin-7-yl)-1-piperidinyl]-4-pyrimidinyl]amino]-N-(2-pyridinyl)alanine

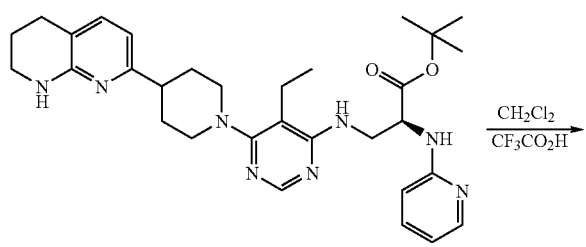

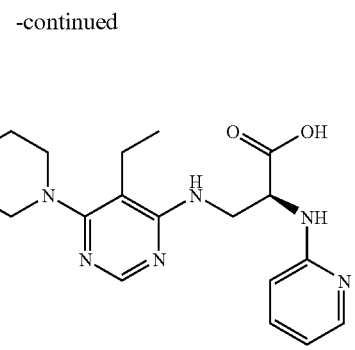

13 mg (0.023 mmole) of (1,1-dimethylethyl)3-[[5-ethyl-6-[4-(1,2,3,4-tetrahydro-1,8-naphthyridin-7-yl)-1-piperidinyl]-4-pyrimidinyl]amino]-N-(2-pyridinyl)alaninate in 2 ml of dichloromethane with 0.2 ml of trifluoroacetic acid is stirred at ambient temperature until the starting product disappears according to TLC (silicagel, eluent: CH2Cl2-MeOH-H2O—AcOH 90-10-1-1). Toluene is added and the reaction mixture is evaporated to dryness under reduced pressure (2 kPa). The residue is solubilized in the minimum amount of dichloromethane then poured into diisopropyl ether. The precipitate is filtered. 13 mg (Yield=76% expressed as ditrifluoroacetate) of expected product is obtained in the form of a beige solid.

TLC: Rf=0.35 (silicagel, eluent: dichloromethane-methanol-water-acetic acid 85-15-2-2)

MS: 503 (MH+); 501- (M-H-)

Example 34

Synthesis of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-(2-benzothiazolyl)alaninate

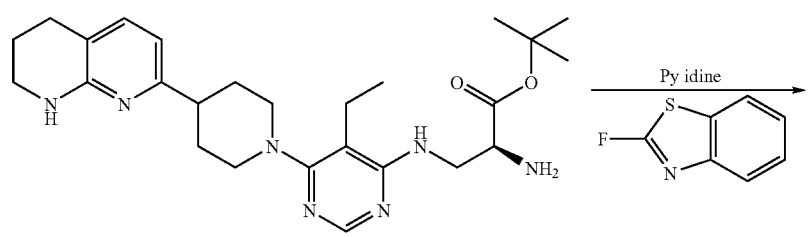

-continued

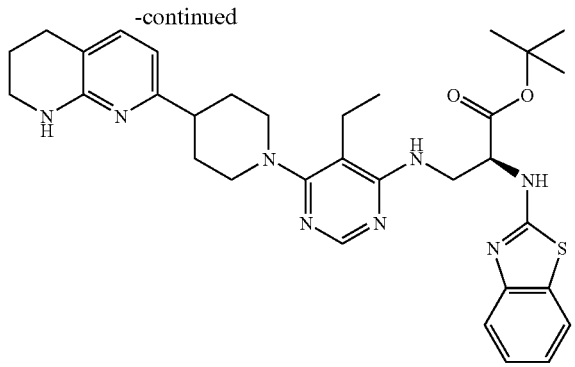

A mixture of 200 mg (0.42 mmole) of (1,1-dimethylethyl) 3-[5-ethyl-6-[4-(1,2,3,4-tetrahydro-1,8-naphthyridin-7-yl)-1-piperidinyl]-4-pyrimidinyl]amino]alaninate and 90 mg (0.6 mmole) of 2-fluorobenzothiazol in 5 ml of pyridine is stirred for 2 hours at 100° C. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed a first time on silicagel eluting with a gradient of methylene chloride-ethyl acetate-methanol 100-0-0 to 0-100-0 then 0-95-5; then a second time on reversed-phase RP8 eluting with a gradient of methanol-water 80-20 to 100-0. 50 mg (Yield=19%) of expected product is obtained in the form of a pink solid.

TLC: Rf=0.20 (silicagel, eluent: ethyl acetate-methanol 98-2).

1H-NMR (CDCl3): δ 1.06 (t, 3H, CH$_2$CH$_3$); 1.49 (s, 9H, tBu); 1.77 to 2.01(m, 6H, CH$_2$—CH—CH$_2$ and CH$_2$—CH$_2$CH$_2$—NH); 2.41 (q, 2H, CH$_2$—CH$_3$); 2.61 (t, 1H, CH$_2$—CH—CH$_2$); 2.72 (t, 2H, CH$_2$—CH$_2$—CH$_2$—NH); 2.92 and 3.51 (bq and bt, 4H, CH$_2$—CH$_2$—N—CH$_2$—CH$_2$); 3.42 (m, 2H, CH$_2$—CH$_2$—CH$_2$—NH); 3.95 and 4.09 (2m, 2H, NH—CH$_2$—CH—NH); 4.88 (m, 1H, NH—CH$_2$—CH—NH); 4.98 and 5.63 (m and t, 2H, NH—CH$_2$—CH—NH and NH—CH$_2$—CH—NH); 6.67 (bs, 1H, CH$_2$—CH$_2$—CH$_2$—NH); 6.41 and 7.13(2d, 2H, H naphthyridine); 7.12, 7.31 and 7.57 (t masked, t and bt 4H, H benzothiazol); 8.32 ppm (s, 1H, N=CH—N).

MS: 615 (MH+); 559 (MH-tBu+); 613–(M-H-).

Synthesis of 3-[[5-ethyl-6-[4-(1,2,3,4-tetrahydro-1,8-naphthyridin-7-yl)-1-piperidinyl]-4-pyrimidinyl]amino]-N-(2-benzothiazolyl)alanine

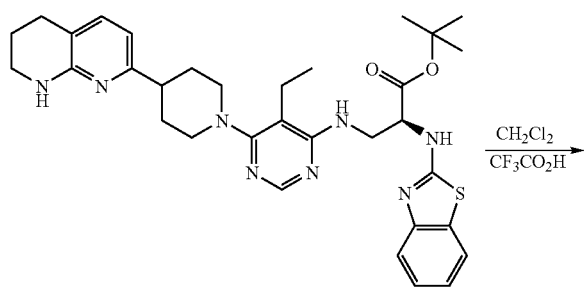

-continued

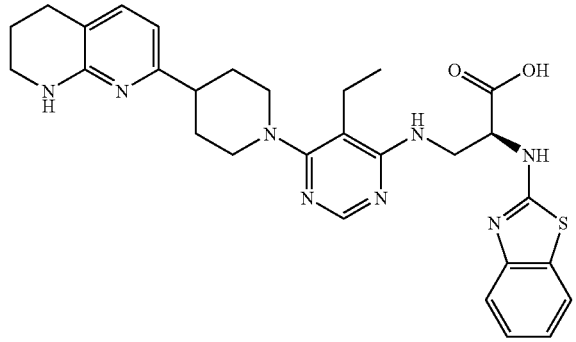

45 mg (0.073 mmole) of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-(2-benzothiazolyl)alaninate in 10 ml of dichloromethane with 1 ml of trifluoroacetic acid is stirred at ambient temperature until the starting product disappears according to TLC (silicagel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 60 mg (Yield=97% expressed as ditrifluoroacetate) of expected product is obtained in the form of a white solid.

TLC: Rf=0.45 (silicagel, eluent: dichloromethane-methanol-water-acetic acid 85-15-2-2)

1H-NMR (CDCl3): δ 1.15 (t, 3H, CH$_2$—CH$_3$); 1.75 to 2.07(m, 6H, CH$_2$—CH—CH$_2$CH$_2$—CH$_2$—CH$_2$—NH); 2.51 (q, 1H, CH$_2$—CH$_3$); 2.76 (bt, 2H, CH$_2$—CH$_2$—CH$_2$—NH); 2.96 (m, 1H, CH$_2$—CH—CH$_2$); 3.20 and 3.73 (2m, 4H, CH$_2$—CH$_2$—N—CH$_2$—CH$_2$); 3.51 (m, 2H, CH$_2$—CH$_2$—CH$_2$—NH); 4.23 (m, 2H, NH—CH$_2$—CH—NH); 4.67 (m, 1H, NH—CH$_2$—CH—NH); 6.38 and 7.35(2d, 2H, H naphthyridine); 7.20, 7.35, 7.47 and 7.54 (t, t masked, bd and bd 4H, H benzothiazol); 7.73 and 10.05 (2m, 2H, mobile Hs); 8.36 ppm (s, 1H, N=CH—N).

MS: 559 (MH+); 557–(M-H-)

Example 35

Operating by analogy with Example 34, starting from (1,1-dimethylethyl) 3-[5-ethyl-6-[4-(1,2,3,4-tetrahydro-1,8-naphthyridin-7-yl)-1-piperidinyl]-4-pyrimidinyl]amino] alaninate, 3-[[5-ethyl-6-[4-(1,2,3,4-tetrahydro-1,8-naphthyridin-7-yl)-1-piperidinyl]-4-pyrimidinyl]amino]-N-[2-(4-methoxybenzymidazolyl)]alanine is prepared in the form of a beige solid.

TLC: Rf=0.40 (silicagel, eluent: dichloromethane-methanol-water-acetic acid 85-15-2-2)

1H-NMR (CDCl3): δ 1.12 (m, 3H, CH$_2$C$\underline{H_3}$); 1.65 to 2.07 (m, 6H, C$\underline{H_2}$—CH—C$\underline{H_2}$ and CH$_2$—C$\underline{H_2}$—CH$_2$—NH); 2.47 (m, 2H, C$\underline{H_2}$—CH$_3$); 2.74 (m, 2H, C$\underline{H_2}$—CH$_2$—CH$_2$—NH); 2.92 (m, 1H, CH$_2$—C$\underline{H}$—CH$_2$); 3.17 and 3.73 (2m, 4H, CH$_2$—C$\underline{H_2}$—N—C$\underline{H_2}$—CH$_2$); 3.52 (m, 2H, CH$_2$—CH$_2$—C$\underline{_2}$—NH); 3.79 (s, 1H, OCH3); 4.18 (m, 2H, NH—C$\underline{H_2}$—C$\underline{H}$—NH); 4.81 (m, 1H, NH—CH$_2$—C$\underline{H}$—NH); 6.35 and 7.36c (2d, 2H, H naphthyridine); 6.72 and 7.18 (2d, 2H, NC(C)C$\underline{H}$C$\underline{H}$C(CH)OCH3); 6.87 (s, 1H,NC(C)C$\underline{H}$C(CH)OCH3); 6.37, 7.70 and 9.84 (mobile 3Hs); 8.32 ppm (s, 1H, N=C$\underline{H}$—N).

MS: 572 (MH+); 570–(M-H-)

Example 36

Synthesis of terbutyl 2-(2-benzyloxycarbonylamino-3-{5-methyl-6-[4-(5,6,7,8-tetrahydro-[1.8]naphthyridin-2-yl)-piperidin-1-yl]-pyrimidin-4-ylamino}-propinylamino)-propionate.

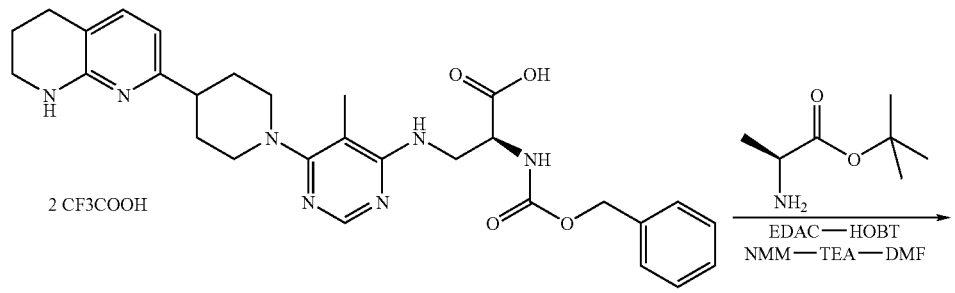

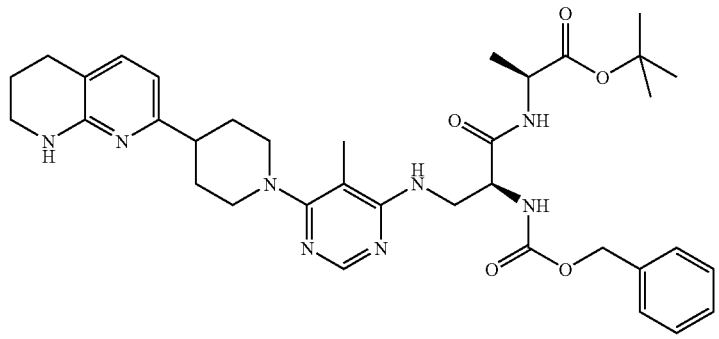

170 mg (0.30 mmole) of 3-[[5-methyl-6-[4-(1,2,3,4-tetrahydro-1,8-naphthyridin-7-yl)-1-piperidinyl]-4-pyrimidinyl]amino]-N-[(phenylmethoxy)carbonyl]alanine, 150 mg (1.0 mmole) of terbutyl L-alaninate, 66 mg (0.48 mmole) of 1-hydoxy benzotriazole, 90 mg (0.48 mmole) of 1-[3-(dimethylamino)propyl]-3-ethyl carbodiimide hydrochloride, 0.015 ml (0.135 mmole) of N-methhylmorpholine and 0.210 ml (1.50 mmoles) of triethylamine in 10 ml of dimethylformamide are stirred for 24 hours at ambient temperature. The reaction mixture is evaporated to dryness under reduced pressure (2 kPa) and the residue is taken up in ethyl acetate and a saturated solution of sodium bicarbonate. The organic phase is separated, dried over magnesium sulphate and the solvent is evaporated off under reduced pressure (2 kPa). The residue is chromatographed on silicagel eluting with a mixture of ethyl acetate-methylene chloride-methanol 50-50-10. 120 mg (Yield=60%) of expected product is obtained in the form of a white solid.

TLC: Rf=0.40 (silicagel, eluent: dichloromethane-methanol-water-acetic acid 90-10-1-1)

MS: 673 (MH+).

Synthesis of 2-(2-benzyloxycarbonylamino-3-{5-methyl-6-[4-(5,6,7,8-tetrahydro-[1.8]naphthyridin-2-yl)-piperidin-1-yl]-pyrimidin-4-ylamino}-propinylamino)-propionic acid.

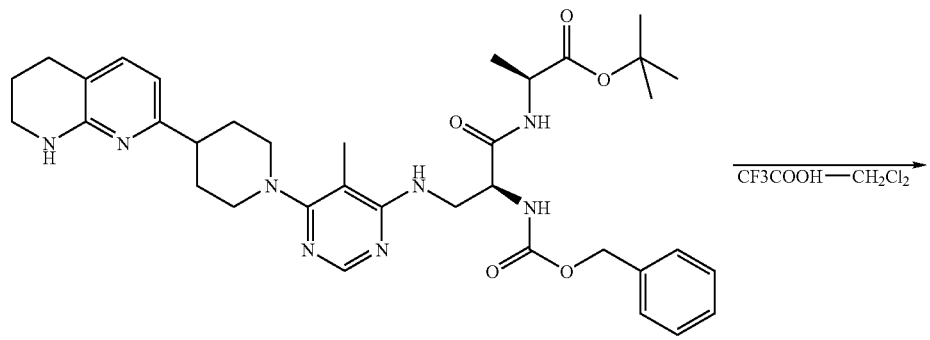

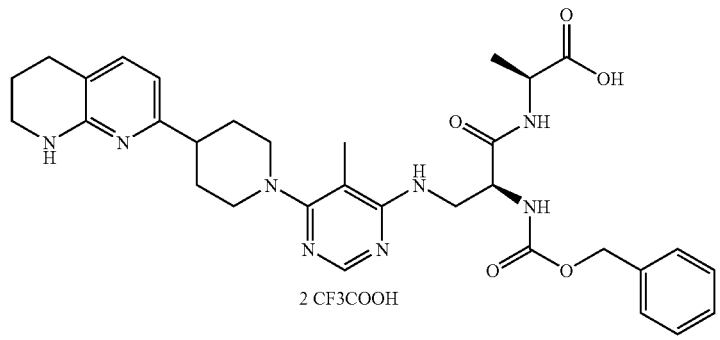

120 mg (0.179 mmoles) of terbutyl 2-(2-benzyloxycarbonylamino-3-{5-methyl-6-[4-(5,6,7,8-tetrahydro-[1.8] naphthyridin-2-yl)-piperidin-1-yl]-pyrimidin-4-ylamino}-propinylamino)-propionate in 5 ml of dichloromethane with 1 ml of trifluoroacetic acid is stirred at ambient temperature until the starting product disappears according to TLC (silicagel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 95 mg (Yield=63% expressed as ditrifluoroacetate) of expected product is obtained in the form of a white solid.

TLC: Rf=0.45 (silicagel, eluent: dichloromethane-methanol-water-acetic acid 85-15-2-2)

MS : 616 (MH+).

Example 37

Synthesis of terbutyl 2-(2-benzyloxycarbonylamino-3-{5-ethyl-6-[4-(5,6,7,8-tetrahydro-[1.8]naphthyridin-2-yl)-piperidin-1-yl]-pyrimidin-4-ylamino}-propinylamino)-propionate ml (0.45 mmole) of N-methhylmorpholine and 0.070 ml (0.50 mmole) of triethylamine in 5 ml of dimethylformamide are stirred for 24 hours at ambient temperature. The reaction mixture is evaporated to dryness under reduced pressure (2 kPa) and the residue is taken up in ethyl acetate and a saturated solution of sodium bicarbonate. The organic phase is separated, dried over magnesium sulphate and the solvent is evaporated off under reduced pressure (2 kPa). The residue is chromatographed on silicagel eluting with a gradient of ethyl acetate-methylene chloride-methanol from 50-50-0 to 50-45-5. 55 mg (Yield=53%) of expected product is obtained in the form of a white solid.

TLC: Rf=0.30 (silicagel, eluent: dichloromethane-methanol-water-acetic acid 90-10-1-1)

1H-NMR (CDCl3): δ 0.91 (t, 3H, CH2-CH3); 1.38 (d, 3H, CONH—CH(CH3)-CO); 1.48 (s, 9H, tBu); 1.79 to 2.07 (m, 6H, CH2—CH2—CH2—NH, CH2—CH—CH2); 2.49 (m, 2H, CH2—CH3); 2.66 (m, 1H, CH2—CH—CH2); 2.73 (t, 2H, CH2—CH2—CH2—NH); 2.97 and 3.63 (2m, 4H, CH2—C2—N—CH2—CH2); 3.42 (m, 2H, CH2—CH2—

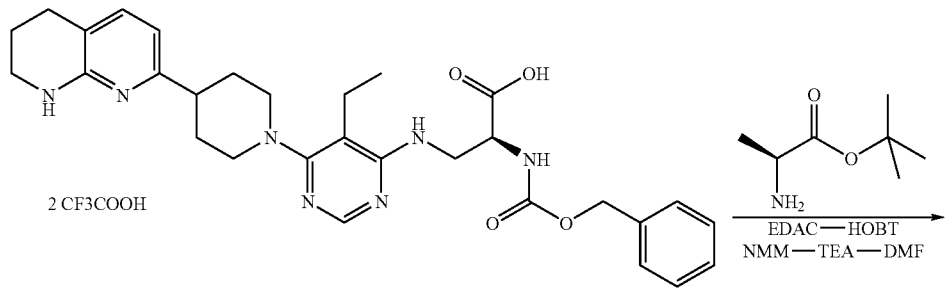

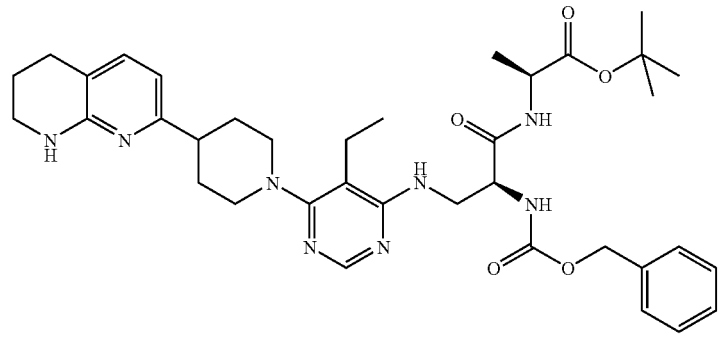

80 mg (0.15 mmole) of 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, 32 mg (0.20 mmole) of terbutyl L-alaninate, 22 mg (0.16 mmole) of 1-hydroxy benzotriazole, 30 mg (0.16 mmole) of 1-[3-(dimethylamino)propyl]-3-ethyl carbodiimide hydrochloride, 0.050

CH2—NH); 3.73 and 4.14 (2m, 2H, NH—CH2—CH—NH); 4.31 (m, 1H, NH—CH2—CH—NH); 4.44 (q, 1H, CONH—CH(CH3)-CO); 5.14 (m, 2H, CH2-Ph); 5.35, 6.92 and 7.89 (3H, mobile Hs); 6.42 and 7.14 (2d, 2H, H naphthyridine); 7.36 (m, 5H, Ph); 8.29 ppm (s, 1H, N=CH—N).

MS: 687 (MH+).

Synthesis of 2-(2-benzyloxycarbonylamino-3-{5-ethyl-6-[4-(5,6,7,8-tetrahydro-[1.8]naphthyridin-2-yl)-piperidin-1-yl]-pyrimidin-4-ylamino}-propinylamino)-propionic acid CONH—CH(CH3)-CO); 5.05 (m, 2H, CH$_2$-Ph); 6.41 and 7.38 (2d, 2H, H naphthyridine); 6.68, 7.20, 7.95 and 9.68 (4H, mobile Hs); 7.31 (m, 5H, Ph); 8.28 ppm (s, 1H, N=CH—N).
MS: 631 (MH+).

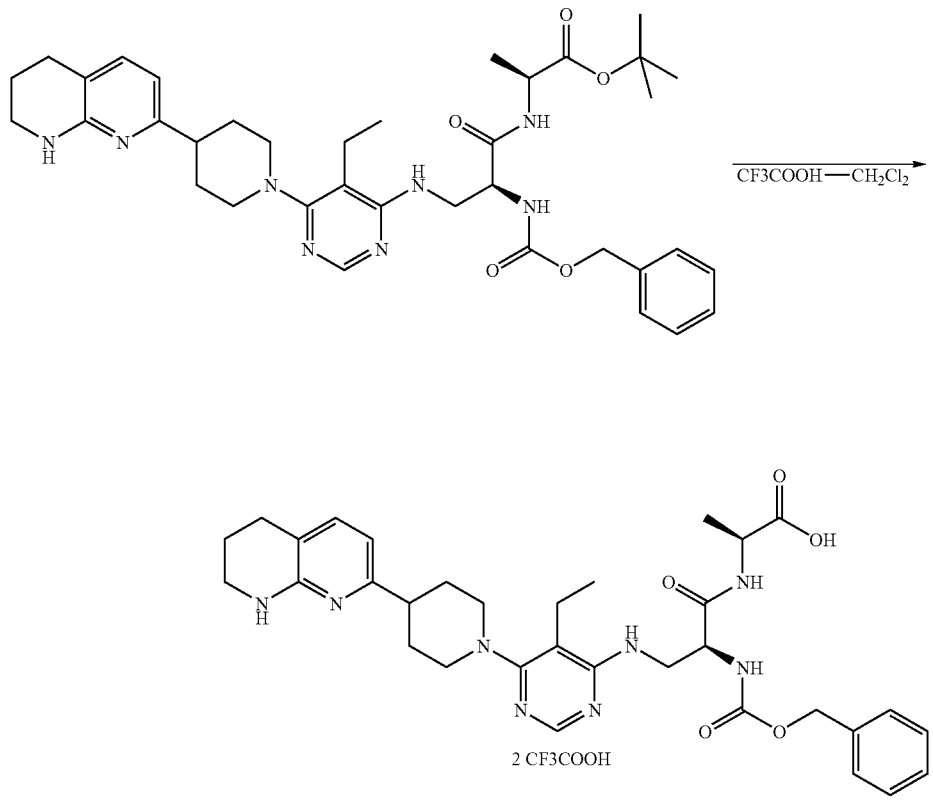

50 mg (0.073 mmoles) of terbutyl 2-(2-benzyloxycarbonylamino-3-{5-ethyl-6-[4-(5,6,7,8-tetrahydro-[1.8]naphthyridin-2-yl)-piperidin-1-yl]-pyrimidin-4-ylamino}-propinylamino)-propionate in 5 ml of dichloromethane with 0.5 ml of trifluoroacetic acid is stirred at ambient temperature until the starting product disappears according to TLC (silicagel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 53 mg (Yield=85% expressed as ditrifluoroacetate) of expected product is obtained in the form of a white solid.

TLC: Rf=0.12 (silicagel, eluent: dichloromethane-methanol-water-acetic acid 90-10-1-1)

1H-NMR (CDCl3): δ 1.16 (t, 3H, CH2-CH3); 1.41 (d, 3H, CONH—CH(CH3)-CO); 1.80 to 2.10 (m, 6H, CH$_2$—CH$_2$—CH$_2$—NH, CH$_2$—CH—CH$_2$); 2.48 (m, 2H, CH$_2$—CH$_3$); 2.79 (m, 2H, CH$_2$—CH$_2$—CH$_2$—NH); 3.00 (bt, 1H, CH$_2$—CH—CH$_2$); 3.28 and 3.84 (2m, 4H, CH$_2$—CH$_2$—N—CH$_2$—CH$_2$); 3.52 (m, 2H, CH$_2$—CH$_2$—CH$_2$—NH); 3.78 and 4.13 (2m, 2H, NH—CH$_2$—CH—NH); 4.46 (m, 1H, NH—CH$_2$—CH$_2$—NH); 4.59 (m, 1H, Example 38

1$^{st}$) Synthesis of tert-butyl 4-hydroxy-1-piperidinecarboxylate 1

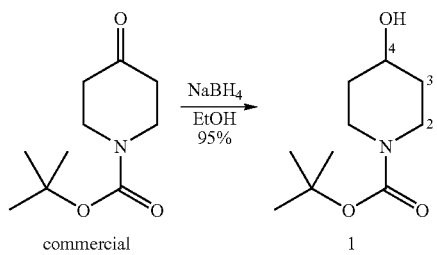

1 g (5 mmol) of tert-butyl 4-oxo-1-piperidinecarboxylate (marketed by Aldrich) is dissolved in 5 ml of ethanol. This solution is cooled down to 0° C. using an ice bath and 200 mg (7.56 mmol) of sodium tetraborohydride is added by portions and the reaction mixture is stirred for 4 hours at ambient temperature. A saturated aqueous solution of ammonium chloride is added. The ethanol is evaporated off under reduced pressure (2 kPa) then the reaction mixture is taken up in ethyl acetate. The organic phase is separated from the aqueous phase. This extraction is repeated one more time and then the organic phases are combined and dried over magnesium sulphate, followed by concentrating under reduced pressure (2 kPa) and in this way 1.05 g (Yield=100%) of a colourless oil is recovered.

TLC: Rf=0.5 (silicagel, eluent: CH2Cl2/MeOH 90:10

1H-NMR (CDCl3): δ 1.47 (s, 9H, tBu) and (m, 2H ; —CHH—CH2-N—CH2-CHH—); 1.87 (m, 2H, —CHH—CH2-N—CH2-CHH—); 3.04 (m, 2H, —CHH—N—CHH—); 3.85 (m, 2H, —CHH—N—CHH—) and (m, 1H, —CH—OH)

$2^{nd}$) Synthesis of tert-butyl 4-iodo-1-piperidinecarboxylate 2

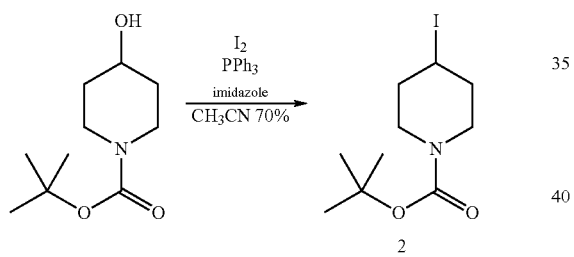

2.15 g of triphenylphosphine(8.2 mmole) and 2.08 g of iodine (8.2 mmole) are dissolved in 30 ml of acetonitrile.

The reaction mixture is stirred for 10 minutes at ambient temperature then 918 mg of imidazole (13.5 mmol) is added and stirring is maintained for another 10 minutes at ambient temperature. Then 1 g (5 mmol) of tert-butyl 4-hydroxy-1-piperidinecarboxylate of the preceding stage is added and stirring is maintained for 24 hours at ambient temperature. The reaction is treated by adding an aqueous solution of sodium thiosulphate and the acetonitrile is evaporated off under reduced pressure (2 kPa), followed by taking up in ethyl acetate, extracting and washing with an aqueous solution of sodium thiosulphate. The organic phases are dried over MgSO4, filtered and the ethyl acetate is evaporated off under reduced pressure (2 kPa). After chromatography on Silicagel eluting with dichloromethane then dichloromethane/methanol 90:10, 1.1 g (yield=70%) of a colourless oil is recovered.

TLC: Rf=0.8 (silicagel, eluent: CH2Cl2/MeOH 90:10

1H-NMR (CDCl3): δ 1.47 (s, 9H, tBu); 2.03 (m, 4H, —CH2-CHI-CH2-); 3.30 and 3.60 (2m, 4H, —CH2-N—CH2-); 4.46 (m, 1H—CHI—);

$3^{rd}$) Synthesis of 2-bromo-6(2,5-dimethyl-pyrol-1-yl)-pyridine 3

1 g (5.78 mmol) of 2-amino-6-bromopyridine marketed by Aldrich in 30 ml of toluene is placed in a 100 ml flask surmounted by a Dean Stark apparatus. 0.3 ml of acetic acid and 0.8 ml (6.78 mmol) of acetonylacetone marketed by Aldrich are added. The reaction medium is heated under reflux of the toluene for 5 hours, then left to return to ambient temperature and the toluene is evaporated off under reduced pressure (2 kPa). Water is added and extraction is carried out with ethyl acetate. The organic phases are combined and dried over magnesium sulphate. The ethyl acetate is evaporated off under reduced pressure(2 kPa) and the crude residue is purified by chromatography on silica gel eluting with dichloromethane.

1 g (Yield=90%) of a yellow powder is recovered.

TLC: Rf=0.7 (silicagel, eluent: CH2Cl2)

1H-NMR (CDCl3): δ 2.20 (s, 6H, —CH3C=CH—CH=CCH3-); 5.90 (s, 2H, —CH3C=CH—CH=CCH3-); 7.08 (d, 1H, H3 or H5 ); 7.16 (d, 1H, H3 or H5); 7.29(t, 1H, H4)

4<sup>th</sup>) Synthesis of 6-(2,5-Dimethyl-pyrrol-1-yl)-3',4',5',6'-tetrahydro-2'H-[2,4']bipyridinyl-1'-carboxylic acid tert-butyl ester 4

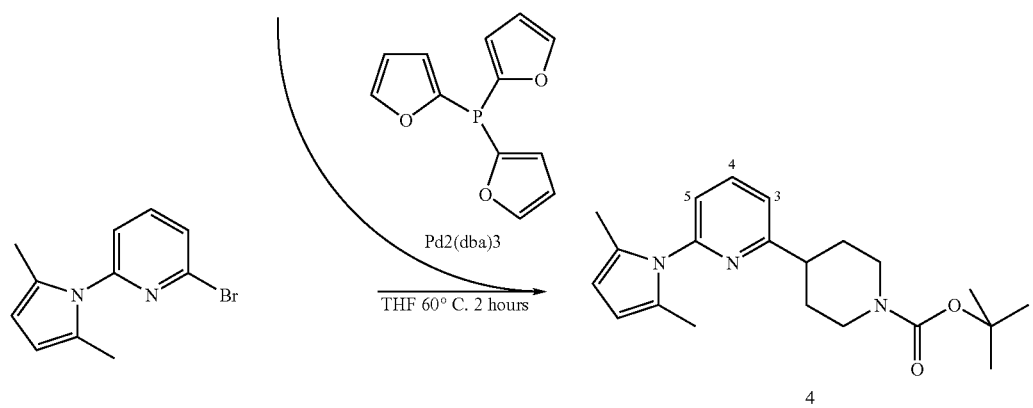

284 mg (4.34 mmol) of electrolytic zinc is put into suspension under an argon atmosphere, to which 0.033 ml of 1-2 dibromoethane and 1 ml of tetrahydrofuran are added.

After stirring for 3 minutes at 60° C. the reaction medium is left to return to ambient temperature. 0.047 ml of trimethylsilyl chloride is added and stirring is carried out for 30 minutes at ambient temperature. 1 g (3.2mmol) of 2 solubilized beforehand in 2 ml of tetrahydrofuran is added. This reaction mixture is stirred for 45 minutes at ambient temperature and it is added to a solution containing 30 mg (0.032 mmol) of tris(dibenzylideneacetone) dipalladium marketed by Aldrich and 30 mg (0.13 mmol) of tris(2-furyl)phosphine marketed by LANCASTER. Then 1 g (4 mmol) of 3 solubilized beforehand in 10 ml of tetrahydrofuran is added. The reaction mixture is left under magnetic stirring at 60° C. for 2 hours, then left to return to ambient temperature, filtered on clarcel and extracted between ethyl acetate and a saturated aqueous solution of sodium bicarbonate. After extracting the aqueous phase twice with ethyl acetate, the organic phases are combined and dried over magnesium sulphate. The ethyl acetate is evaporated off under reduced pressure (2 kPa) and the crude residue is purified by chromatography on silicagel eluting with a heptane/ethyl acetate mixture 4:1. 350 mg (yield=30%) of expected product is recovered in the form of a yellow oil.

TLC: Rf=0.2 (silicagel, eluent:Heptane/Ethyl acetate 90:10)

1H-NMR (CDCl3): δ 1.50 (s, 9H, tBu); 1.78 and 1.97 (m, 4H, —CH2-CH2-N—CH2-CH2-); 2.18 (s, 6H, —CH3C=CH—CH=CCH3-); 2.85 and 2.95 (m, 3H, CH—CH2-CHH—N—CHH—CH2-); 4.28 (m, 2H, —CH2-CHH—N—CHH—CH2-); 5.92 (s, 2H, —CH3C=CH—CH=CCH3-); 7.08 (d, 1H, H3 or H5); 7.16 (d, 1H, H3 or H5 ); 7.29(t, 1H, H4)

5<sup>th</sup>) Synthesis of 6-(2,5-dimethyl-pyrrol-1-yl)-1', 2', 3', 4', 5', 6'-hexahydro-[2,4']bipyridinyl

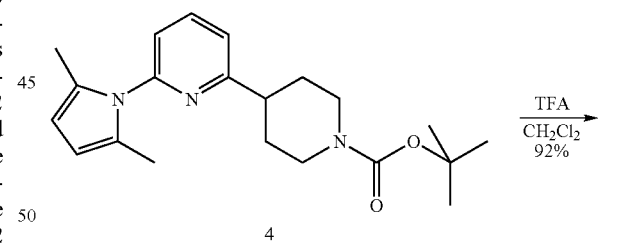

330 mg (0.928 mmol) of 4 is solubilized in 3 ml of dichloromethane to which 0.3 ml of trifluoroacetic acid is added.

The reaction medium is stirred for 2 hours at ambient temperature. The dichloromethane is evaporated off under reduced pressure (2 kPa). The residue obtained is taken up in water, the reaction medium is basified to pH=10 with concentrated ammonium hydroxide and the product is extracted with dichloromethane. The organic phase is dried over magnesium sulphate and the dichloromethane is evaporated off under reduced pressure (2 kPa). 220 mg (Yield=92%) of a yellow oil is recovered.

TLC: Rf=0.3 (silicagel, eluent: CH2Cl2/MeOH 90:10)

1H-NMR (CDCl3): δ 1.90 and 2.08 (m, 4H, —CH2-CH2-N—CH2-CH2-); 2.18 (s, 6H, —CH3C=CH—CH=CCH3-); 2.88 and 3.34 (m, 4H, —CH2-CH2-N—CH2-CH2-); 2.95,(m, 1H, CH—CH2-CH2-N—CH2-); 4.10 (m, 1H, NH); 5.92 (s, 2H, —CH3C=CH—CH=CCH3-);7.08 (d, 1H, H3 or H5); 7.16 (d, 1H, H3 or H5); 7.29(t, 1H, H4)

MS: 256 (MH+)

6<sup>th</sup>) Synthesis of 1'-(6-chloro-5-methyl-pyrimidin-4-yl)-6-(2,5-dimethyl-pyrrol-1-yl)-1', 2', 3', 4', 5', 6'-hexahydro-[2,4']bipyridinyl

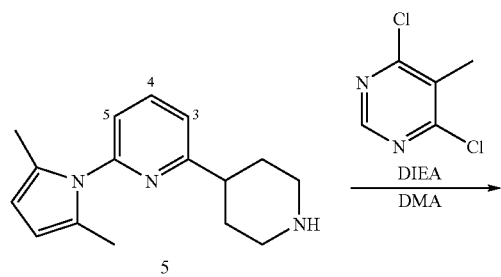

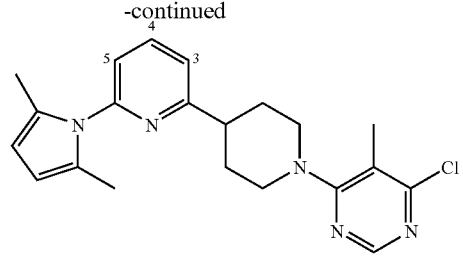

220 mg (0.860 mmol) of 5 is dissolved in 2 ml of dimethylacetamide to which 140 mg (0.860 mmol) of 4,6-dichloro-5-methyl-pyrimidine marketed by SPECS and 0.2 ml of diisopropylethylamine are added. The mixture is heated at 110° C. under magnetic stirring for one hour. The mixture is left to return to ambient temperature and the dimethylacetamide is evaporated off under reduced pressure (0.2 kPa). The crude residue is taken up in ethyl acetate and washed with water. The aqueous phase is extracted twice with ethyl acetate, the organic phases are combined and dried over magnesium sulphate. The ethyl acetate is evaporated off under reduced pressure (0.2 kPa) and 330 mg of a brown resin is recovered which is used for the following stage without purification.

TLC: Rf=0.4 (silicagel, eluent: CH2Cl2)

1H-NMR (CDCl3): δ 2.02 and 2.10 (m, 4H, —CH2-CH2-N—CH2-CH2-); 2.18 (s, 6H, —CH3C=CH—CH=CCH3-); 2.30(s, 3H, CH3); 3.08 and 4.01 (m, 4H, —CH2-CH2-N—CH2-CH2-); 3.02,(m, 1H, CH—CH2-CH2-N—CH2-); 5.92 (s, 2H, —CH3C=CH—CH=CCH3-);7.09 (d, 1H, H3 or H5 ); 7.20 ( d, 1H, H3 or H5); 7.29(t, 1H, H4); 8.41 (s, 1H, =N—CH=N)

7<sup>th</sup>) Synthesis of 2-benzyloxycarbonylamino-3-{6-[6-(2,5-dimethyl-pyrrol-1-yl)-3',4',5',6'-tetrahydro-2'H-[2,4']bipyridinyl-1'-yl]-5-methyl-pyrimidin-4-ylamino}-propionic acid tert-butyl ester 7

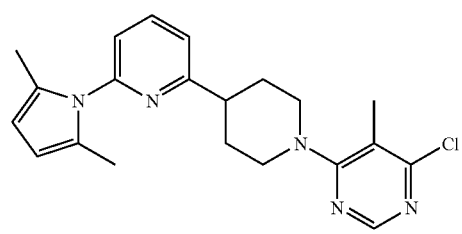

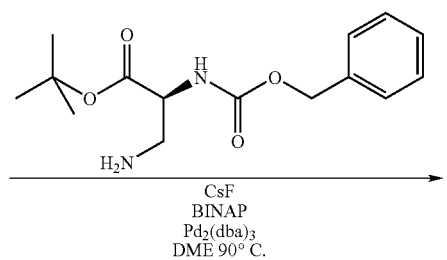

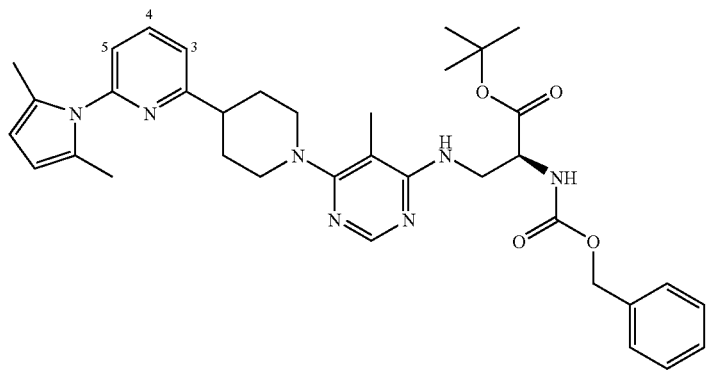

7

330 mg (0.866 mmol) of the preceding stage is solubilized in 5 ml of dimethoxyethane. 286 mg (1 mmol) of (1,1-dimethylethyl)3-amino-N-[(phenylmethoxy)carbonyl] alaninate (p)repared according to J. Med. Chem. (2001), 44(8), 1158-1176), 184 mg (1.21 mmol) of caesium fluoride, 54 mg (10% mol) of rac-2,2'-bis(diphenylphosphino)-1,1'-Binaphthyl marketed by Aldrich, and 40 mg (5% mol) of tris(dibenzylideneacetone) dipalladium marketed by Aldrich are added successively. This mixture is heated at 100° C. for 18 hours under magnetic stirring. Another 54 mg (10% mol) of rac-2,2'-Bis(diphenylphosphino)-1,1'-binapbthyl, 40 mg (5% mol) of tris(dibenzylideneacetone)dipalladium are added and heating is carried out for another 2 hours at 100° C. The reaction medium is left to return to ambient temperature and the dimethoxyethane is evaporated off under reduced pressure (2 kPa). The residue obtained is taken up in ethyl acetate and washed with a saturated aqueous solution of sodium bicarbonate. The aqueous phase is extracted with ethyl acetate, the organic phases are combined and dried over magnesium sulphate. The ethyl acetate is evaporated off under reduced pressure (2 kPa). The residue obtained is purified by chromatography on silicagel eluting with a heptane/ethyl acetate mixture 1:1. 200 mg of a yellow solid is recovered.

TLC: Rf=0.2 (silicagel, eluent: heptane/ethyl acetate 1:1)

1H-NMR (CDCl3): δ 1.50 (s, 9H, tBu); 1.97(s, 3H, CH3); 2.02 to 2.10(m, 4H, —C<u>H</u>2-CH2-N—CH2-C<u>H</u>2-); 2.18(s, 6H, —C<u>H</u>3C=CH—CH=CC<u>H</u>3-); 3.20 and 3.78(m, 4H, —CH2-C<u>H</u>2-N—C<u>H</u>2-CH2-); 3.00(m, 1H, C<u>H</u>—CH2-CH2-N—CH2-); of 3.85 to 4.00 (m,2H, NH—C<u>H</u>2-CHCOOtBuNH); 4.47(m, 1H, NH—CH2C<u>H</u>—COOtBuNH); 5.12(2H, —O—C<u>H</u>2-Phenyl); 5.92 (s, 2H, —CH3C=C<u>H</u>—C<u>H</u>=CCH3-); 6.12(m, mobile 1H); 7.09(d, 1H, H3 or H5); 7.21(d, 1H, H3 or H5); 7.78(t, 1H, H4); 7.45(m, aromatic 5H); 8.32(s, 1H, =N—CH=N)

MS: 641 (MH+), 584 (MH-tBu+)

8<sup>th</sup>) Synthesis of 3-[6-(6-Amino-3',4',5',6'-tetrahydro-2'H-[2,4']bipyridinyl-1'-yl)-5-methyl-pyrimidin-4-ylamino]-2-benzyloxycarbonylamino-propionic acid tert-butyl ester 8

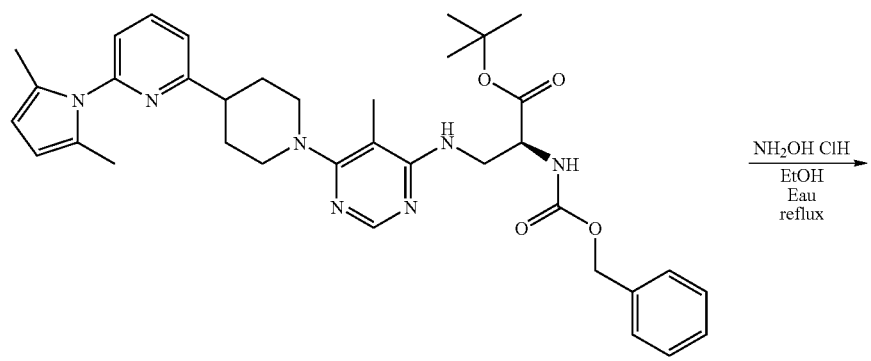

7

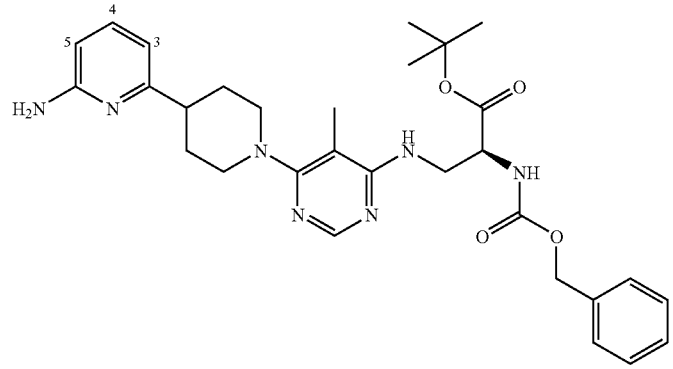

8

100 mg (0.15 mmol) of 7 is dissolved in 3 ml of ethanol and 0.3 ml of water. 50 mg (0.75 mmol) of hydroxylamine hydrochloride marketed by ACROS is added and the reaction medium is heated for 18 hours at 90° C. The solvents are evaporated off under reduced pressure (2 kPa) and the crude residue is purified by chromatography on silicagel eluting with a CH2Cl2/MeOH mixture 90:10. 30 mg (36%) of expected product is obtained in the form of a colourless resin.

TLC: Rf=0.5 (silicagel, eluent: CH2Cl2/MeOH 90:10)

1H-NMR (CDCl3): δ 1.50 (s, 9H, tBu); 1.97(s, 3H, CH3); 2.02 to 2.10(m, 4H, —CH2-CH2-N—CH2-CH2-; 2.18(s, 6H, —CH3C=CH—CH=CCH3-); 3.20 and 3.78(m, 4H, —CH2-CH2-N—CH2-CH2-); 3.00(m, 1H, CH—CH2-CH2-N—CH2-); of 3.85 to 4.00(m,2H, NH—CH2-CHCOOtBuNH); 4.47 (m, 1H, NH—CH2CH—COOtBuNH); 5.12(2H, —O—CH2-Phenyl); 5.92 (s, 2H, —CH3C=CH—CH=CCH3-); 6.18, 6.57, 6.62 (3d,H3 and H5+mobile 1H); 7.45 (m, aromatic 5H); 7.60 (t, 1H, H4); 8.32 (s, 1H, =N—CH=N).

MS: 562 (MH+),372(MH-tBu and —CO—O-benzyl+)

9$^{th}$) Synthesis of 3-[6-(6-Amino-3', 4', 5', 6'-tetrahydro-2'H-[2,4']bipyridinyl-1'-yl)-5-methyl-pyrimidin-4-ylamino]-2-benzyloxycarbonylamino-propionic acid 9

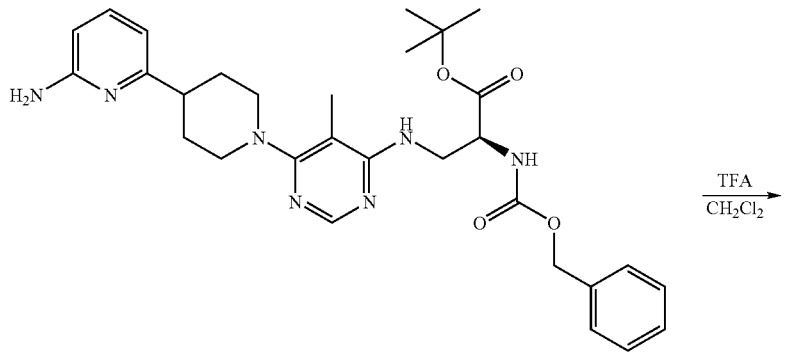

8

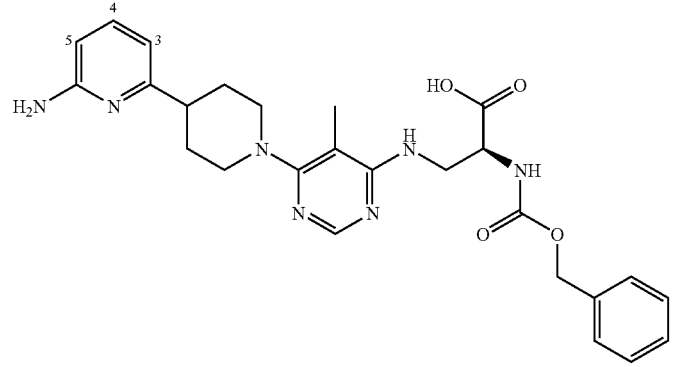

9

30 mg (0.053 mmol) of 8 prepared previously is solubilized in 2 ml of dichloromethane and 0.2 ml of trifluoroacetic acid. Stirring is maintained for 9 hours at ambient temperature. Toluene is added, followed by evaporating to dryness under reduced pressure(2 kPA). The product is purified by chromatography on silicagel eluting with a CH2Cl2/MeOH/acetic acid mixture 90:10:1.

10 mg (Yield=37%) of expected product is recovered solidified in the form of a beige solid in a CH2Cl2/isopropyl ether mixture.

TLC: Rf=0.2 (silicagel, eluent: CH2Cl2/MeOH/acetic acid 90:10:1

1H-NMR (DMSO): δ 1.90 (s, 3H, CH3); 1.80 to 1.85(m, 4H, —CH2-CH2-N—CH2-CH2-); partially masked by water of the DMSO:(4H, —CH2-CH2-N—CH2-CH2-) and (2H, NH—CH2-CHCOOtBuNH); 2.80,(m, 1H, CH—CH2-CH2-N—CH2-); 4.15(m, 1H, CH2-CH—COOtBuNH—); 5.02(2H, —O—CH2-Phenyl);6.27 (d, 1H, H3 or H5); 6.40 (d, 1H, H3 or H5 ); 6.52(m, 1H, H4); 7.5(m, aromatic 5H); 8.10(s, 1H, =N—CH=N).

MS: 506 (MH+), 372 (MH-CO—O-Benzyl+).

Example 39

3-[5-ethyl-6-[4-(aminomethyl-2-pyridinyl)-1-piperidinyl]-4-pyrimidinylamino]-N-[(phenylmethoxy)carbonyl]alanine, bis(trifluoroacetate)

Stage a

Synthesis of (1,1-dimethylethyl) acid(4-aminomethylpiperidine)-1-carboxylate

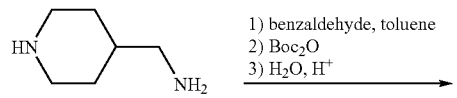

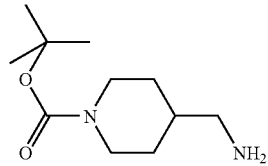

9 mL of benzaldehyde (87.5 mmoles) is added to a solution of 10 g (87.5mmoles) of 4-aminomethylpiperidine (marketed by Aldrich) in 110 ml of toluene placed under a nitrogen flow, then this mixture is heated at 120° C. (presence of a Dean-Stark apparatus) for 8 hours. The reaction mixture is left return to ambient temperature then 21 g (96.25 mmoles) of di-tert-butyl dicarbonate is added at 0° C. over ¼ of an hour. Stirring is maintained overnight in the presence of nitrogen. The next day, the reaction mixture is concentrated to dryness under reduced pressure (2 kPa) and the oil is taken up in 115 mL of a 1N aqueous solution of KHSO4 and stirred vigorously, under nitrogen for 7 hours. Ethyl acetate is added to the reaction mixture and the aqueous phase is extracted twice with ethyl acetate. Then the mother liquors are basified by the addition of NaOH pellets then the aqueous phase is extracted 3 times with chloroform salting out with NaCl. The combined organic phases are dried over magnesium sulphate then the solvent is evaporated off under reduced pressure (2 kPa). 17.3 g (Yield=92%) of expected product is obtained in the form of a yellow oil.

TLC: Rf=0.5 (alumina, eluent: dichloromethane-methanol (90-10)

1H-NMR (CDCl3): δ 1.05 and 1.67 (2m, 4H, N—CH2-CH2-CH—CH2-CH2); 1.17(s, 2H, NH2); 1.42 (s, 10H,tBu, CH2-CH—CH2); 2.55 (d, 2H, CH2-NH2); 2.65 and 4.07 (2m, 4H, N—CH2-CH2-CH—CH2-CH2).

MS: 215 (MH+); 159 (MH-tBu+).

Stage b

Synthesis of (1,1-dimethylethyl) acid(4-(2-aminomethylpyridinyl)-piperidine)-1-carboxylate

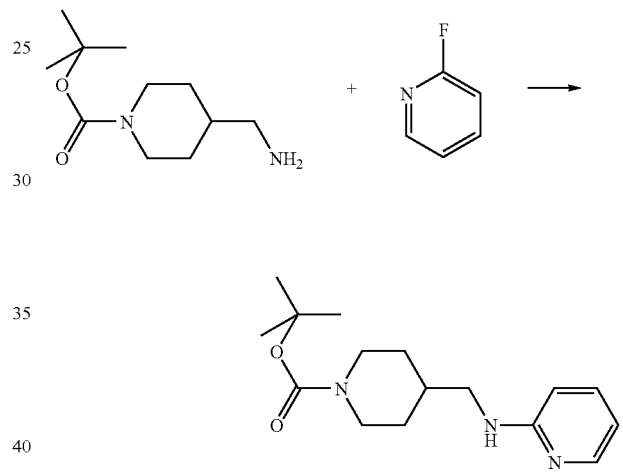

A mixture of 2.18 g (10.19 mmoles) of (1,1-dimethylethyl) acid(4-aminomethylpiperidine)-1-carboxylate in 5 ml of 2-fluoropyridine is taken to reflux for 6 hours. After returning to ambient temperature, the solvent is evaporated off under reduced pressure (2 kPa) and the yellow solid residue is taken up in a mixture of water, ethyl acetate and a saturated solution of sodium bicarbonate. The organic phase is decanted, washed with a saturated solution of sodium chloride then dried over magnesium sulphate and evaporated to dryness under reduced pressure (1.3 kPa). The residue is chromatographed on silicagel with the following eluent: ethyl acetate-cyclohexane 70-30. 1.19 g (Yield=40%) of expected product is obtained.

TLC: Rf=0.4 (silicagel, eluent: ethyl acetate-cyclohexane 70-30)

1H-NMR (CDCl3): δ 1.20 and 1.80 (2m, 5H, N—CH2-CH2-CH—CH2-CH2); 1.47 (s, 9H, tBu); 2.71 and 4.15 (2m, 4H, N—CH2-CH2-CH—CH2-CH2); 3.21 (m, 2H, CH—CH2-NH); 4.80 (m, 1H, CH—CH2-NH); 6.41 (d, 1H, CH=CH pyridine); 6.60 (m, 1H, CH=CH pyridine); 7.45 (m, 1H, CH=CH pyridine); 8.07 (m, 1H, N—CH=CH).

MS: 292 (MH+); 192 (MH-tBu+).

Stage c

Synthesis of 2-(4-methylpiperidinyl)aminopyridine

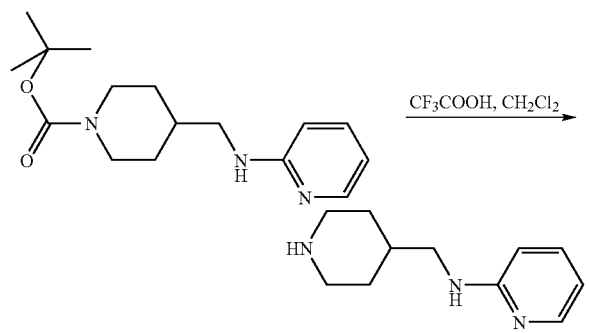

1.09 g (3.74 mmoles) of (1,1-dimethylethyl)acid(4-(2-aminomethylpyridinyl)-piperidine)-1-carboxylate in 25 ml of dichloromethane with 6 ml of trifluoroacetic acid is stirred at ambient temperature until the starting product disappears according to TLC (silicagel, eluent: ethyl acetate 100). Then 20 ml of toluene is added and the mixture is evaporated to dryness under reduced pressure (2 kPa). The residue is taken up in a mixture of methylene chloride and a 2N aqueous solution of sodium hydroxide. The organic phase is decanted, washed with a saturated solution of sodium chloride, dried over magnesium sulphate and evaporated to dryness under reduced pressure (2 kPa). The oil obtained is taken up in a little diisopropyl ether and pentane then condensed to dryness under reduced pressure (2 kPa). 590 mg (Yield=82%) of expected product is obtained in the form of a yellow solid.

TLC: Rf=0.2 (silicagel, eluent: dichloromethane-methanol-water-acetic acid 70-30-6-3).

1H-NMR (CDCl₃): δ 1.25 and 1.8 (2m, 4H, NH—CH2-CH2-CH—CH2-CH2); 1.72 (m, 1H, CH2-CH—CH2); 2.62 and 3.15 (2m, 6H, NH—CH2-CH2-CH—CH2-CH2 and CH—CH2-NH); 4.62 (s, 1H, mobile NH); 6.37 (d, 1H, CH=CH pyridine); 6.56 (m, 1H, CH=CH pyridine); 7.41 (m, 1H, CH=CH pyridine); 8.07 (m, 1H, N—CH=CH).

MS: 192 (MH+).

Stage d

Synthesis of 4-bromo-5-ethyl-6-[4-(aminomethyl-2-pyridinyl)-1-piperidinyl]-pyrimidine

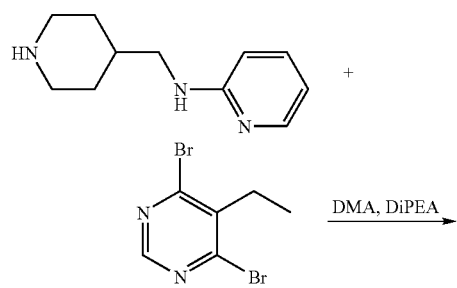

DMA, DiPEA

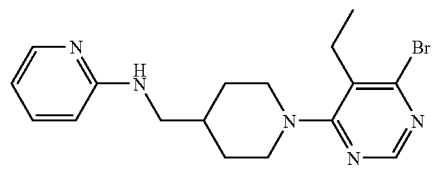

1.8 ml of diisopropylethylamine is added to a mixture of 657 mg (2.47 mmoles) of 4,6-dibromo-5-ethyl-pyrimidine and 450 mg (2.35 mmoles) of 2-(4-methylpiperidinyl)aminopyridine in 55 ml of N,N-dimethylacetamide. This mixture is heated at 110° C. for 4 hours. Then the solvent is eliminated under reduced pressure (0.2 kPa) and the residue is taken up in a mixture of ethyl acetate, water and a saturated solution of sodium bicarbonate. The organic phase is decanted, dried over magnesium sulphate then condensed under reduced pressure (2 kPa). The brown oil obtained is chromatographed on alumina eluting with the following gradient: heptane-ethyl acetate 80-20 to 70-30. 747 mg (Yield=84%) of expected product is obtained in the form of a beige solid.

TLC: Rf=0.5 (alumina, eluent: heptane-ethyl acetate 50-50).

1H—NMR (CDCl₃): δ 1.29 (t, 3H, CH2-CH3); 1.42 and 1.9 (2m, 5H, N—CH2-CH2-CH—CH2-CH2); 2.70 (q, 2H, CH2-CH3); 2.95 and 3.88 (2m, 4H, N—CH2-CH2-CH—CH2-CH2); 3.27 (m, 2H, CH—CH2-NH); 4.81 (m, 1H, mobile NH); 6.42 (m, 1H, CH=CH pyridine); 6.60 (m, 1H, CH=CH pyridine); 7.46 (m, 1H, CH=CH pyridine); 8.09 (m, 1H, N—CH=CH); 8.31 (s, 1H, N=CH—N).

MS: 378 (MH+).

Stage e

Synthesis of (1,1-dimethylethyl) 3-[5-ethyl-6-[4-(aminomethyl-2-pyridinyl)-1-piperidinyl]-4-pyrimidinylamino]-N-[(phenylmethoxy)carbonyl]alaninate

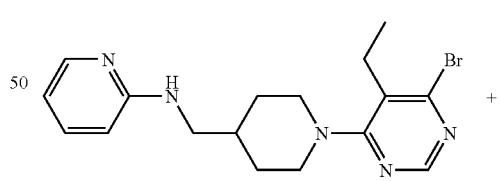

+

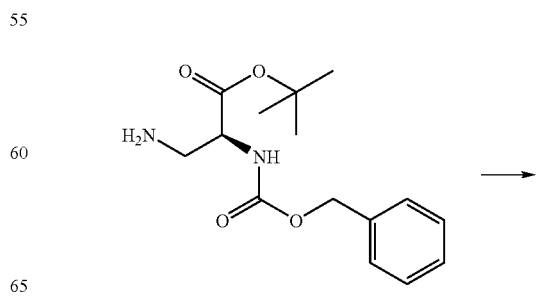

-continued

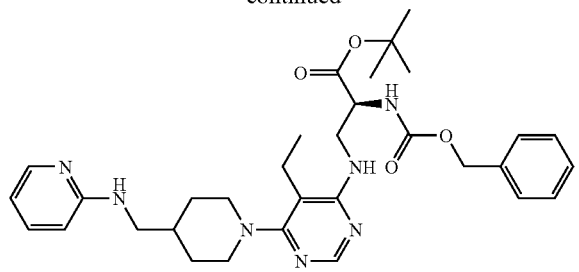

A mixture of 300 mg (0.79 mmoles) of 4-bromo-5-ethyl-6-[4-(aminomethyl-2-pyridinyl)-1-piperidinyl]-pyrimidine, 282.5 mg (0.96 mmoles) (1,1-dimethylethyl) 3-amino-N-[(phenylmethoxy) carbonyl]alaninate, 168.6 mg (1.11 mmoles) of caesium fluoride, 49.8 mg (0.08 mmoles) of tris(dibenzylideneacetone) dipalladium(0) and of 49.8 mg (0.08 mmoles) of rac-2,2'-Bis(diphenyl-phosphino)-1,1'-binaphthyl in 8 ml of 1,4-dioxane is taken to reflux for 7 hours. The reaction mixture is then returned to ambient temperature for the addition of 49.8 mg (0.08 mmoles) of tris(dibenzilideneacetone) dipalladium(0), then again taken to reflux for 4 hours. After cooling down, the mixture is concentrated under reduced pressure (2 kPa) then the residue obtained is taken up in a mixture of ethyl acetate, water and a saturated solution of sodium bicarbonate. The organic phase is decanted, dried over magnesium sulphate then concentrated under reduced pressure (2 kPa).

The residue is chromatographed a first time on alumina eluting with the following gradient: diisopropyl ether-ethyl acetate 80-20 to 100% ethyl acetate. The second chromatography is carried out on silicagel with ethyl acetate for eluent.

272 mg (Yield=58%) of expected product is obtained.

TLC: Rf=0.4 (silicagel, eluent: ethyl acetate).
1H-NMR (CDCl$_3$): δ 1.15 (t, 3H, CH2-<u>CH3</u>); 1.47 and 1.90 (2m, 13H, tBu, N—CH2-<u>CH2</u>-CH—<u>CH2</u>-CH2); 1.81 (m, 1H, N—CH2-CH2-<u>CH</u>—CH2-CH2); 2.41 (q, 2H, <u>CH2</u>-CH3); 2.85 and 3.50(2m, 4H, N—<u>CH2</u>-CH2-CH—CH2-<u>CH2</u>); 3.27 (m, 2H, CH—<u>CH2</u>-NH); 3.90 (m, 2H, NH—<u>CH2</u>-CH—NH); 4.45 (m, 1H, NH—CH2-<u>CH</u>—NH); 4.85 (m, 1H, mobile <u>NH</u>); 5.05 (m, 1H, mobile <u>NH</u>); 5.12 (s, 2H, O—<u>CH2</u>-Ph); 6.16 (bd, 1H, mobile <u>NH</u>); 6.42 (d, 1H, CH=CH pyridine); 6.60 (m, 1H, CH=CH pyridine); 7.35 (m, 5H, Ph); 7.45 (m, 1H, CH=CH pyridine); 8.07 (bd, 1H, N—<u>CH</u>=CH); 8.28 (s, 1H, N=<u>CH</u>—N).
MS: 590 (MH+); 534 (MH-tBu+).
[α]$_D$ (CHCl$_3$)=+2.9

Stage f

Synthesis of 3-[5-ethyl-6-[4-(aminomethyl-2-pyridinyl)-1-piperidinyl]-4-pyrimidinylamino]-N-[(phenylmethoxy)carbonyl]alanine, bis(trifluoroacetate)

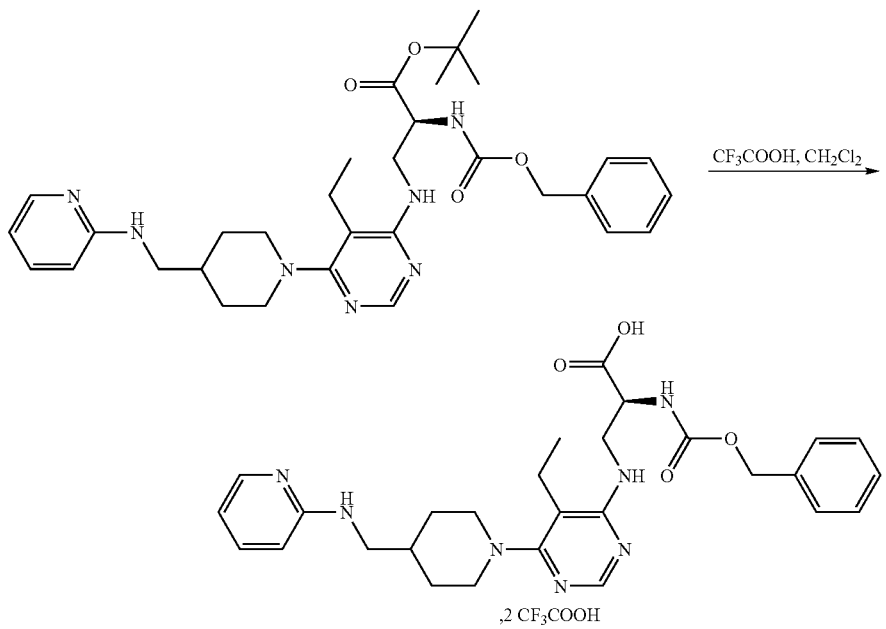

229 mg (0.39 mmoles) of (1,1-dimethylethyl) 3-[5-ethyl-6-[4-(aminomethyl-2-pyridinyl)-1-piperidinyl]-4-pyrimidinylamino]-N-[(phenylmethoxy)carbonyl]alaninate in 7.5 ml of dichloromethane with 0.9 ml of trifluoroacetic acid is stirred at ambient temperature until the starting product disappears according to TLC (silicagel, eluent: dichloromethane-methanol-water-acetic acid 90-10-1-1). At the end of the reaction, toluene is added to the reaction mixture followed by evaporating to dryness under reduced pressure (2 kPa). The residue is solubilized in the minimum amount of dichloromethane with a little methanol then poured into ethyl ether. The precipitate is filtered. 97.4 mg (Yield=38%) of expected product is obtained in the form of an amorphous solid.

TLC: Rf=0.1 (silicagel, eluent: dichloromethane-methanol-water-acetic acid 90-10-1-1).
1H-NMR (CDCl$_3$+2 drops MeOD): δ 1.12 (t, 3H, CH2-<u>CH3</u>); 1.43 and 1.95 (2m, 5H, N—CH2-<u>CH2</u>-<u>CH</u>—<u>CH2</u>-CH2); 2.41 (q, 2H, <u>CH2</u>-CH3); 3.10 and 3.65(2m, 4H, N—CH2-CH2-CH—CH2-CH2); 3.26 (d, 2H, CH—CH2-NH); 3.80 and 4.02 (2m, 2H, NH—CH2-CH—NH); 4.41 (m, 1H, NH—CH2-CH—NH); 5.10 (s, 2H, O—CH2-Ph); 6.74 (t, 1H, CH=CH pyridine); 6.87 (d, 1H, CH=CH pyridine); 7.32 (m, 5H, Ph); 7.81 (m, 2H, CH=CH pyridine and N—CH=CH); 8.23 (s, 1H, N=CH—N).

MS: 534 (MH+).

[α]$_D$ (CHCl$_3$)=+1.88

Example 40

Stage a

Synthesis of (1,1-dimethylethyl)acid4-[3-(4-methoxy-2-nitro-phenyl)-thioureidomethyl]-piperidine-1-carboxylate

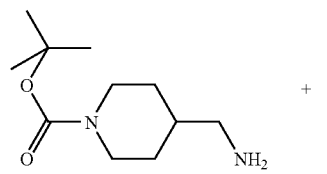

+

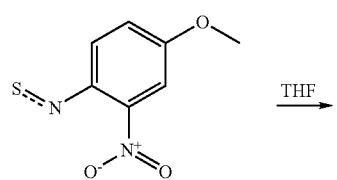

THF →

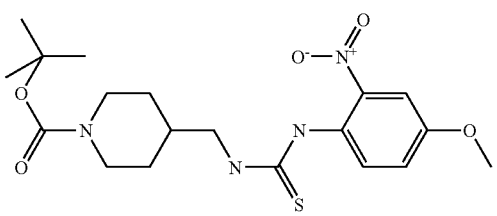

A mixture of 1 g (4.67 mmoles) of (1,1-dimethylethyl) acid 4-aminomethylpiperidine)-1-carboxylate and 1.08 g (6.06 mmoles) of 4-methoxy-2-nitrophenyl isothiocyanate in 70 ml of tetrahydrofuran is stirred at ambient temperature, under a nitrogen flow for 5 hours. Then, the solvent is evaporated off under reduced pressure (2 kPa) and the residue is chromatographed on silicagel with the following eluent: ethyl acetate-heptane from 20-80 to 30-70. 1.66 g (Yield=84%) of expected product is obtained.

TLC: Rf=0.4 (silicagel, eluent: ethyl acetate-heptane 50-50)

1H-NMR (CDCl$_3$): δ 1.25 and 1.76 (2m, 4H, N—CH2-CH2-CH—CH2-CH2); 1.47 (s, 9H, tBu); 1.91 (m, 1H, N—CH2-CH2-CH—CH2-CH2); 2.73 and 4.15 (2m, 4H, N—CH2-CH2-CH—CH2-CH2); 3.51 (m, 2H, CH—CH2-NH); 3.90 (s, 3H, O—CH3); 6.66 (m, 1H, CH=CH aromatic); 7.22 (m, 1H, CH=CH aromatic); 7.59 (m, 1H, CH=CH aromatic).

MS: 425(MH+); 325(MH-COOtBu+).

Stage b

Synthesis of (1,1-dimethylethyl)4-[(6-methoxy-2-aminomethylbenzimidazole)]-piperidine-1-carboxylate

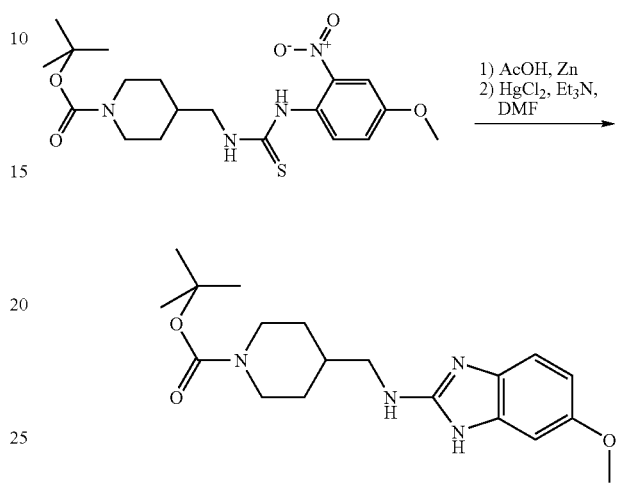

A mixture of 2 g of activated zinc in a little acetic acid (the zinc is activated by heating with heat gun) is added to a solution of 1.12 g (2.64 mmoles) of (1,1-dimethylethyl) acid4-[3-(4-methoxy-2-nitro-phenyl)-thioureidomethyl]-piperidine-1-carboxylate in 100 ml of acetic acid. The reaction mixture is left under stirring for 5 hours then the clarcel is added to the solution, followed by filtering on clarcel and the solvent is evaporated off under reduced pressure (2 kPa). 1.8 g of the expected product is obtained.

This crude product is then solubilized in 100 ml of dimethylformamide and 10 ml of triethylamine and 500 mg of mercury dichloride are added to it. The reaction mixture is placed under stirring at ambient temperature for 15 hours. Then the solvent is evaporated off under reduced pressure (0.2 kPa) and the residue is taken up in a mixture of water, a saturated solution of sodium bicarbonate and ethyl acetate. The organic phase is decanted, dried over magnesium sulphate and the solvent eliminated by evaporation under reduced pressure (2 kPa). The residue is chromatographed on alumina eluting with the following gradient: ethyl acetate-dichloromethane/methanol 50-50(100% CH2Cl2) to 50-50(95/5 CH2Cl2/MeOH). 740 mg (Yield=77% over 2 stages) of expected product is obtained.

TLC: Rf=0.4 (alumina, eluent: ethyl acetate-dichloromethane/methanol 50-50(95/5)).

1H-NMR (CDCL$_3$): δ 1.07 and 1.64 (2m, 4H, N—CH2-CH2-CH—CH2-CH2); 1.46 (s, 9H, tBu); 1.76 (m, 1H, N—CH2-CH2-CH—CH2-CH2); 2.61 and 4.05 (2m, 4H, NH—CH2-CH2-CH—CH2-CH2); 3.29 (m, 2H, CH—CH2-NH); 3.81 (s, 3H, O—CH3); 6.66 and 7.12 (2d, 2H, CH=CH benzimidazole); 6.88 (s, 1H, NH—C=CH—C—OCH3).

MS: 361 (MH+); 305 (MH-tBu+); 261 (MH-COOtBu+).

Stage c

Synthesis of 4-(6-methoxy-2-aminomethylbenzimidazole)piperidine, tri(trifluoroacetate)

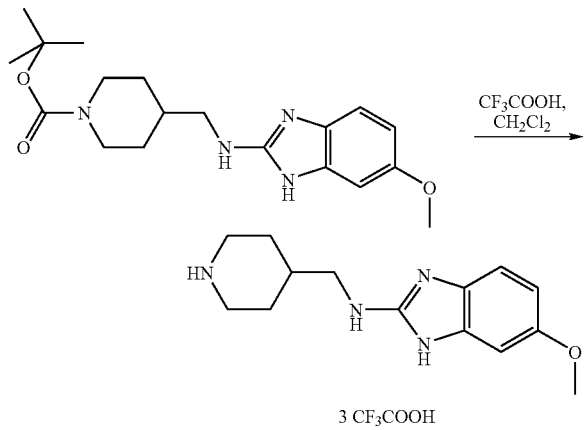

3 CF₃COOH 918 mg (2.55 mmoles) of (1,1-dimethylethyl)acid4-[(6-methoxy-2-aminomethylbenzimidazole)]-piperidine-1-carboxylate in 35 ml of dichloromethane with 6 ml of trifluoroacetic acid is stirred at ambient temperature until the starting product disappears according to TLC (silicagel, eluent: dichloromethane-methanol-water-acetic acid 90-10-1-1). Then toluene is added and the mixture evaporated under reduced pressure (2 kPa). 1.15 g of expected product is obtained in the form of the trifluoroacetate salt.

TLC: Rf=0.15 (silicagel, eluent: dichloromethane-methanol-water-acetic acid 90-10-1-1).

1H-NMR (MeOD): δ 1.50 and 2.05 (2m, 5H, NH—CH2-CH2-CH—CH2-CH2); 3.00 and 3.43 (2m, 4H, NH—CH2-CH2-CH—CH2-CH2); 3.35 (d, 2H, CH—CH2-NH); 3.81 (s, 3H, O—CH3); 6.85 and 7.25 (2m, 2H, CH=CH benzimidazole); 6.91 (s, 1H, NH—C=CH—C—OCH3).

MS: 261 (MH+).

Stage d

Synthesis of 4-bromo-5-ethyl-6-[4-(6-methoxy-2-aminomethylbenzimidazole)-1-piperidinyl]pyrimidine

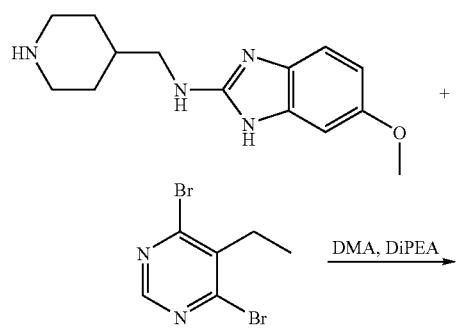

DMA, DiPEA

-continued

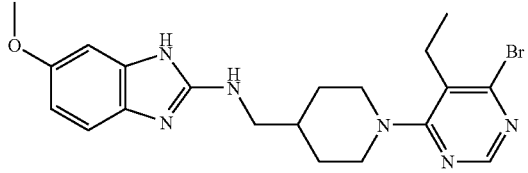

35 ml of N,N-dimethylacetamide, 381.84 mg (1.43 mmoles) of 4,6-dibromo-5-ethyl-pyrimidine in solution are added into a single-necked flask containing 356 mg (1.37 mmoles) of 4-(6-methoxy-2-aminomethylbenzimidazole)piperidine, freed from its salt, then 1.2 ml of diisopropylethylamine is added. This mixture is heated at 110° C. for 3 hours then concentrated under reduced pressure (0.2 kPa). The residue obtained is taken up in a mixture of water, ethyl acetate and a saturated solution of sodium bicarbonate. The organic phase is separated and the aqueous phase reextracted with ethyl acetate. The combined organic phases are dried over magnesium sulphate, filtered then the solvent is evaporated off under reduced pressure (2 kPa). The product obtained is chromatographed on silicagel eluting with a gradient of dichloromethane-methanol 95-5 then dichloromethane-methanol 90-10).

383 mg (Yield=63%) of expected product is obtained.

Preparation of 4-(6-methoxy-2-aminomethyl benzimidazole)piperidine in free amine form:

700 mg of 4-(6-methoxy-2-aminomethylbenzimidazole) piperidine is displaced from its salt by 6 mass equivalents of basic amberlyst A21 resin (resin of R—NMe₂ type) in a CH₂C₂-MeOH—AcOEt 1-1-1 mixture under stirring for 30 minutes. The resin is washed beforehand and left to swell for 20 minutes in this solvent mixture. This operation must be repeated 3 times for the displacement of the salt to be complete. After filtration of the resin and evaporation of the solvents, 356 mg (1.37 mmoles) of free 4-(6-methoxy-2-aminomethylbenzimidazole)piperidine is obtained.

TLC: Rf=0.23 (silicagel, eluent: dichloromethane-methanol 90-10).

1H-NMR (CDCL₃): δ 1.27 (t, 3H, CH2-CH3); 1.32 and 1.80 (2m, 4H, N—CH2-CH2-CH—CH2-CH2); 1.89 (m, 1H, N—CH2-CH2-CH—CH2-CH2); 2.63 (q, 2H, CH2-CH3); 2.85 and 3.82 (2m, 7H, N—CH2-CH2-CH—CH2-CH2, O—CH3); 3.37 (m, 2H, CH—CH2-NH); 6.67 and 7.15 (2d, 2H, CH=CH benzimidazole); 6.90 (s, 1H, NH—C=CH—C—OCH3); 8.27 (s, 1H, N=CH—N).

MS: 446 (MH+).

Stage e

Synthesis of (1,1-dimethylethyl)benzimidazole)-1-piperidinyl]pyrimidine 4-bromo-5-ethyl-6-[4-(6-methoxy-2-aminomethyl-1-carboxylate

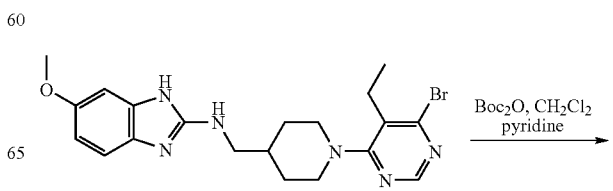

Boc₂O, CH₂Cl₂
pyridine

-continued

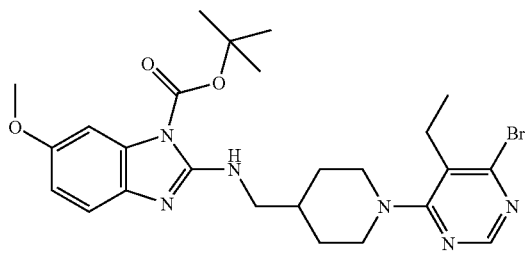

1.5 ml of pyridine then 471 mg (2.16 mmoles) of di-tert-butyldicarbonate are added to a mixture of 159.7 mg (0.36 mmoles) of 4-Bromo-5-ethyl-6-[4-(6-methoxy-2-aminomethylbenzimidazole)-1-piperidinyl]pyrimidine in 15 ml of dichloromethane. The reaction medium is left under stirring at ambient temperature overnight. A little toluene is added to the reaction mixture then the solvent is evaporated off under reduced pressure (2 kPa). The residue is taken up in a mixture of water, ethyl acetate and a saturated solution of sodium bicarbonate. The organic phase is decanted, dried over magnesium sulphate then condensed under reduced pressure (2 kPa). The crude product obtained is chromatographed on silicagel eluting with the following gradient: heptane-ethyl acetate 60-40 to 50-50. 136 mg (Yield=69%) of expected product is obtained (in the form of 2 regioisomers distinguished by NMR with a ratio of 50/50).

TLC: Rf=0.5 (silicagel, eluent: dichloromethane-methanol 90-10).

1H-NMR (CDCL$_3$): δ 1.30 (t, 6H, CH2-CH3); 1.47 and 1.96 (2m, 8H, N—CH2-CH2-CH—CH2-CH2); 1.72 (2s1, 20H, tBu, N—CH2-CH2-CH—CH2-CH2); 2.70 (q, 4H, CH2-CH3); 2.97 and 3.89(2m, 8H, N—CH2-CH2-CH—CH2-CH2); 3.52 (m, 4H, CH—CH2-NH); 3.82 (s, 6H, OCH3); 6.62 and 6.82 and 7.31 and 7.46 (4d, 4H, CH=CH benzimidazole); 7.00 and 7.26 (2s, 2H, NH—C=CH—C—OCH3); 8.31 (s, 2H, N=CH—N).

MS: 545/547 (MH+).

Stage f

Synthesis of (1,1-dimethylethyl)3-[5-ethyl-6-[4-(6-methoxy-2-aminomethylbenzimidazole-1-carboxylate(1,1-dimethylethyl))-1-piperidinyl]-4-pyrimidinylamino]-N-[(phenylmethoxy)carbonyl]alaninate

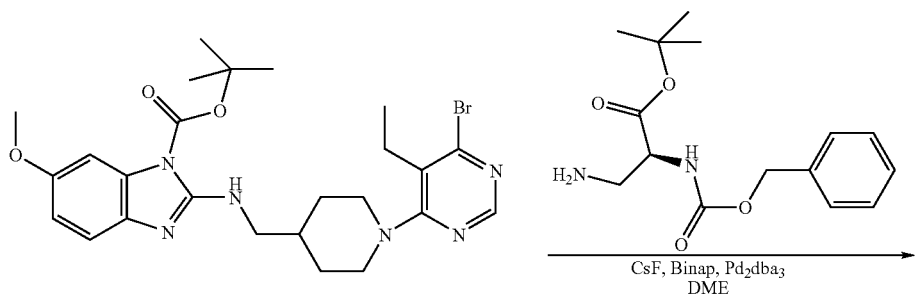

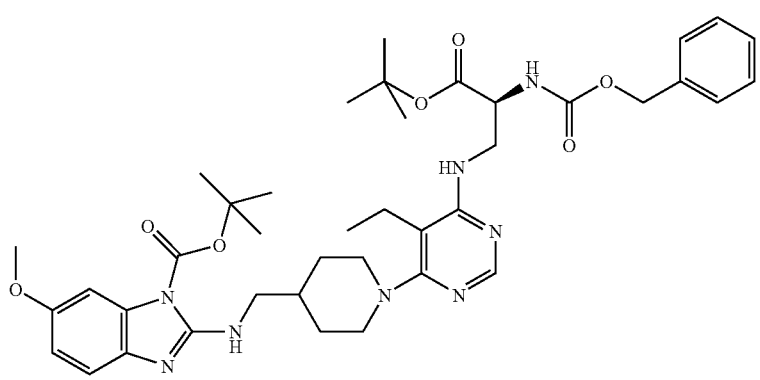

A mixture of 136 mg (0.25 mmoles) of (1,1-dimethylethyl) benzimidazole)-1-piperidinyl]pyrimidine4-bromo-5-ethyl-6-[4-(6-methoxy-2-aminomethyl-1-carboxylate, 88.5 mg (0.30 mmoles) of (1,1-dimethylethyl)3-amino-N-[(phenyl-methoxy)carbonyl]alaninate, 53.2 mg (0.35 mmoles) of caesium fluoride, 11.4 mg (0.012 mmoles) of tris(dibenzylideneacetone)dipalladium(0) and 15.6 mg (0.025 mmoles) of rac-2,2'-bis(diphenyl-phosphino)-1,1'-binaphthyl in 6 ml of 1,2-dimethoxyethane is taken to reflux for 24 hours. During the reaction, 11.4 mg of tris(dibenzilideneacetone)dipalladium(0) is added. After cooling down, the mixture is concentrated under reduced pressure (2 kPa) then the residue obtained is taken up in a mixture of ethyl acetate, water and a saturated solution of sodium bicarbonate. The organic phase is decanted, dried over magnesium sulphate then concentrated under reduced pressure (2 kPa). The residue is chromatographed a first time on silicagel eluting with the following gradient: ethyl acetate-heptane 40-60 to 100% ethyl acetate. The second chromatography is carried out on alumina eluting with the following gradient: ethyl acetate-dichloromethane-methanol 50-50-0 to 50-50-2%.

58 mg (Yield=30%) of expected product is obtained (in the form of 2 regioisomers distinguished by NMR with a ratio of 50/50).

TLC: Rf=0.4 (silicagel, eluent: ethyl acetate).

1H-NMR (CDCl$_3$): δ 1.15 (t, 6H, CH2-CH3); 1.46 and 1.91 (2m, 26H, tBu, N—CH2-CH2-CH—CH2-CH2); 1.72 (m, 20H, tBu, N—CH2-CH2-CH—CH2-CH2); 2.41 (q, 4H, CH2-CH3); 2.87 and 3.51(2m, 12H, N—CH2-CH2-CH—CH2-CH2, CH—CH2-NH); 3.82 (s, 6H, OCH3); 3.90 (m, 4H, NH—CH2-CH—NH); 4.43 (m, 2H, NH—CH2-CH—NH); 5.12 (s, 4H, O—CH2-Ph); 6.12 (bd, 2H, mobile NH); 6.61 (d, 1H, CH═CH benzimidazole); 6.82 (m, 1H, CH═CH benzimidazole); 7.00 (bs, 1H, NH—C═CH—C—OCH3); 7.35 (m, 12H, Ph, CH═CH benzimidazole); 7.45 (d, 1H, CH═CH benzimidazole); 8.29 (s, 2H, N═CH—N).

HPLC/MS: 759 (MH+); 659 (MH-COOtBu+); 603 (MH-COOtBu-tBu+).

Stage g

Synthesis of 3-[5-ethyl-6-[4-(6-methoxy-2-aminomethyl benzimidazole)-1-piperidinyl]-4-pyrimidinylamino]-N-[(phenylmethoxy)carbonyl]alanine, bis (trifluoroacetate)

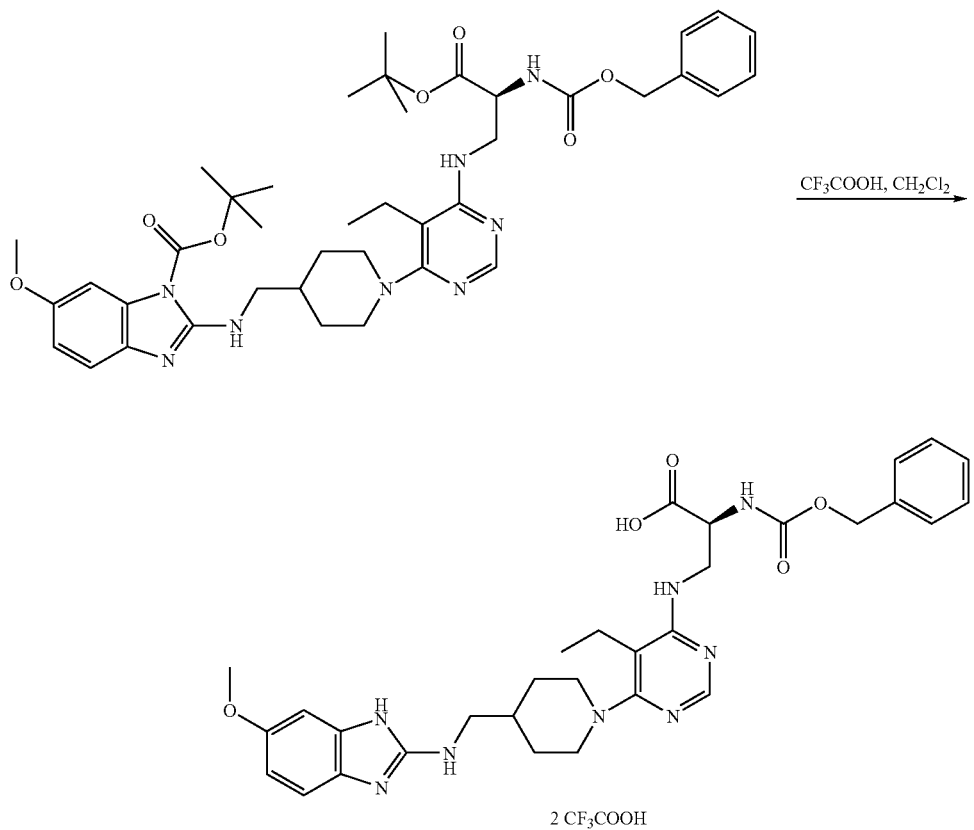

58 mg (0.08 mmoles) of 3-[5-ethyl-6-[4-(6-methoxy-2-aminomethylbenzimidazole-1-carboxylate of (1,1-dimethylethyl)(1,1-dimethylethyl))-1-piperidinyl]-4-pyrimidinylamino]-N-[(phenylmethoxy)carbonyl]alaninate in 2 ml of dichloromethane with 0.2 ml of trifluoroacetic acid is stirred at ambient temperature until the starting product disappears according to TLC (silicagel, eluent: dichloromethane-methanol-water-acetic acid 90-10-1-1). At the end of the reaction, toluene is added to the reaction mixture followed by evaporating to dryness under reduced pressure (2 kPa). The residue is solubilized in the minimum amount of dichloromethane with a little methanol then poured into diisopropyl ether. The precipitate is filtered. 16 mg (Yield=35%) of expected product is obtained in the form of an amorphous solid.

TLC: Rf=0.3 (silicagel, eluent: dichloromethane-methanol-water-acetic acid 90-10-1-1).

1H-NMR (MeOD): δ 1.12 (t, 3H, CH2-CH3); 1.49 and 1.95 (2m, 5H, N—CH2-CH2-CH—CH2-CH2); 2.51 (q, 2H, CH2-CH3); 3.00 and 3.52 (2m, 4H, N—CH2-CH2-CH—CH2-NH); 3.39 (d, 2H, CH—CH2-NH); 3.77 and 4.01 (2m, 2H, NH—CH2-CH—NH); 3.86 (s, 3H, O—CH3); 4.56 (m, 1H, NH—CH2-CH—NH); 5.07 (m, 2H, O—CH2-Ph); 6.91 (d, 1H, CH═CH benzimidazole); 6.96 (s, 1H, NH—C═CH—C—OCH3); 7.32 (m, 6H, Ph, CH═CH benzimidazole); 8.20 (s, 1H, N═CH—N).

HPLC/MS: 603 (MH+);

Example 41

Synthesis of 2,5-dimethyl-4,6-dihydroxy-pyrimidine

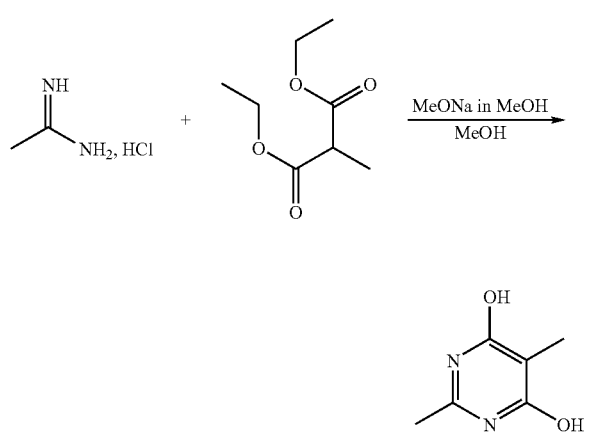

A single-necked flask containing 40 ml of methanol, placed under a nitrogen atmosphere, is cooled down to 0° C. with an ice bath, 9.72 g of sodium methylate (i.e. a solution of concentration c=3 mol.l$^{-1}$) is added to the reaction mixture then 5 g (53 mmoles) of acetamidine hydrochloride is added at 0° C. and in small quantities. Stirring is maintained at ambient temperature for about twenty minutes, then 8.3 ml of diethyl methylmalonate is added dropwise. Stirring is maintained for 3 hours. Then the methanol is condensed under reduced pressure (2 kPa). The crude product obtained is taken up in a minimum amount of water, followed by cooling down to 0° C. then acidifying with pure acetic acid to a pH of between 4 and 5. The white precipitate formed is filtered and rinsed with water, ethyl ether and pentane. Then the white product is dried over P$_2$O$_5$ under reduced pressure (0.2 kPa). 3.3 g (Yield=49%) of expected product is obtained.

TLC: Rf=0.2 (Silicagel, eluent: dichloromethane-methanol-water-acetic acid 85-15-2-2).

1H-NMR (DMSOd6): δ 1.68 (s, 3H, OH—CH═C—CH3); 2.18 (s, 3H, N═C—CH3).

Synthesis of 2,5-dimethyl-4,6-dichloro pyrimidine

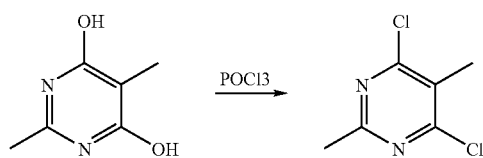

A mixture of 3.3 g (23.5 mmoles) of 2,5-dimethyl-4,6-dihydroxy-pyrimidine and 15 ml of phosphorus oxychloride, is taken to reflux for 8 hours. After returning to ambient temperature, the reaction medium is poured slowly into a mixture of ice and water. This aqueous phase is extracted with ethyl acetate. The organic phase is washed with a saturated solution of sodium bicarbonate then dried over magnesium sulphate and evaporated to dryness under reduced pressure (2 kPa). 3.39 g (Yield=81%) of expected product is obtained.

TLC: Rf=0.9 (Silicagel, eluent: ethyl acetate 100%)

1H-NMR (CDCl3): δ 2.46 (s, 3H, Cl—CH═C—CH3); 2.68 (s, 3H, N═C—CH3)

MS: 177/179 (MH+).

Synthesis of 6-[4-(1,2,3,4-tetrahydro-1,8-naphthyridin-7-yl)-1-piperidinyl]-2,5-dimethyl-4-chloro-pyrimidine

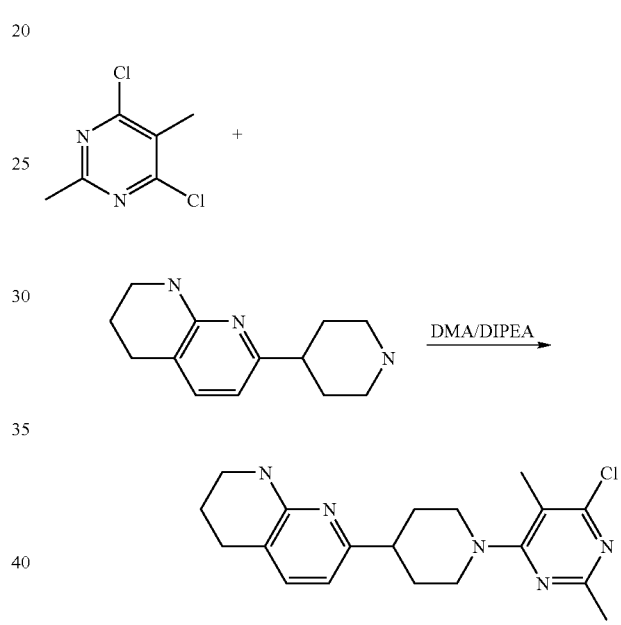

2 g (11.3 mmoles) of 4,6-dichloro-2,5-dimethyl-pyrimidine solubilized in 25 ml of dimethylacetamide and 5 ml of diisopropylethylamine is added into a single-necked flask containing 2.95 g (13.5 mmoles) of 4-(1,2,3,4-tetrahydro-1,8-naphthyridin-7-yl)-1-piperidine freed from its salt. This mixture is heated at 130° C. for 4 hours then concentrated to dryness under vacuum. The residue obtained is taken up in a mixture of water, ethyl acetate and a saturated solution of sodium bicarbonate. The organic phase is separated and the aqueous phase reextracted with ethyl acetate. The combined organic phases are dried over magnesium sulphate then the solvent is evaporated off under reduced pressure (2 kPa). The residue is chromatographed on silicagel eluting with a gradient of ethyl acetate (100%) then ethyl acetate-methanol (95-5). 2.2 g (Yield=55%) of expected product is obtained.

Preparation of naphthyridine in free amine form:

8.3 g of naphthyridine is displaced from its salt by 6 mass equivalents of basic amberlyst A21 resin (resin of R—NMe$_2$ type) in a CH$_2$Cl$_2$/MeOH/AcOEt mixture 1/1/1 under stirring for 30 minutes. The resin is washed beforehand and left to swell for 20 minutes in this solvent mixture. This operation must be repeated 3 times for the displacement of the salt to be complete.

After filtration of the resin and evaporation of the solvents, 2.95 g (13.5 mmoles) of free naphthyridine is obtained.

TLC: Rf=0.15 [silicagel, eluent: dichloromethane-methanol 95-5]

1H-NMR (CDCl3): δ 1.90 and 2.01 (2m, 6H, NH—CH2-CH2-CH2, N—CH2-CH2-CH—CH2-CH2); 2.26 (s, 3H, CH3); 2.51 (s, 3H, N═C—CH3); 2.72 (m, 3H, NH—CH2-CH2-CH2, N—CH2-CH2-CH—CH2-CH2); 2.97 and 3.97 (2m, 4H, CH2-CH2-N—CH2-CH2); 3.42 (m, 2H, NH—CH2-CH2-CH2); 6.41 and 7.16 (2d, 2H, CH═CH naphthyridine).

MS: 358(MH+).

Synthesis of (1,1-dimethylethyl)3-[[6-[4-(1,2,3,4-tetrahydro-1,8-naphthyridin-7-yl)-1-piperidinyl]-2,5-dimethyl-4-pyrimidinyl]amino]-N-[(phenylmethoxy)carbonyl]alaninate

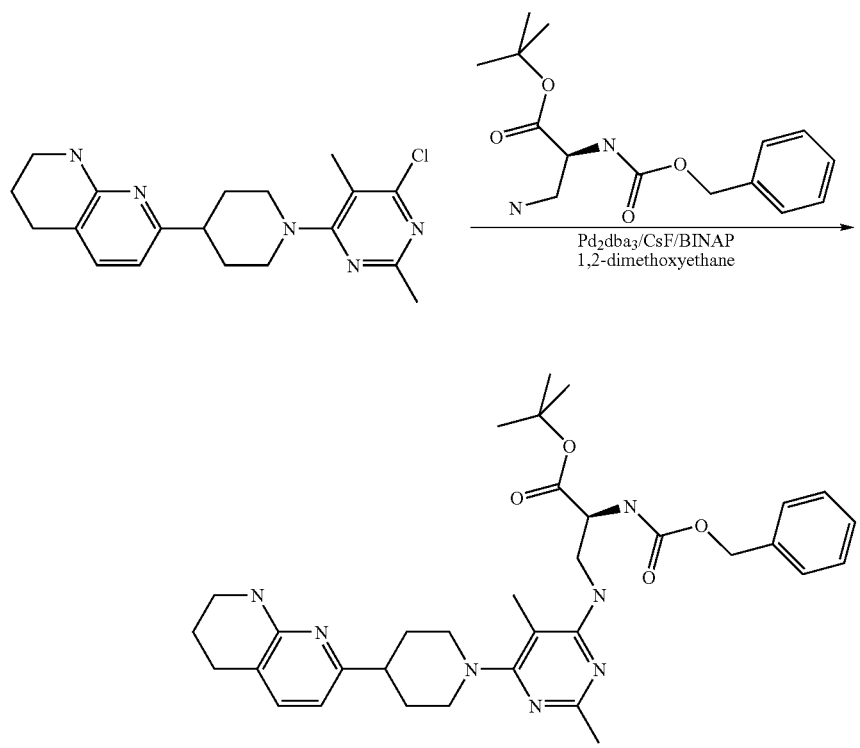

A mixture of 2.2 g (6.15 mmoles) of 6-[4-(1,2,3,4-tetrahydro-1,8-naphthyridin-7-yl)-1-piperidinyl]-2,5-dimethyl-4-chloro-pyrimidine and 2.17 g (7.38 mmoles) of (1,1-dimethylethyl) 3-amino-N-[(phenylmethoxy)carbonyl]alaninate (prepared according to J. Med. Chem. (2001), 44(8), 1158-1176), is heated under reflux for 24 hours in the presence of 1.31 g (8.61 mmoles) of caesium fluoride, 383 mg (0.615 mmoles) of (2,2'-bis(diphenylphosphino)-1,1'-binaphthyl and 281 mg (0.307 mmoles) of tris-dibenzylideneacetone) dipalladium(o), in 55 ml of 1,2-dimethoxyethane. The reaction mixture is then returned to ambient temperature, 281 mg (0.307 mmoles) of tris-dibenzylideneacetone)dipalladium(o) is added, then the reaction mixture is taken to reflux for another 24 hours. After cooling down the solution is concentrated to dryness under reduced pressure (2 kPa) then taken up in a mixture of water, ethyl acetate and a saturated solution of sodium bicarbonate. The organic phase is decanted and the aqueous phase is extracted with ethyl acetate. The combined organic phases are dried over magnesium sulphate and evaporated to dryness under reduced pressure (2 kPa). The residue is chromatographed on alumina with a gradient of isopropyl ether/ethyl acetate (50/50)-dichloromethane (50-50). The fractions containing the expected product are combined for a second purification on silicagel with a gradient of ethyl acetate-heptane-methanol 50-50-0 to 90-0-10. 550 mg (Yield=15%) of expected product is obtained.

TLC: Rf=0.3 (silicagel, eluent: dichloromethane-methanol 90-10)

1H-NMR (CDCl3): δ 1.46 (s, 9H, tBu); 1.92 (m, 9H, NH—CH2-CH2-CH2, N—CH2-CH2-CH—CH2-CH2, C═C—H3); 2.41 (s, 3H, N═C—CH3); 2.70 (m, 3H, NH—CH2-CH2-CH2, N—CH2-CH2-CH—CH2-CH2); 2.91 and 3.66 (2m, 4H, CH2-CH2-N—CH2-CH2); 3.44 (m, 2H, NH—CH2-CH2-CH2); 3.90 (m, 2H, NH—CH2-CH—NH); 4.38 (m, 1H, NH—CH2-CH—NH); 5.13 (s, 2H, O—CH2-Ph); 6.42 and 7.16 (2d, 2H, CH═CH naphthyridine); 7.35 (m, 5H, Ph).

MS: 616(MH+)

Synthesis of the corresponding acid:

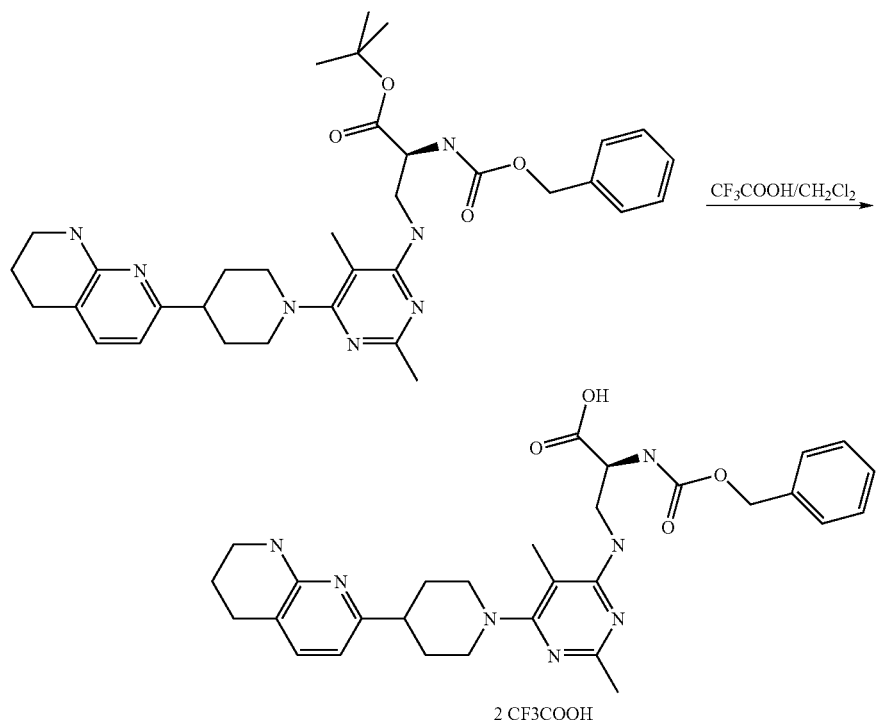

A mixture of 500 mg (0.81 mmoles) of (1,1-dimethylethyl) 3-[[6-[4-(1,2,3,4-tetrahydro-1,8-naphthyridin-7-yl)-1-piperidinyl]-2,5-dimethyl-4-pyrimidinyl]amino]-N-[(phenylmethoxy)carbonyl]alaninate and 5 ml of trifluoroacetic acid in 30 ml of dichloromethane is stirred at ambient temperature for 24 hours. Then toluene is added followed by evaporating the mixture to dryness. The residue is solubilized in the minimum amount of dichloromethane with a little methanol then poured into diisopropyl ether. The precipitate is filtered. 485 mg (Yield=76% expressed as ditrifluoroacetate) of expected product is obtained.

TLC: Rf=0.3 (silicagel, eluent: dichloromethane-methanol-water-acetic acid 90-10-1-1).

1H-NMR (CDCl3): δ 1.97 (m, 9H, NH—CH2-CH2-CH2, N—CH2-CH2-CH—CH2-CH2, C=C—CH3); 2.54 (s, 3H, N=C—CH3); 2.78 (m, 2H, NH—CH2-CH2-CH2); 2.98 (m, 1H, N—CH2-CH2-CH—CH2-CH2); 3.22 and 3.80 to 4.07 (2m, 6H, N—CH2-CH2-CH—CH2-CH2, NH—CH2-CH—NH); 3.51 (m, 2H, NH—CH2-CH2-CH2); 4.45 (m, 1H, NH—CH2-CH—NH); 5.10 (s, 2H, O—CH2-Ph); 6.42 and 7.37 (2m, 3H, CH=CH naphthyridine, mobile NH); 7.32 (m, 5H, Ph).

MS: 560 (MH+); 426 [MH+−(COOCH2Ph)]+.

Pharmacological test: Kistrin/Vitronectin Receptor ($\alpha_v\beta_3$) ELISA test Protocol:

96-well MaxiSorp plates are coated overnight at 40° C. with 100 μl of Kistrin at 1 μg/ml (dilution in coating buffer: 0.05M (carbonate)/NaOH pH 9.6. The next day, the wells are emptied and the ligands (kistrin) are then fixed (fixation buffers: PBS containing 0.5% BSA (pH=7.4)) for 1 hour at ambient temperature under gentle stirring of 125 rpm. The wells are washed six times (washing buffer: PBS containing 0.05% Tween 20 (pH 7.7) then the following is added per well and in this order:

40 μl of incubation buffer

10 μl of the dilution of the product to be tested (the products are diluted in a 50:50 DMSO/water mixture)

50 μl of human $\alpha_v\beta_3$ receptor (cf Pytella et al. Methods Enzymol. (1987) 144 (Dilution in incubation buffer, adapted according to the batch of receptor and according to the ligand). The ligand, the $\alpha_v\beta_3$ receptor and the products to be studied are co-incubated for 3 hours at ambient temperature with gentle stirring of 125 rpm.

The wells are again washed six times, then incubated for 2 hours at ambient temperature with gentle stirring of 125 rpm, in the presence of 100 μl of anti-receptor antibody coupled to a peroxidase (The 4B12-HRP antibody is diluted in incubation buffer (50 mM TRIS pH 7.4; 0.5% BSA; 0.05% Tween 20; 1 mM $MnCl_2$; 50 μM $CaCl_2$; 50 μM $MgCl_2$; 100 mM NaCl). The dilution is to be adapted according to the batch of receptor.

The wells are then washed six times before measurement of the ligand-receptor bond is carried out using a peroxidase developer kit (TBM Microwell Peroxidase Substrate System Kirkegaard; Ref cat 50-76-00).

This kit contains a flask A of substrate (3,3', 5,5'-tetramethylebenzidine at 0.4 g/l) and a flask B (0.02% $H_2O_2$ in Citrate/Citric acid). Extemporaneously, one volume of A is mixed with one volume of B, then the reaction mixture is distributed at a rate of 100 μl/well.

The enzymatic reaction develops between 6 to 10 minutes for Kistrin/$\alpha_v\beta_3$ then its development is stopped by the addition of 100 μl of 1M phosphoric acid. The optical density is determined at 450 nm.

Expression of the results

The following curve is plotted: the bond percentage as a function of the logarithm of each concentration of the tested product.

For each product the IC50 is determined according to the following formula:

$$IC50 = (B0 + Bmin)/2$$

B0 = Maximum bond in the absence of any product
Bmin = Minimum bond in the presence of the highest concentration of the product.

| EXAMPLE | K/VnR IC$_{50}$ (nM) |
|---------|----------------------|
| 1 | 3 |
| 2 | 160 |
| 3 | 3.1 |
| 4 | 5.1 |

Activity In Vivo

Hypercalcemia induced by the parathyroid hormone (PTH) in a thyroparathyroidectomized (TPXT) rat model Stimulation of bone resorption is induced in TPXT rats by perfusion of PTH and the variations of bone resorption are monitored by the concentration of calcium in the serum.

Male Sprague Dawley rats weighing 150-200 g are thyroparathyroidectomized. The rats are subjected to a standard diet containing 7g Ca/kg (UAR) and Volvic water. The effectiveness of the thyroparathyroidectomy is tested by measuring the concentrations of Ca in the serum 8 days after the operation in animals which have been starved since the previous day. The rats are considered as thyroparathyroidectomized when the Ca levels in the serum are less than 80 mg/l. The PTH (1-34) of the rat (Bachem) is dissolved in 0.15M of NaCl Cys.HCl 2% and delivered by osmotic minipumps (ALZET 2001D) at a dose of 200 pmol/kg/h. The minipumps are introduced into the intraperitoneal cavities under anaesthesia (ketamine—75 mg/kg and acepromazine—2.5 mg/kg) of the TPXT rats which have been starved since the previous day. The control TPXT rats receive the minipumps filled with the PTH vehicle.

Either the product to be tested or the vehicle (controls and rats treated with the PTH) are administered twice by subcutaneous route (2 ml/kg of body weight) at time 0 and 3 hours after the start of the infusion of PTH. The test is continued for the next 6 hours. At the end of the treatment, all the blood is collected after decapitation. The blood samples are centrifuged at 3000 rpm for 15 minutes (CR422 Jouan) in order to obtain the serum.

The total concentrations of Ca in the serum are measured by colorimetry (Ciba-Corning) using an IEMS Labsystems microplate reading system, at 540 nm.

The difference between the average calcemia values of the treated rats and the control groups is analyzed by variance and by the Dunnett test.

The activity of a product is calculated by the following formula:

$$\% \text{ effect} = \frac{\text{Calcemia (product)} - \text{calcemia (}PTH\text{)}}{\text{Calcemia (}PTH\text{)} - \text{calcemia (control)}} \times 100$$

The products of Examples 6, 9, 13 and 15 to 19 tested by the method described above were shown to be active at doses ranging from twice 1 mg/kg to twice 10 mg/kg by subcutaneous route in the rat.

The invention claimed is:

1. A compound of formula (I):

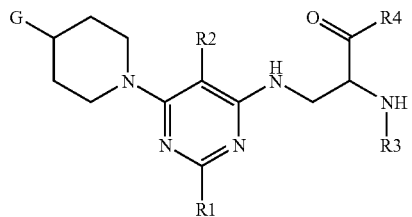

including all stereoisomeric forms thereof, physiologically acceptable addition salts thereof, as well as mixtures of any two or more thereof, in which:

G represents:
$R^7R^8N$—C(=$NR^6$)—NH—CO—;
Het-NH—CO—;
Het-NH—CH$_2$—; or
Het-,
Het representing a monocyclic or polycyclic system, each ring being constituted by 4 to 10 aromatic or non aromatic members, the ring or at least one of the rings containing 1 to 4 nitrogen atoms, substituted or non substituted by one or more $R^9$ groups;

$R^1$ represents a hydrogen atom; a ($C_5$-$C_{14}$)-aryl; ($C_5$-$C_{14}$)-aryl-($C_1$-$C_4$) alkyl-group; an amino radical non substituted or monosubstituted or disubstituted by an alkyl radical and/or an acyl radical containing 1 to 4 carbon atoms;

$R^2$ represents a hydrogen atom; a halogen atom; a nitro group; an alkyl radical containing 1 to 4 carbon atoms; an amino radical non substituted or monosubstituted or disubstituted by an alkyl radical and/or an acyl radical containing 1 to 4 carbon atoms; a —(CH$_2$)$_{0-2}$—CO$_2$R$^5$ group; or a —(CH$_2$)$_{0-2}$—OR$^5$ group;

$R^3$ represents:
a hydrogen atom;
a —CO$_2$R$^5$ radical;
a —SO$_2$R$^5$ radical or
a monocyclic or polycyclic system, each ring being constituted by 4 to 10 aromatic or non aromatic members, the ring or at least one of the rings containing 1 to 4 heteroatoms chosen from N, O or S, substituted or non substituted by one or more $R^9$ radicals, $R^4$ represents OH; ($C_1$-$C_8$)-alkoxy-; ($C_5$-$C_{14}$)-aryl-($C_1$-$C_4$)-alkyloxy-; ($C_5$-$C_{14}$)-aryloxy-, ($C_3$-$C_{12}$)-cycloalkyloxy; ($C_3$-$C_{12}$)-cycloalkyl-($C_1$-$C_4$)-alkyloxy-; ($C_1$-$C_8$)-alkylcarbonyloxy-($C_1$-$C_4$)-alkyloxy-;($C_5$-$C_{14}$)-aryl-($C_1$-$C_4$)-alkylcarbonyloxy-($C_1$-$C_4$) alkyloxy-; ($C_1$-$C_8$)-dialkylaminocarbonylmethyloxy-; ($C_5$-$C_{14}$)-aryl-($C_1$-$C_4$)-dialkylaminocarbonylmethyloxy-; an amino radical non substituted or monosubstituted or disubstituted by a ($C_1$-$C_4$)-alkyl and/or ($C_5$-$C_{14}$)-aryl and/or ($C_5$-$C_{14}$)-aryl-($C_1$-$C_4$)-alkyl- radical and/or a ($C_1$-$C_5$)-acyl radical; or the remainder of a D- or L- amino acid;

$R^5$ represents ($C_1$-$C_8$)-alkyl; ($C_5$-$C_{14}$)-aryl; ($C_5$-$C_{14}$)-aryl-($C_1$-$C_4$)-alkyl-; ($C_3$-$C_{12}$)-cycloalkyl or ($C_3$-$C_{12}$)-cycloalkyl-($C_1$-$C_4$)-alkyl-, bicycloalkyl-($C_1$-$C_4$)-alkyl-, tricycloalkyl-($C_1$-$C_4$)-alkyl-, the said aryl, alkyl, cycloalkyl, bicycloalkyl and tricycloalkyl radicals being non substituted or substituted by one or more chosen $R^9$ groups;

$R^6$ represents a hydrogen atom; a hydroxyl; nitro, $(C_1-C_6)$-alkyl-O—CO—; or $(C_1-C_6)$-alkyl-O—CO—O— group;

$R^7$ and $R^8$, independently of one another represent a hydrogen atom or a $(C_1-C_6)$-alkyl radical non substituted or substituted by $R^9$;

$R^9$ represents halogen; amino; nitro; hydroxyl, $(C_1-C_4)$-alkyloxy-; $(C_1-C_4)$-alkylthio-; carboxy; $(C_1-C_4)$-alkyloxycarbonyl-; $(C_1-C_8)$-alkyl non substituted or substituted by one or more halogen atoms, $(C_5-C_{14})$-aryl, $(C_5-C_{14})$-aryl-$(C_1-C_4)$-alkyl-;

it being understood that the aryl radicals can be non substituted or substituted by one or more identical or different radicals selected from the group consisting of $(C_1-C_8)$-alkyl, in particular $(C_1-C_4)$-alkyl, hydroxyl, $(C_1-C_8)$-alkyloxy, $(C_1-C_8)$-alkylthio, halogen selected from the group consisting of fluorine, chlorine and bromine, nitro, amino, $(C_1-C_4)$-alkylamino, di-$(C_1-C_4)$-alkylamino, trifluoromethyl, methylenedioxy, cyano, aminocarbonyl, $(C_1-C_4)$-alkylaminocarbonyl, di-$(C_1-C_4)$-alkylaminocarbonyl, carboxy, $(C_1-C_4)$-alkoxycarbonyl, phenyl, phenoxy benzyl and benzyloxy.

2. The compound according to claim 1 in which G represents a Het, Het-NHCO—, or Het-NH—$CH_2$— group with Het representing the following heterocycles:

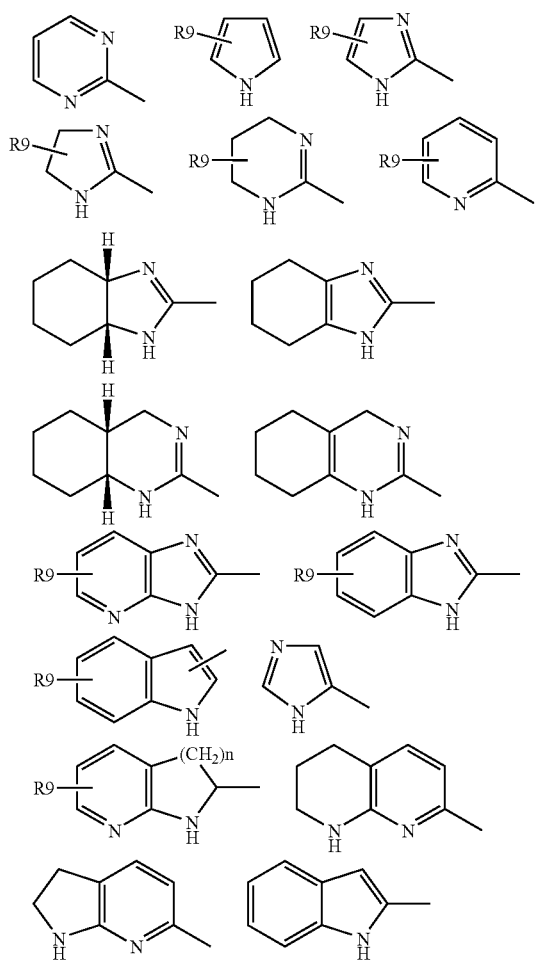

3. The compound according to any one of claims 1 to 2 in which $R^3$ is:

a heterocycle chosen from

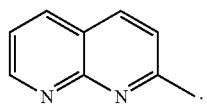

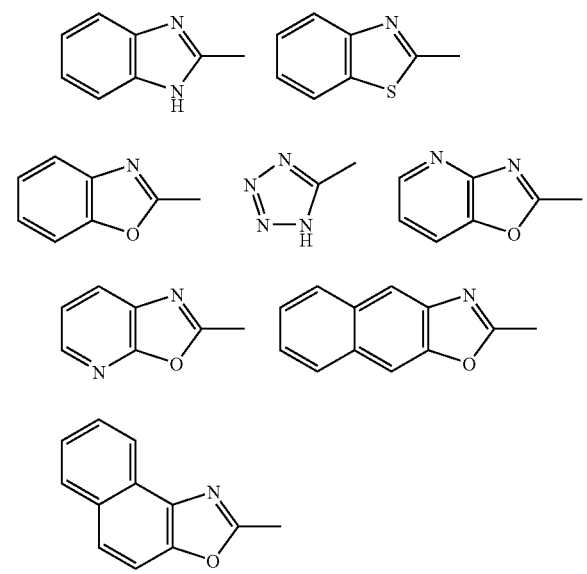

as well as pharmaceutically acceptable addition salts thereof.

4. The compound according to any one of claims 1 to 2 in which $R^3$ is a benzyloxycarbonyl group, as well as pharmaceutically acceptable addition salts thereof.

5. The compound according to any one of claims 1 to 2 in which $R^2$ is a hydrogen, an alkyl radical containing 1 to 4 carbon atoms or a fluorine atom, as well as pharmaceutically acceptable addition salts thereof.

6. The compound according to claim 5 in which $R^2$ is a methyl or ethyl.

7. The compound according to any one of claims 1 to 2 in which:

G represents

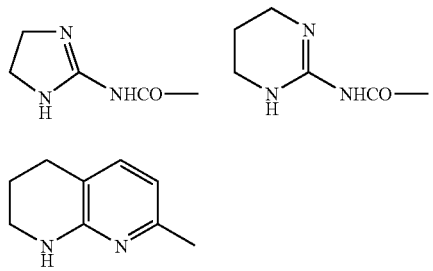

as well as pharmaceutically acceptable addition salts thereof.

8. The compound according to any one of claims 1 to 2 in which:

G represents

[chemical structures: 2-imidazoline-NHCO—, hexahydropyrimidine-NHCO—, and 7-methyl-1,2,3,4-tetrahydro-1,8-naphthyridine]

$R^1$ represents a hydrogen atom, $R^2$ represents a hydrogen atom, a fluorine atom, a methyl radical or an ethyl radical, $R^3$ represents a benzyloxycarbonyloxy group, and $R^4$ represents a hydroxy group, as well as pharmaceutically acceptable addition salts thereof.

9. The compound according to any one of claims 1 to 2 the names of which follow:

3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alanine, 3-[[5-ethyl-6-[4-[( 1,2,3,4,5,6-hexahydro-2-pyrimidinyl)iminocarbonyl]1-piperidinyl]-4-pyrimidinyl]amino]-N-[(phenylmethoxy)carbonyl]alanine, 3-[[6-[4-(1,2,3,4-tetrahydro-1,8-naphthyridin-7-yl)-1-piperidinyl]-5-methyl-4-pyrimidinyl]amino]-N-[(phenylmethoxy)carbonyl]alanine, 3-[[6-[4-[(1,2,3,4,5,6-hexahydro-2-pyrimidinyl)iminocarbonyl]-1piperidinyl]-5-methyl-4-pyrimidinyl]amino]-N-[(phenylmethoxy)carbonyl]alanine, ethyl 3-[[5-ethyl-6-[4-(1,2,3,4-tetrahydro-1,8-naphthyridin-7-yl)-1-piperidinyl]-4-pyrimidinyl]amino]-N-[(phenylmethoxy)carbonyl]alaninate, isopropyl 3-[[6-[4-(1,2,3,4-tetrahydro-1,8-napbthyridin-7-yl)-1-piperidinyl]-5-methyl-4-pyrimidinyl]amino]-N-[(phenylmethoxy)carbony]alaninate, (1,1-dimethylethyl)3-[[5-ethyl-6-[4-(1,2,3,4-tetrahydro-1,8-naphthyridin-7yl)-1-piperidinyl]-4-pyrimidinyl]amino]-N-[(phenylmethoxy)carbonyl]alaninate, (1,1-dimethylethyl)3-[[5-methyl-6-[4-(1,2,3,4-tetrahydro-1,8-naphthyridin-7-yl)-1-piperidinyl]-4-pyrimidinyl]amino]-N-[(phenylmethoxy)carbonyl]alaninate, (1,1-dimethylethyl)3-[[5-ethyl-6-[4-(1,2,3,4-tetrahydro-1,8-naphthyridin-7-yl)-1-piperidinyl]-4-pyrimidinyl]amino]-N-(1-naphthalenesulphonyl)alaninate, in (R) configuration or (S) configuration or addition salts thereof, as well as mixtures of any two or more thereof.

10. A process for the preparation of a compound of formula (I) in which a) a compound of formula (II)

[chemical structure (II)]

in which $R^1$, $R^2$, $R^3$ and $R^4$ are as defined in claim 1 is reacted, a) with a compound of formula (III)

[chemical structure (III)]

in which G is as defined in claim 1 in the presence of a base or a transition metal coupling reagent b) the compound of formula (I) thus obtained is subjected, optionally to cleavage of the $R^3$—NH— function in order to regenerate the free amine, followed by condensation of the $R^3$ radicals of —CO2-$R^5$ or —SO$_2$—$R^5$ structure, and optionally to hydrolysis and optionally to esterification or to amidification and/or to salification.

11. A process for the preparation of a compound of formula (I) in which a) a compound of formula (II) as defined in claim 10 is reacted with a compound of formula (IIIa):

[chemical structure (IIIa)]

in order to obtain the intermediate compound of formula (IV):

[chemical structure (IV)]

b) the compound of formula (IV) is reacted with a compound of formula of Het-NH$_2$, in order to obtain the compounds of formula (I) with G representing a Het-NHCO— group, c) the compound of formula (I) obtained is subjected, optionally to cleavage of the $R^3$—NH— function in order to regenerate the free amine, followed by condensation of $R^3$ radicals of —CO$_2$—$R^5$ or —SO$_2$—$R^5$ structure, and optionally, to esterification or to amidification and/or to salification.

12. A process for the preparation of a compound of formula (I) according to one of claims 1 to 2, characterized in that
a) a product of general formula (IIa)

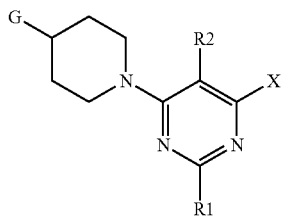
(IIa)

in which $R^1$, $R^2$, G and X are as defined previously, is reacted with a product of formula (VI)

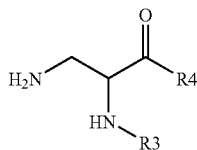
(VI)

in which $R^3$ and $R^4$ are as defined previously, either in the presence of a strong base, or by catalysis with palladium,
b) then the product of formula (I) is subjected, optionally to cleavage of the $R^3$—NH— function in order to regenerate the free amine, followed by condensation of the $R^3$ radicals of —$CO_2$—$R^5$ or —$SO_2$—$R^5$ structure, and optionally, to hydrolysis and optionally to esterification or to amidification and/or to salification.

13. A pharmaceutical composition comprising a compound as defined in claim 1 as well as one or more excipients.

14. A method for the treatment of osteoporosis, said method comprising administering to a subject in need thereof an effective amount of a compound of formula (I) and/or physiologically acceptable salts thereof as defined according to any one of claims 1 to 2.

15. A method for the treatment of restenosis, arteriosclerosis, nephropathies or retinopathies, said method comprising administering to a subject in need thereof an effective amount of a compound of formula (I) and/or physiologically acceptable salts thereof as defined according to any one of claims 1 to 2.

* * * * *

UNITED STATES PATENT AND TRADEMARK OFFICE
CERTIFICATE OF CORRECTION

| | | |
|---|---|---|
| PATENT NO. | : 7,582,640 B2 | Page 1 of 1 |
| APPLICATION NO. | : 10/536028 | |
| DATED | : September 1, 2009 | |
| INVENTOR(S) | : Ruxer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Fifteenth Day of March, 2011

David J. Kappos
*Director of the United States Patent and Trademark Office*